(12) United States Patent
Draghia-Akli et al.

(10) Patent No.: US 7,241,744 B2
(45) Date of Patent: Jul. 10, 2007

(54) TREATING ANEMIA IN SUBJECTS BY ADMINISTRATION OF PLASMIDS ENCODING GROWTH HORMONE RELEASING HORMONE

(75) Inventors: Ruxandra Draghia-Akli, Houston, TX (US); Robert H. Carpenter, Bastrop, TX (US); Douglas R. Kern, The Woodlands, TX (US); Robert J. Schwartz, Houston, TX (US); Glen King, Rosharon, TX (US); Kevin Hahn, Missouri City, TX (US); Malcolm K. Brenner, Bellaire, TX (US)

(73) Assignees: Baylor College of Medicine, Houston, TX (US); ADViSYS, Inc., The Woodlands, TX (US)

(*) Notice: Subject to any disclaimer, the term of this patent is extended or adjusted under 35 U.S.C. 154(b) by 35 days.

(21) Appl. No.: 10/315,907

(22) Filed: Dec. 10, 2002

(65) Prior Publication Data

US 2004/0057941 A1    Mar. 25, 2004

Related U.S. Application Data

(60) Provisional application No. 60/339,610, filed on Dec. 11, 2001.

(51) Int. Cl.
| | | |
|---|---|---|
| A01N 43/04 | (2006.01) | |
| A61K 31/70 | (2006.01) | |
| A01N 63/00 | (2006.01) | |
| A01N 65/00 | (2006.01) | |
| C07H 21/02 | (2006.01) | |
| C07H 21/04 | (2006.01) | |
| A61K 38/24 | (2006.01) | |
| C07K 1/00 | (2006.01) | |
| C07K 17/00 | (2006.01) | |

(52) U.S. Cl. .................. 514/44; 536/321; 530/399; 424/93.1

(58) Field of Classification Search ............ 435/320.1, 435/172.3, 325; 514/44; 424/93.1; 536/23.1, 536/23.5; 530/93.1
See application file for complete search history.

(56) References Cited

U.S. PATENT DOCUMENTS

| | | |
|---|---|---|
| 4,223,019 A | 9/1980 | Momany |
| 4,223,020 A | 9/1980 | Momany |
| 4,223,021 A | 9/1980 | Momany |
| 4,224,316 A | 9/1980 | Momany |
| 4,226,857 A | 10/1980 | Momany |
| 4,228,156 A | 10/1980 | Momany |
| 4,228,158 A | 10/1980 | Momany |
| 4,410,512 A | 10/1983 | Bowers |
| 4,684,611 A | 8/1987 | Schilperoort |
| 4,833,166 A | 5/1989 | Grosvenor |
| 4,839,344 A | 6/1989 | Bowers |
| 4,952,500 A | 8/1990 | Finnerty |
| 4,956,288 A | 9/1990 | Barsoum |
| 5,023,322 A | 6/1991 | Kovacs |
| 5,036,045 A | 7/1991 | Thorner |
| RE33,699 E | 9/1991 | Drengler |
| 5,061,690 A | 10/1991 | Kann |
| 5,084,442 A | 1/1992 | Felix |
| 5,134,120 A | 7/1992 | Boyd |
| 5,137,872 A | 8/1992 | Seely |
| 5,292,721 A | 3/1994 | Boyd |
| 5,302,523 A | 4/1994 | Coffee |
| 5,322,783 A | 6/1994 | Tomes |
| 5,384,253 A | 1/1995 | Krzyzek |
| 5,439,440 A | 8/1995 | Hofmann |
| 5,464,765 A | 11/1995 | Coffee |
| 5,486,505 A | 1/1996 | Bowers |
| 5,538,877 A | 7/1996 | Lundquist |
| 5,538,880 A | 7/1996 | Lundquist |
| 5,550,318 A | 8/1996 | Adams |
| 5,563,055 A | 10/1996 | Townsend |
| 5,580,859 A | 12/1996 | Felgner |
| 5,589,466 A | 12/1996 | Felgner |
| 5,591,616 A | 1/1997 | Hiei |

(Continued)

FOREIGN PATENT DOCUMENTS

| | | |
|---|---|---|
| EP | 1052286 A2 * | 11/2000 |
| WO | WO 94/09699 | 5/1994 |
| WO | WO- 95/06128 | 3/1995 |
| WO | WO 99/05300 | 2/1999 |
| WO | WO 99/05300 A2 | 2/1999 |
| WO | WO 01/06988 A2 | 2/2001 |

OTHER PUBLICATIONS

Romano et al. "Latest developments in gene transfer technology: achievements, perspectives, and controversies over therapeutic applications." 18:19-39, 2000.*

(Continued)

Primary Examiner—Joseph Woitach
Assistant Examiner—Robert M. Kelly
(74) Attorney, Agent, or Firm—Jackson Walker L.L.P.

(57) ABSTRACT

The present invention pertains to compositions and methods for plasmid-mediated supplementation. The compositions and method are useful for retarding the growth of the tumor, and retarding cachexia, wasting, anemia and other effects that are commonly associated in cancer bearing animals. Overall, the embodiments of the invention can be accomplished by delivering an effective amount of a nucleic acid expression construct that encodes a GHRH or functional biological equivalent thereof into a tissue of an animal and allowing expression of the encoded. gene in the animal. For example, when such a nucleic acid sequence is delivered into the specific cells of the tissue specific constitutive expression is achieved.

1 Claim, 20 Drawing Sheets

U.S. PATENT DOCUMENTS

| | | | |
|---|---|---|---|
| 5,610,042 | A | 3/1997 | Chang |
| 5,656,610 | A | 8/1997 | Shuler |
| 5,696,089 | A | 12/1997 | Felix |
| 5,702,384 | A | 12/1997 | Umeyama |
| 5,702,932 | A | 12/1997 | Hoy |
| 5,704,908 | A | 1/1998 | Hofmann |
| 5,736,524 | A | 4/1998 | Content |
| 5,756,264 | A | 5/1998 | Schwartz |
| 5,776,901 | A | 7/1998 | Bowers |
| 5,780,448 | A | 7/1998 | Davis |
| 5,789,215 | A | 8/1998 | Berns |
| 5,792,747 | A | 8/1998 | Schally |
| 5,846,936 | A | 12/1998 | Felix |
| 5,847,066 | A | 12/1998 | Coy |
| 5,874,534 | A | 2/1999 | Vegeto |
| 5,925,564 | A * | 7/1999 | Schwartz et al. ........... 435/325 |
| 5,935,934 | A | 8/1999 | Vegeto |
| 5,945,100 | A | 8/1999 | Fick |
| 5,981,274 | A | 11/1999 | Tyrrell |
| 5,994,624 | A | 11/1999 | Trolinder |
| 6,194,402 | B1 | 2/2001 | Bach et al. |
| 6,468,986 | B1 * | 10/2002 | Zuckermann et al. ......... 514/44 |
| 6,551,996 | B1 | 4/2003 | Schwartz et al. |

OTHER PUBLICATIONS

Verma et al. "Gene therapy—promises, problems and prospect." Nature 389:239-242, 1997.*

Prchal et al. "Deliver on demand—a new era of gene therapy?" The New England Journal of Medicine 348(13): 1282-1283, 2004.*

Bowie, et al. (1990) Science, 247: 1306-10.*

Parsons (1976) Peptide Hormones, University Park Press, Baltimore, MD., pp. 1-6.*

Gorecki (2001) Exp. Opin. Emerg. Drugs, 6(2): 187-98.*

Eck, et al. (1996) Goodman & Gilman's The Pharmacological Basis of Therapeutics, 9th Ed., McGraw-Hill, New York, NY., pp. 77-101.*

Deonarain (1998) Exp. Opin. Ther. Pat., 8(1):53-69.*

Rivera, et al. (2005) Blood, 105(1):382-86.*

Ballas, et al. (2004) Microcirculation, 11: 209-25.*

Abruzzese,R.V., Godin,D., Burcin,M., Mehta,V., French,M., Li,Y., O'Malley,B.W., and Nordstrom,J.L. (1999). Ligand-dependent regulation of plasmid-based transgene expression in vivo. Hum. Gene Ther. 10, 1499-1507.

Aihara,H. and Miyazaki,J. (1998). Gene transfer into muscle by electroporation in vivo. Nat. Biotechnol. 16, 867-870.

Al Suwaidi,J., Reddan,D.N., Williams,K., Pieper,K.S., Harrington,R.A., Califf,R.M., Granger,C.B., Ohman,E.M., and Holmes,D.R., Jr. (2002). Prognostic implications of abnormalities in renal function in patients with acute coronary syndromes. Circulation 106, 974-980.

Almendro,N., Bellon,T., Rius,C., Lastres,P., Langa,C., Corbi,A., and Bernabeu,C. (1996). Cloning of the human platelet endothelial cell adhesion molecule-1 promoter and its tissue-specific expression. Structural and functional characterization. J. Immunol. 157, 5411-5421.

Aratani,Y., Okazaki,R., and Koyama,H. (1992). End extension repair of introduced targeting vectors mediated by homologous recombination in mammalian cells. Nucleic Acids Res. 20, 4795-4801.

Argente,J., Pozo,J., and Chowen,J.A. (1996). The growth hormone axis: control and effects. Hormone Research 45 Suppl 1, 9-11.

Barber,M.D., Ross,J.A., and Fearon,K.C. (1999). Cancer cachexia. Surg. Oncol. 8, 133-141.

Bartlett,D.L., Charland,S., and Torosian,M.H. (1994). Growth hormone, insulin, and somatostatin therapy of cancer cachexia. Cancer 73, 1499-1504.

Bercu,B.B., Walker,R.F.(1997). Growth Hormone Secretagogues in Children with Altered Growth. Acta Paediatrica 86, 102-106.

Bettan,M., Emmanuel,F., Darteil,R., Caillaud,J.M., Soubrier,F., Delaere,P., Branelec,D., Mahfoudi,A., Duverger,N., and Scherman,D. (2000). High-level protein secretion into blood circulation after electric pulse-mediated gene transfer into skeletal muscle. Mol. Ther. 2, 204-210.

Blethen,S.L. and MacGillivray,M.H. (1997). A risk-benefit assessment of growth hormone use in children. Drug Saf 17, 303-316.

Blethen,S.L. and Rundle,A.C. (1996). Slipped capital femoral epiphysis in children treated with growth hormone. A summary of the National Cooperative Growth Study experience. Horm. Res. 46, 113-116.

Bohlen,P., Esch,F., Brazeau,P., Ling,N., and Guillemin,R. (1983). Isolation and characterization of the porcine hypothalamic growth hormone releasing factor. Biochem. Biophys. Res. Commun. 116, 726-734.

Boshart,M., Weber,F., Jahn,G., Dorsch-Hasler,K., Fleckenstein,B., and Schaffner,W. (1985). A very strong enhancer is located upstream of an immediate early gene of human cytomegalovirus. Cell 41, 521-530.

Bureau,M.F., Gehl,J., Deleuze,V., Mir,L.M., and Scherman,D. (2000). Importance of association between permeabilization and electrophoretic forces for intramuscular DNA electrotransfer. Biochim. Biophys. Acta 1474, 353-359.

Carbonelli,D.L., Corley,E., Seigelchifer,M., and Zorzopulos,J. (1999). A plasmid vector for isolation of strong promoters in *Escherichia coli*. FEMS Microbiol. Lett. 177, 75-82.

Chandler,S.D., Mayeda,A., Yeakley,J.M., Krainer,A.R., and Fu,X. D. (1997). RNA splicing specificity determined by the coordinated action of RNA recognition motifs in SR proteins. Proc. Natl. Acad. Sci. U. S. A 94, 3596-3601.

Chen,C. and Okayama,H. (1987). High-efficiency transformation of mammalian cells by plasmid DNA. Mol. Cell Biol. 7, 2745-2752.

Chevalier,R.L., Goyal,S., Kim,A., Chang,A.Y., Landau,D., and Leroith,D. (2000). Renal tubulointerstitial injury from ureteral obstruction in the neonatal rat is attenuated by IGF-1. Kidney Int. 57, 882-890.

Claustres,M., Chatelain,P., and Sultan,C. (1987). Insulin-like growth factor I stimulates human erythroid colony formation in vitro. J Clin. Endocrinol. Metab 65, 78-82.

Cocea,L. (1997). Duplication of a region in the multiple cloning site of a plasmid vector to enhance cloning-mediated addition of restriction sites to a DNA fragment. Biotechniques 23, 814-816.

Corpas,E., Harman,S.M., Pineyro,M.A., Roberson,R., and Blackman,M.R. (1993). Continuous subcutaneous infusions of growth hormone (GH) releasing hormone 1-44 for 14 days increase GH and insulin-like growth factor-I levels in old men. Journal of Cllinical Endocrinology & Metabolism 76, 134-138

Correa,P.N., Eskinazi,D., and Axelrad,A.A. (1994). Circulating erythroid progenitors in polycythemia vera are hypersensitive to insulin-like growth factor-1 in vitro: studies in an improved serum-free medium. Blood 83, 99-112.

Cremagnani,L., Cantalamessa,L., Orsalli,A., Vigna,L., Vallino,F., and Buccianti,G. (1993). Recombinant human erythropoietin (rhEPO) treatment potentiates growth hormone (GH) response to growth hormone releasing hormone (GHRH) stimulation in hemodialysis patients. Clin. Nephrol. 39, 282-286.

Crook,E.D., Washington,D.O., and Flack,J.M. (2002). Screening and prevention of chronic kidney disease. J. Natl. Med. Assoc. 94, 55S-62S.

Dai,B., Wu,H., Holthuizen,E., and Singh,P. (2001). Identification of a novel cis element required for cell density-dependent down-regulation of insulin-like growth factor-2 P3 promoter activity in Caco2 cells. J. Biol. Chem. 276, 6937-6944.

Danko,I. and Wolff,J.A. (1994). Direct gene transfer into muscle. [Review]. Vaccine 12; 1499-1502.

Davis,H.L., Whalen,R.G., and Demeneix,B.A. (1993). Direct gene transfer into skeletal muscle in vivo: factors affecting efficiency of transfer and stability of expression. Human Gene Therapy 4, 151-159.

Davis,M.P. and Dickerson,D. (2000). Cachexia and anorexia: cancer's covert killer. Support. Care Cancer 8, 180-187.

Demetri,G.D. (2001). Anaemia and its functional consequences in cancer patients: current challenges in management and prospects for improving therapy. Br. J. Cancer 84 Suppl 1:31-7., 31-37.

Diez,J., Iglesias,P., Sastre,J., Mendez,J., Selgas,R., and Gomez-Pan,A. (1996). Growth hormone responses to growth hormone-releasing hormone and clonidine before and after erythropoietin therapy in CAPD patients. Nephron 74, 548-554.

Dolnik, V., Novotny,M., and Chmelik,J. (1993). Electromigration behavior of poly-(L-glutamate) conformers in concentrated polyacrylamide gels. Biopolymers 33, 1299-1306.

Dorsch-Hasler,K., Keil,G.M., Weber,F., Jasin,M., Schaffner,W., and Koszinowski,U.H. (1985). A long and complex enhancer activates transcription of the gene coding for the highly abundant immediate early mRNA in murine cytomegalovirus. Proc. Natl. Acad. Sci. U. S. A 82, 8325-8329.

Draghia-Akli,R., Fiorotto,M.L., Hill,L.A., Malone,P.B., Deaver,D. R., and Schwartz,R.J. (1999). Myogenic expression of an injectable protease-resistant growth hormone-releasing hormone augments long-term growth in pigs. Nat. Biotechnol. 17, 1179-1183.

Draghia-Akli,R., Khan,A.S., Cummings,K.K., Parghi,D., Carpenter,R.H., and Brown,P.A. (2002a). Electrical Enhancement of Formulated Plasmid Delivery in Animals. Technology in Cancer Research & Treatment 1, 365-371.

Draghia-Akli,R., Li,X.G., and Schwartz,R.J. (1997). Enhanced growth by ectopic expression of growth hormone releasing hormone using an injectable myogenic vector. nature biotechnology 15, 1285-1289.

Draghia-Akli,R., Malone,P.B., Hill,L.A., Ellis,K.M., Schwartz,R.J., and Nordstrom,J.L. (2002B). Enhanced animal growth via ligand-regulated GHRH myogenic-injectable vectors. FASEB J. 16, 426-428.

Dubreuil,P., Petitclerc,D., Pelletier,G., Gaudreau,P., Farmer,C., Mowles, TF, and Brazeau,P. (1990). Effect of dose and frequency of administration of a potent analog of human growth hormone-releasing factor on hormone secretion and growth in pigs. Journal of Animal Science 68, 1254-1268.

Duck,S.C., Schwarz,H.P., Costin,G., Rapaport,R., Arslanian,S., Hayek,A., Connors,M., and Jaramillo,J. (1992). Subcutaneous growth hormone-releasing hormone therapy in growth hormone-deficient children: first year of therapy. Journal of Clinical Endocrinology & Metabolism 75, 1115-1120.

Edwards,B.K., Howe,H.L., and et al., (2002). Annual report to the nation on the status of cancer, 1973-1999, featuring implications of age and aging on U.S. cancer burden. Cancer 94, 2766-2792.

Esch,F.S., Bohlen,P., Ling,N.C., and et al., (1982). Characterization of a 40 residue peptide from a human pancreatic tumor with growth hormone releasing activity. Biochemical & Biophysical Research Communications 109, 152-158.

Evans,W.S., Vance,M.L., and et al., (1985). Effects of intravenous, subcutaneous, and intranasal administration of growth hormone (GH)-releasing hormone-40 on serum GH concentrations in normal men. Journal of Clinical Endocrinology & Metabolism 61, 846-850.

Fechheimer,M., Boylan,J.F., and et al., (1987). Transfection of mammalian cells with plasmid DNA by scrape loading and sonication loading. Proc. Natl. Acad. Sci. U. S. A 84, 8463-8467.

Fewell,J.G., MacLaughlin,F., and et al., (2001). Gene therapy for the treatment of hemophilia B using PINC-formulated plasmid delivered to muscle with electroporation. Mol. Ther. 3, 574-583.

Frohman,L.A., Downs,T.R., Heimer,E.P., and Felix,A.M. (1989). Dipeptidylpeptidase IV and trypsin-like enzymatic degradation of human growth hormone-releasing hormone in plasma. J. Clin. Invest. 83, 1533-1540.

Frohman,L.A., Thominet,J.L., and et al., (1984). Metabolic clearance and plasma disappearance rates of human pancreatic tumor growth hormone releasing factor in man. J. Clin. Invest. 73, 1304-1311.

Fryer,A.D. and Jacoby,D.B. (1993). Effect of inflammatory cell mediators on M2 muscarinic receptors in the lungs. Life Sci. 52, 529-536.

Gehl,J., Sorensen,T.H., Nielsen,K., Raskmark,P., Nielsen,S.L., Skovsgaard,T., and Mir,L.M. (1999). In vivo electroporation of skeletal muscle: threshold, efficacy and relation to electric field distribution. Biochim. Biophys. Acta 1428, 233-240.

German,M., Ashcroft,S., Docherty,K., Edlund,H., Edund,T., Goodison,S., Imura,H., Kennedy,G., Madsen,O., Melloul,D. (1995). The insulin gene promoter. A simplified nomenclature. Diabetes 44, 1002-1004.

Gilbert, R.A., Jaroszeski,M.J., and Heller,R. (1997). Novel electrode designs for electrochemotherapy. Biochim. Biophys. Acta 1334, 9-14.

Gopal, T.V. (1985). Gene transfer method for transient gene expression, stable transformation, and cotransformation of suspension cell cultures. Mol. Cell Biol. 5, 1188-1190.

Graham,F.L. and Van Der Eb,A.J. (1973). Transformation of rat cells by DNA of human adenovirus 5, Virology 54, 536-539.

Guillemin,R., Brazeau,P., Bohlen,P., Esch,F., Ling,N., and Wehrenberg,W.B. (1982). Growth hormone-releasing factor from a human pancreatic tumor that caused acromegaly. Science 218, 585-587.

Hafez,I.M., Maurer,N., and Cullis,P.R. (2001). On the mechanism whereby cationic lipids promote intracellular delivery of polynucleic acids. Gene Ther. 8, 1188-1196.

Hamm,A., Krott,N., Breibach,I., Blindt,R., and Bosserhoff,A.K. (2002). Efficient transfection method for primary cells, Tissue Eng 8, 235-245.

Harland,R. and Weintraub,H. (1985). Translation of mRNA injected into Xenopus oocytes is specifically inhibited by antisense RNA. J. Cell Biol. 101, 1094-1099.

Heller,R., Jaroszeski,M.J., Glass,L.F., Messina,J.L., Rapaport,D.P., Deconti,R.C., Fenske,N.A., Gilbert,R.A., Mir,L.M., and Reintgen,D.S. (1996). Phase I/II trial for the treatment of cutaneous and subcutaneous tumors using electrochemotherapy. Cancer 77, 964-971.

Herzog,R.W., Mount,J.D., Arruda,V.R., High,K.A., and Lothrop,C. D., Jr. (2001). Muscle-directed gene transfer and transient immune suppression result in sustained partial correction of canine hemophilia B caused by a null mutation. Mol. Ther. 4, 192-200.

Horlick,R.A. and Benfield,P.A. (1989). The upstream muscle-specific enhancer of the rat muscle creatine kinase gene is composed of multiple elements. Mol. Cell Biol. 9, 2396-2413.

Hostetter,T.H. and Lising,M. (2002). National Kidney Disease Education Program. J. Natl. Med. Assoc. 94, 72S-75S.

Inouye,C., Remondelli,P., Karin,M., and Elledge,S. (1994). Isolation of a cDNA encoding a metal response element binding protein using a novel expression cloning procedure: the one hybrid system. DNA Cell Biol. 13, 731-742.

Inouye,S., Nakazawa,A., and Nakazawa,T. (1985). Determination of the transcription initiation site and identification of the protein product of the regulatory gene xylR for xyl operons on the TOL plasmid. J. Bacteriol. 163,863-869.

Jardieu,P., Clark,R., Mortensen,D., and Dorshkind,K. (1994). In vivo administration of insulin-like growth factor I-stimulates primary B lymphopoiesis and enhances lymphocyte recovery after bone marrow transplantation. J Immunol. 152, 4320-4327.

Jaynes,J.B., Johnson,J.E., Buskin,J.N., Gartside,C.L., and Hauschka,S.D. (1988). The muscle creatine kinase gene is regulated by multiple upstream elements, including a muscle-specific enhancer. Mol. Cell Biol. 8, 62-70.

Kawamoto,T., Makino,K., Niwa,H., Sugiyama,H., Kimura,S., Amemura,M., Nakata,A., and Kakunaga,T. (1988). Identification of the human beta actin enhancer and its binding factor. Mol. Cell Biol. 8, 267-272.

Kawamoto,T., Makino,K., Orita,S., Nakata,A., and Kakunaga,T. (1989). DNA bending and binding factors of the human beta-actin promoter. Nucleic Acids Res. 17, 523-537.

Klamut,H.J., Bosnoyan-Collins,L.O., Worton,R.G., Ray,P.N., and Davis,H.L. (1996). Identification of a transcriptional enhancer within muscle intron 1 of the human dystrophin gene. Hum. Mol. Genet. 5, 1599-1606.

Klamut,H.J., Gangopadhyay,S.B., Worton,R.G., and Ray,P.N. (1990). Molecular and functional analysis of the muscle-specific promoter region of the Duchenne muscular dystrophy gene. Mol. Cell Biol. 10, 193-205.

Koo,G.C., Huang,C., Camacho,R., Trainor,C., Blake,J.T., Sirotina-Meisher,A., Schleim,K.D., Wu,T.J., Cheng,K., Nargund,R., and McKissick,G. (2001). Immune enhancing effect of a growth hormone secretagogue. J. Immunol. 166, 4195-4201.

Kraus,J., Woltje,M., Schonwetter,N., and Hollt,V. (1998). Alternative promoter usage and tissue specific expression of the mouse somatostatin receptor 2 gene. FEBS Lett. 428, 165-170.

Kurtz,A., Jelkmann,W., and Bauer,C. (1982). A new candidate for the regulation of erythropoiesis. Insulin-like growth factor I. FEBS Lett. 149, 105-108.

Kurtz,A., Matter,R., Eckardt,K.U., and Zapf,J. (1990). Erythropoiesis, serum erythropoietin, and serum IGF-I in rats during accelerated growth. Acta Endocrinol. (Copenh) 122, 323-328.

Lareyre,J.J., Thomas,T.Z., Zheng,W.L., Kasper,S., Ong,D.E., Orgebin-Crist,M.C., and Matusik,R.J. (1999). A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274, 8282-8290.

Larsen,P.R., Harney,J.W., and Moore,D.D. (1986). Sequences required for cell-type specific thyroid hormone regulation of rat growth hormone promoter activity. J. Biol. Chem. 261, 14373-14376.

Lebrun,C.J., Diehl,L.F., Abbott,K.C., Welch,P.G., and Yuan,C.M. (2000). Life expectancy-benefits of cancer screening in the end-stage renal disease population. Am. J. Kidney Dis. 35, 237-243.

Lee,S.H., Wang,W., Yajima,S., Jose,P.A., and Mouradian,M.M. (1997). Tissue-specific promoter usage in the D1A dopamine receptor gene in brain and kidney. DNA Cell Biol. 16, 1267-1275.

Lesbordes,J.C., Bordet,T., Haase,G., Castelnau-Ptakhine,L., Rouhani,S., Gilgenkrantz,H., and Kahn,A. (2002). In vivo electrotransfer of the cardiotrophin-1 gene into skeletal muscle slows down progression of motor neuron degeneration in pmn mice. Hum. Mol. Genet. 11, 1615-1625.

Levenson,V.V., Transue,E.D., and Roninson,I.B. (1998). Internal ribosomal entry site-containing retroviral vectors with green fluorescent protein and drug resistance markers. Hum. Gene Ther. 9, 1233-1236.

Li,C., Ke,S., Wu,Q.P., Tansey,W., Hunter,N., Buchmiller,L.M., Milas,L., Charnsangavej,C., and Wallace,S. (2000). Tumor irradiation enhances the tumor-specific distribution of poly(L-glutamic acid)-conjugated paclitaxel and its antitumor efficacy. Clin. Cancer Res. 6, 2829-2834.

Li,X., Eastman,E.M., Schwartz,R.J., and Draghia-Akli,R. (1999). Synthetic muscle promoters: activities exceeding naturally occurring regulatory sequences. nature biotechnology 17, 241-245.

Lin,H., Yutzey,K.E., and Konieczny,S.F. (1991). Muscle-specific expression of the troponin I gene requires interactions between helix-loop-helix muscle regulatory factors and ubiquitous transcription factors. Mol. Cell Biol. 11, 267-280.

Liu,Y., Li,H., Tanaka,K., Tsumaki,N., and Yamada,Y. (2000). Identification of an enhancer sequence within the first intron required for cartilage-specific transcription of the alpha2(XI) collagen gene. J. Biol. Chem. 275, 12712-12718.

Lucas,M.L., Heller,L., Coppola,D., and Heller,R. (2002). IL-12 plasmid delivery by in vivo electroporation for the successful treatment of established subcutaneous B16.F10 melanoma. Mol. Ther. 5, 668-675.

Lucas,M.L., Jaroszeski,M.J., Gilbert,R., and Heller,R. (2001). In vivo electroporation using an exponentially enhanced pulse: a new waveform. DNA Cell Biol. 20, 183-188.

Macejak,D.G. and Sarnow,P. (1991). Internal initiation of translation mediated by the 5' leader of a cellular mRNA. Nature 353, 90-94.

Madry,H., Reszka,R., Bohlender,J., and Wagner,J. (2001). Efficacy of cationic liposome-mediated gene transfer to mesangial cells in vitro and in vivo. J. Mol. Med. 79, 184-189.

Makis,A.C., Chaliasos,N., Hatzimichael,E.C., and Bourantas,K.L. (2001). Recombinant human erythropoietin therapy in a transfusion-dependent beta-thalassemia major patient. Ann. Hematol. 80, 492-495.

Matsubara,H., Gunji,Y., Maeda,T., Tasaki,K., Koide,Y., Asano,T., Ochiai,T., Sakiyama,S., and Tagawa,M. (2201). Electroporation-mediated transfer of cytokine genes into human esophageal tumors produces anti-tumor effects in mice. Anticancer Res. 21, 2501-2503.

Matsuo,A., Tooyama,I., Isobe,S., Oomura,Y., Akiguchi,I., Hanai,K., Kimura,J., and Kimura,H. (1994). Immunohistochemical localization in the rat brain of an epitope corresponding to the fibroblast growth factor receptor-1 Neuroscience 60, 49-66.

McNally,M.A., Lebkowski,J.S., Okarma,T.B., and Lerch,L.B. (1988). Optimizing electroporation parameters for a variety of human hematopoietic cell lines. Biotechniques 6, 882-886.

Miklavcic,D., Beravs,K., Semrov,D., Cemazar,M.,Demsar,F., and Sersa,G. (1998). The importance of electric field distribution for effective in vivo electroporation of tissues. Biophys. J 74, 2152-2158.

Miklavcic,D., Semrov,D., Mekid,H., and Mir,L.M. (2000). A validated model of in vivo electric field distribution in tissues for electrochemotherapy and for DNA electrotransfer for gene therapy. Biochem. Biophys. Acta 1523, 73-83.

Mirza,A.M., Ezzat,S., and Axelrad,A.A. (1997). Insulin-like growth factor binding protein-1 is elevated in patients with polycythemia vera and stimulates erythroid burst formation in vitro. Blood 89, 1862-1869.

Morley,J.E. (2001). Anorexia, body composition, and ageing. Curr. Opin. Clin. Nutr. Metab Care 4, 9-13.

Mumper,R.J., Wang,J., Klakamp,S.L., Nitta,H., Anwer,K., Tagliaferri,F., and Rolland,A.P. (1998). Protective interactive noncondensing (PINC) polymers for enhanced plasmid distribution and expression in rat skeletal muscle. J. Control Release 52, 191-203.

Nabel,E.G., Plautz,G., Boyce,F.M., Stanley,J.C., and Nabel,G.J. (1989). Recombinant gene expression in vivo within endothelial cells of the arterial wall. Science 244, 1342-1344.

Nairn,R.S., Adair,G.M., Porter,T., Pennington,S.L., Smith,D.G., Wilson,J.H., and Seidman,M.M. (1993). Targeting vector configuration and method of gene transfer influence targeted correction of the APRT gene in Chinese hamster ovary cells. Somat. Cell Mol. Genet. 19, 363-375.

Narum,D.L., Kumar,S., Rogers,W.O., Fuhrmann,S.R., Liang,H., Oakley,M., Taye,A., Sim,B.K., and Hoffman,S.L. (2001). Codon optimization of gene fragments encoding Plasmodium falciparum merzoite proteins enhances DNA vaccine protein expression and immunogenicity in mice. Infect. Immun. 69, 7250-7253.

Nelson,K.A. (2000) The cancer anorexia-cachexia syndrome. Semin. Oncol. 27, 64-68.

Nelson,K.A. (2001). Modern management of the cancer anorexia-cachexia syndrome. Curr. Pain Hedache Rep. 5, 250-256.

Neumann,E., Schaefer-Ridder,M., Wang,Y., and Hofschneider,P.H. (1982). Gene transfer into mouse lyoma cells by electroporation in high electric fields. EMBO J. 1, 841-845.

Nomoto,S., Tatematsu,Y., Takahashi,T., and Osada,H. (1999). Cloning and characterization of the alternative promoter regions of the human LIMK2 gene responsible for alternative transcripts with tissue-specific expression. Gene 236, 259-271.

Ohlsson,H., Thor,S., and Edlund,T. (1991). Novel insulin promoter- and enhancer-binding proteins that discriminate between pancreatic alpha- and beta-cells. Mol. Endocrinol. 5, 897-904.

Otani,Y., Tabata,Y., and Ikada,Y. (1996). Rapidly curable biological glue composed of gelatin and poly(L-glutamic acid). Biomaterials 17, 1387-1391.

Otani,Y., Tabata,Y., and Ikada,Y. (1998). Hemostatic capability of rapidly curable glues from gelatin, poly(L-glutamic acid), and carbodiimide. Biomaterials 19, 2091-2098.

Papassotiriou,I., Voskaridou,E., Stamoulakatou,A., and Loukopoulos,D. (2000). Increased erythropoietin level induced by hydroxyurea treatment of sickle cell patients. Hematol. J. 1, 295-300.

Payen,E., Bettan,M., Rouyer-Fessard,P., Beuzard,Y., and Scherman,D. (2001). Improvement of mouse beta-thalassemia by electrotransfer of erythropoietin cDNA. Exp. Hematol. 29, 295-300.

Pech,M., Rao,C.D., Robbins,K.C., and Aaronson,S.A. (1989). Functional identification of regulatory elements within the promoter region of platelet-derived growth factor 2. Mol. Cell Biol. 9, 396-405.

Pelletier,J. and Sonenberg,N. (1988). Internal initiation of translation of eukaryotic mRNA directed by a sequence derived from poliovirus RNA. Nature 334, 320-325.

Pinkert,C.A., Ornitz,D.M., Brinster,R.L., and Palmiter,R.D. (1987). An albumin enhancer located 10 kb upstream functions along with its promoter to direct efficient, liver-specific expression in transgenic mice. Genes Dev. 1, 268-276.

Potrykus,I., Paszkowski,J., Saul,M.W., Petruska,J., and Shillito,R.D. (1985). Molecular and general genetics of a hybrid foreign gene introduced into tobacco by direct gene transfer. Mol. Gen. Genet. 199, 169-177.

Potter,H., Weir,L., and Leder,P. (1984). Enhancer-dependent expression of human kappa immunoglobulin genes introduced into mouse pre-B lymphocytes by electroporation. Proc. Natl. Acad. Sci. U. S. A 81, 7161-7165.

Prahalada,S., Stabinski,L.G., Chen,H.Y., Morrissey,R.E., DE Burlet,G., Holder,D., Patrick,D.H., Peter,C.P., and Van Zwieten,M.J. (1998). Pharmacological and toxicological effects of chronic porcine growth hormone administration in dogs [see comments]. Toxicol. Pathol. 26, 185-200.

Prentice,H., Kloner,R.A., Prigozy,T., Christensen,T., Newman,L., Li,Y., and Kedes,L. (1994). Tissue restricted gene expression assayed by direct DNA injection into cardiac and skeletal muscle. Journal of Molecular & Cellular Cardiology 26, 1393-1401.

Raghavachari,N. and Fahl,W.E. (2002). Targeted gene delivery to skin cells in vivo comparative study of liposomes and polymers as delivery vehicles. J. Pharm. Sci. 91, 615-622.

Rippe,R.A., Brenner,D.A., and Leffert,H.L. (1990). DNA-mediated gene transfer into adult rat hepatocytes in primary culture. Mol. Cell Biol. 10, 689-695.

Robbins,K., McCabe,S., Scheiner,T., Strasser,J., Clark,R., and Jardieu,P. (1994). Immunological effects of insulin-like growth factor-I—enhancement of immunoglobulin synthesis. Clin. Exp. Immunol. 95, 337-342.

Satozawa,N., Takezawa,K., Miwa,T., Takahashi,S., Hayakawa,M., and Ooka,H. (2000). Differences in the effects of 20K- and 22 K-hGH on water retention in rats [In Process Citation]. Growth Horm. IGF. Res. 10, 187-192.

Smith,L.C. and Nordstrom,J.L. (2000). Advances in plasmid gene delivery and expression in skeletal muscle. Curr. Opin. Mol. Ther. 2, 150-154.

Sohmiya,M. and Kato,Y. (2000). Effect of long-term treatment with recombinant human growth hormone on erythropoietin secretion in an anemic patient with panhypopituitarism. J Endocrinol. Invest 23, 31-36.

Somiari,S., Glasspool-Malone,J., Drabick,J.J., Gilbert,R.A., Heller,R., Jaroszeski,M.J., and Malone,R.W. (2000). Theory and in vivo application of electroporative gene delivery. Mol. Ther. 2, 178-187.

Song,S., Embury,J., Laipis,P.J., Berns,K.I., Crawford,J.M., and Flotte,T.R. (2001). Stable therapeutic serum levels of human alpha-1 antitrypsin (AAT) after portal vein injection of recombinant adeno-associated virus (rAAV) vectors. Gene Ther. 8, 1299-1306.

Terada,Y., Tanaka,H., Okado,T., Inoshita,S., Kuwahara,M., Akiba,T., Sasaki,S., and Marumo,F. (2001). Efficient and ligand-dependent regulated erythropoietin production by naked dna injection and in vivo electroporation. Am. J Kidney Dis. 38, S50-S53.

Thorner,M.O., Forhman,L.A., Leong,D.A., Thominet,J., Downs,T., Hellmann,P., Chitwood,J., Vaughan,J.M., and Vale,W. (1984). Extrahypothalamic growth-hormone-releasing factor (GRF) secretion is a rare cause of acromegaly: plasma GRF levels in 177 acromegalic patients. Journal of Clinical Endocrinology & Metabolism 59, 846-849.

Thorner,M.O., Vance,M.L., Evans,W.S., et al., (1986). Clinical Studies with GHRH in Man. Hormone Research 24, 91-98.

Toneguzzo,F., Keating,A., Glynn,S., and McDonald,K. (1988). Electric field-mediated gene transfer: characterization of DNA transfer and patterns of integration in lymphoid cells. Nucleic Acids Res. 16, 5515-5532.

Tripathy,S.K., Svensson,E.C., Black,H.B., Goldwasser,E., Margalith,M., Hobart, PM, and Leiden,J.M. (1996). Long-term expression of erythropoietin in the systemic circulation of mice after intramuscular injection of a plasmid DNA vector. Proc. Natl. Acad. Sci. USA 93, 10876-10880.

Tronche,F., Rollier,A., Bach,I., Weiss,M.C., and Yaniv,M. (1989). The rat albumin promoter: cooperation with upstream elements is required when binding of APF/HNF1 to the proximal element is partially impaired by mutation or bacterial methylation. Mol. Cell Biol. 9, 4759-4766.

Tronche,F., Rollier,A., Herbomel,P., Bach,I., Cereghini,S., Weiss,M., and Yaniv,M. (1990). Anatomy of the rat albumin promoter. Mol. Biol. Med. 7, 173-185.

Trudel,M. and Costantini,F. (1987). A 3' enhancer contributes to the stage-specific expression of the human beta-globin gene. Genes Dev. 1, 954-961.

Tsumaki,N., Kimura,T., Tanaka,K., Kimura,J.H., Ochi,T., and Yamada,Y. (1998). Modular arrangement of cartilage- and neural tissue-specific cis elements in the mouse alpha2(XI) collagen promoter. J. Biol. Chem. 273, 22861-22864.

Tsunekawa,B., Wada,M., Ikeda,M., Uchida,H., Naito,N., and Honjo,M. (1999). The 20-kilodalton (kDa) human growth hormone (HGH) differs from the 22-kDa hGH in the effect on the human prolactin receptor. Endocrinology 140, 3909-3918.

Tsurumi,Y., Takeshita,S., Chen,D., Kearney,M., Rossow,S.T., Passeri,J., Horowitz,J.R., Symes,J.F., and Isner,J.M. (1996). Direct intramuscular gene transfer of naked DNA encoding vascular endothelial growth factor augments collateral development and tissue perfusion [see comments]. Circulation 94, 3281-3290.

Tur-Kaspa,R., Teicher,L., Levine,B.J., Skoultchi,A.I., and Shafritz,D.A. (1986). Use of electroporation to introduce biologically active foreign genes into primary rat hepatocytes. Mol. Cell Biol. 6, 716-718.

Urena,P., Bonnardeaux,A., Eckardt,K.U., Kurtz,A., and Drueke,T.B. (1992). Insulin-like growth factor I: a modulator of erythropoiesis in uraemic patients? Nephrol. Dial. Transplant. 7, 40-44.

Vance,M.L. (1990). Growth-hormone-releasing hormone. [Review] [52 refs]. Clinical Chemistry 36, 415-420.

Vance,M.L., Kaiser,D.L., Evans,W.S., Furlanetto,R., and et al., (1985). Pulsatile growth hormone secretion in normal man during a continuous 24-hour infusion of human growth hormone releasing factor (1-40). Evidence for intermittent somatostatin secretion. J. Clin. Invest. 75, 1584-1590.

Vansteenkiste,J., Pirker,R., Massuti,B., and et al., (2002). Double-blind, placebo-controlled, randomized phase III trial of darbepoetin alfa in lung cancer patients receiving chemotherapy. J. Natl. Cancer Inst. 94, 1211-1220.

Vegeto,E., Allan,G.F., Schrader,W.T., and et al., (1992). The mechanism of RU486 antagonism is dependent on the conformation of the carboxy-terminal tail of the human progesterone receptor. Cell 69, 703-713.

Verhelst,J., Abs,R., Vandeweghe,M., Mockel,J., et al., (1997). Two years of replacement therapy in adults with growth hormone deficiency. Clin. Endocrinol. (Oxf) 47, 485-494.

Vilquin,J.T., Kennel,P.F., Paturneau-Jouas,M., et al., (2001). Electrotransfer of naked DNA in the skeletal muscles of animal models of muscular dystrophies. Gene Ther. 8, 1097-1107.

Vittone,J., Blackman,M.R., and et al., (1997). Effects of single nightly injections of growth hormone-releasing hormone (GHRH 1-29) in healthy elderly men Metabolism: Clinical and Experimental 46, 89-96.

Wada,M., Uchida,H., Ikeda,M., Tsunekawa,B., and et al., (1998). The 20-kilodalton (kDa) human growth hormone (hGH) differs from the 22-kDa hGH in the complex formation with cell surface hGH receptor and hGH-binding protein circulating in human plasma. Mol. Endocrinol. 12, 146-156.

Weinroth,S.E., Parenti,D.M., and Simon,G.L. (1995). Wasting syndrome in AIDS: pathophysiologic mechanisms and therapeutic approaches. Infect. Agents Dis. 4, 76-94.

Wells,K.E., Maule,J., Kingston,R., Foster,K., and et al., (1997). Immune responses, not promoter inactivation, are responsible for decreased long-term expression following plasmid gene transfer into skeletal muscle.FEBS Lett. 407, 164-168.

Wiethoff,C.M., Smith,J.G., Koe,G.S., and Middaugh,C.R. (2001). The potential role of proteoglycans in cationic lipid-mediated gene delivery. Studies of the interaction of cationic lipid-DNA complexes with model glycosaminoglycans. J. Biol. Chem. 276, 32806-32813.

Wilson,J.M., Birinyi,L.K., Salomon,R.N., Libby,P., Callow,A.D., and Mulligan,R.C. (1989). Implantation of vascular grafts lined with genetically modifed endothelial cells. Science 244, 1344-1346.

Wolff,J.A., Malone,R.W., Williams,P., Chong,W., et al., (1990). Direct gene transfer into mouse muscle in vivo. Science 247, 1465-1468.

Wu,G.Y. and Wu,C.H. (1988b). Receptor-mediated gene dellivery and expression in vivo. J. Biol. Chem. 263, 14621-14624.

Wu,H.K., Squire,J.A., Song,Q., and Weksberg,R. (1997). Promoter-dependent tissue-specific expressive nature of imprinting gene, insulin-like growth factor II, in human tissues. Biochem. Biophys. Res. Commun. 233, 221-226.

Xie,T.D. and Tsong,T.Y. (1993). Study of mechanisms of electric field-induced DNA transfection. V. Effects of DNA topology on surface binding, cell uptake, expression, and integration into host chromosomes of DNA in the mammalian cell. Biophys. J. 65, 1684-1689.

Xu,J., Nawaz,Z., Tsai,S.Y., Tsai,M.J., and O'Malley,B.W. (1996). The extreme C terminus of progesterone receptor contains a transcriptional repressor domain that functions through a putative corepressor. Proc. Natl. Acad. Sci. USA 93, 12195-12199.

Yasui,A., Oda,K., Usunomiya,H., Kakudo,K., Suzuki,T., Yoshida,T., Park,H.M., Fukazawa,K., and Muramatsu,T. (2001). Elevated gastrin secretion by vivo gene electroporation in skeletal muscle. Int. J Mol. Med. 8, 489-494.

Yeh,S.S. and Schuster,M.W. (1999). Geriatric cachexia: the role of cytokines. Am. J Clin. Nutr. 70, 183-197.

Yin, D. and Tang,J.G. (2001). Gene therapy for streptozotocin-induced diabetic mice by electroporational transfer of naked human insulin precursor DNA into skeletal muscle in vivo. FEBS Lett. 495, 16-20.

Yorifuji,T. and Mikawa,H. (1990). Co-transfer of restriction endonucleases and plasmid DNA into mammalian cells by electroporation: effect on stable transformation. Mutat. Res. 243, 121-126.

Yutzey,K.E. and Konieczny,S.F. (1992). Different E-box regulatory sequences are functionally distinct when placed within the context of the troponin I enhancer. Nucleic Acids Res. 20, 5105-5113.

Zhao-Emonet,J.C., Boyer,O., Cohen,J.L., and Klatzmann,D. (1998). Deletional and mutational analyses of the human CD4 gene promoter: characterization of a minimal tissue-specific promoter. Biochem. Biophys. Acta 1442, 109-119.

Chappel, S., "Growth hormone in immune reconstitution," Journal of Acquired Immune Deficiency Syndromes and Human Retrovirology., Apr. 15, 1999, vol. 20, No. 5 pp. 423-431.

Christ, et al., "The importance of growth hormone in the regulation of erythropoiesis, red cell mass, and plasma volume in adults with growth hormone deficiency," Journal of Clinical Endocrinology and Metabolism,. 1997, vol. 82, No. 9, pp. 2985-2990.

Dorshkind, et al. "The roles of prolactin, growth hormone, insulin-like growth factor-l, and thyroid hormones in lymphocyte development and function: insights from genetic models of hormone and hormone receptor deficiency," Endocrine Reviews. 2000, vol. 21, No. 3, pp. 292-312.

Gesundheit, et al., "Endocrine therapy with recombinant hormones and growth factors.* Molecular Endocrinology: Basic Concepts and Clinical Correlations," Edited by B. D. Weintraub. New York: Raven Press, Ltd, 1995, pp. 491-507.

Pasqualini, et al., "Growth acceleration in children with chronic renal failure treated with growth-hormone-releasing hormone (GHRH)," Medicine (Buenos Aires). 1996, vol. 56, No. 3, pp. 241-246.

Schally, et al., "Hypothalemic hormones and cancer," Frontiers in Neuroendochrinology. Oct. 2001, vol. 22, No. 4, pp. 248-291.

Williams, et al., "Potential therapeutic indications for growth hormone and growth hormone-releasing hormone in conditions other than growth retardation," Pharmacotherapy. 1966, vol. 6, No. 6, pp. 311-318.

International Search Report Dated Jul. 16, 2003.

* cited by examiner

Figure 1

YADAIFTNSYRKVLGQLSARKLLQDIMSRQQGERNQEQGA-OH (SEQ ID No.: 10) porcine wild-type
HVDAIFTNSYRKVLAQLSARKLLQDILNRQQGERNQEQGA-OH (SEQ ID No.: 1) HV-GHRH
YIDAIFTNSYRKVLAQLSARKLLQDILNRQQGERNQEQGA-OH (SEQ ID No.: 2) TI-GHRH
YVDAIFTNSYRKVLAQLSARKLLQDILNRQQGERNQEQGA-OH (SEQ ID No.: 3) TV-GHRH
YADAIFTNSYRKVLAQLSARKLLQDILNRQQGERNQEQGA-OH (SEQ ID No.: 4) 15/27/28-GHRH

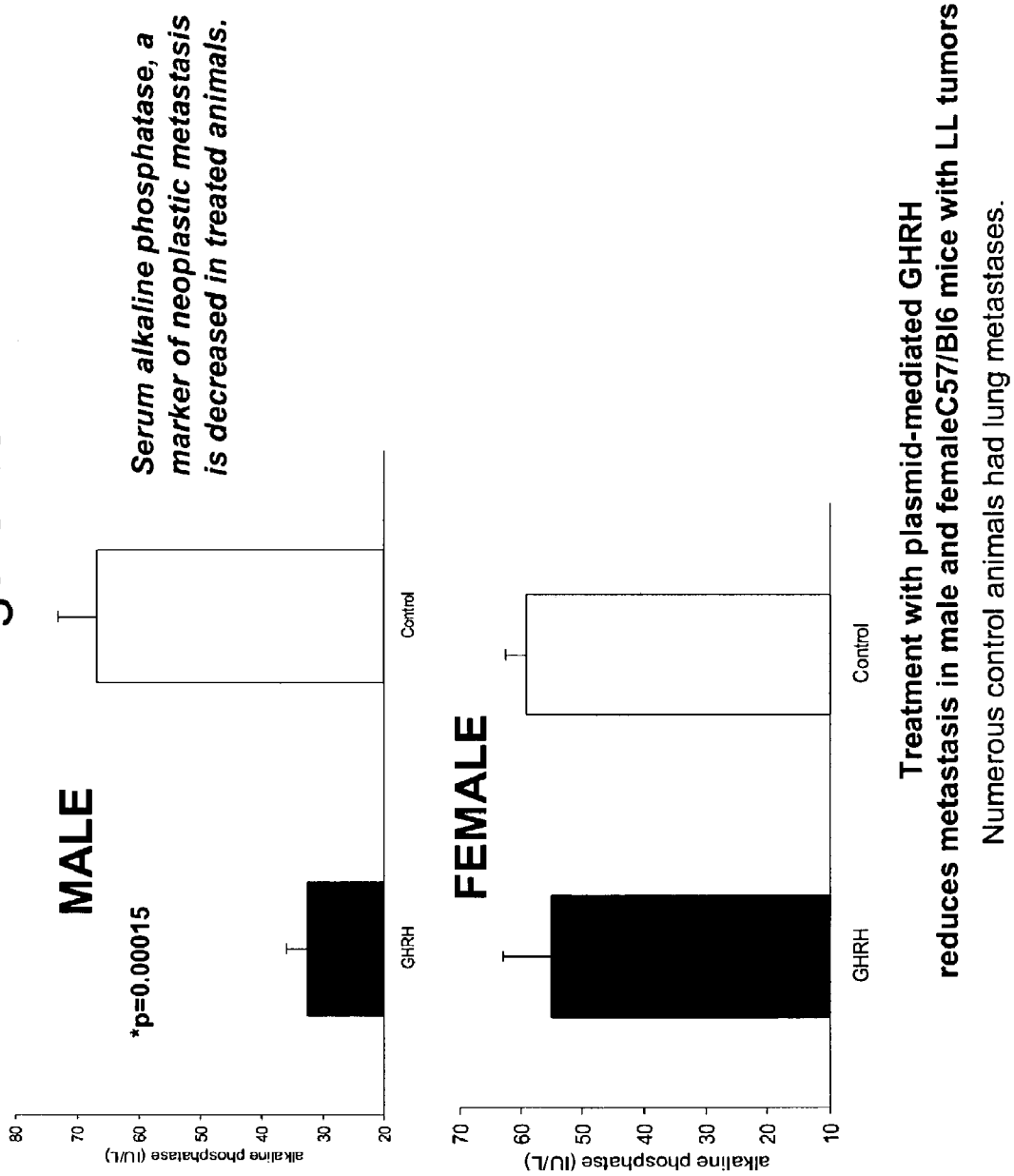

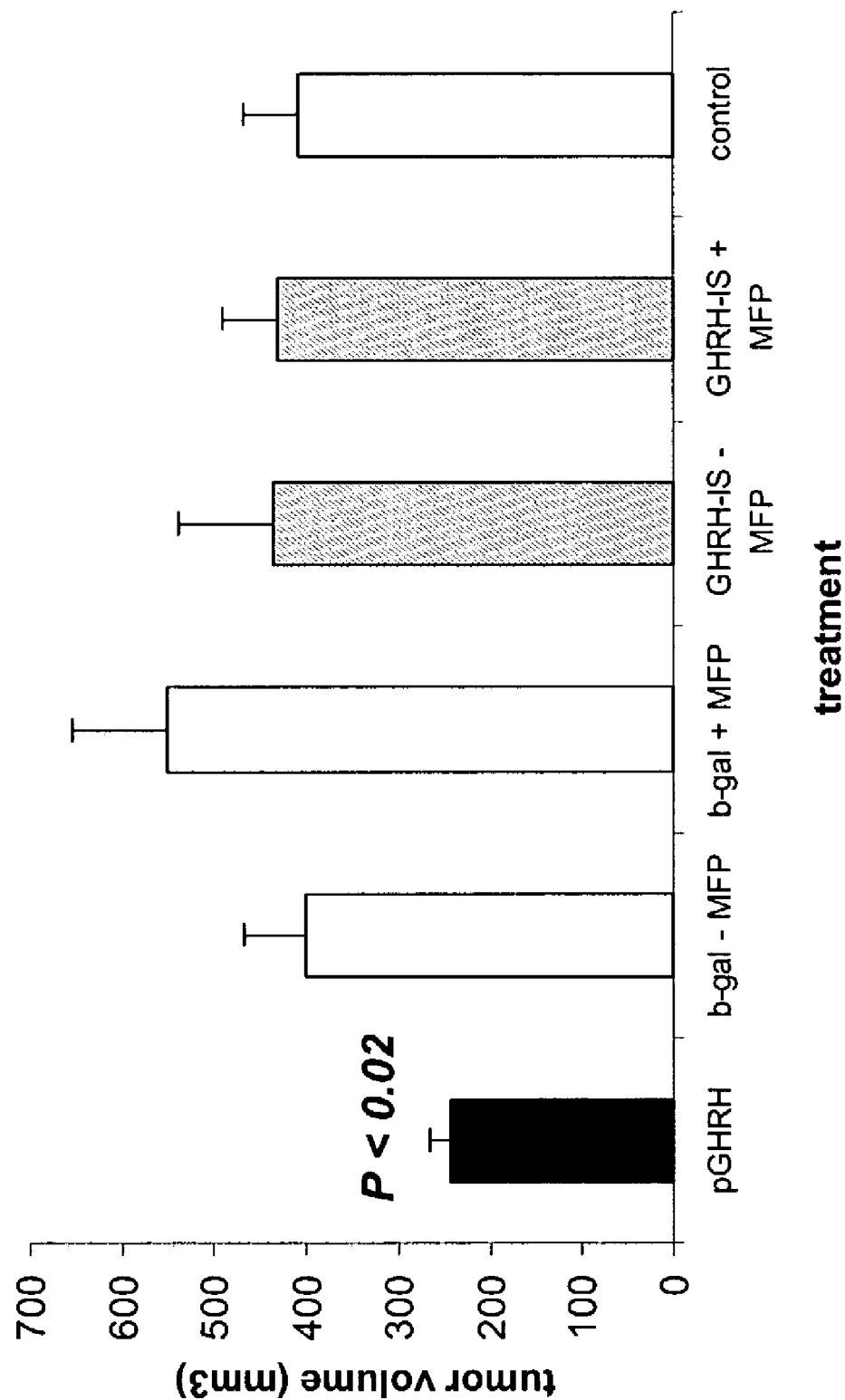

Figure 15 shows the protein metabolism at 56 days post-injection.

| Group I (controls) | | | | | | | | | | | | |
|---|---|---|---|---|---|---|---|---|---|---|---|---|
| 4 Dogs | AST (SGOT) | ALT (SGPT) | T. bilirubin | Alk Phos | GGT | Tot. Protein | Albumin | Globulin | A/G Ratio | Cholesterol | BUN | Creatinine |
| Average Value Pre-Injection | 19.75 | 27.75 | 0.10 | 43.25 | 7.00 | 6.25 | 3.43 | 2.83 | 1.28 | 164.25 | 11.75 | 0.73 |
| Average Value Post-Injection | 20.25 | 29.25 | 0.10 | 37.25 | 2.50 | 6.23 | 3.58 | 2.65 | 1.40 | 190.00 | 14.50 | 0.68 |
| Average Δ Value | 0.50 | 1.50 | 0.00 | -6.00 | -4.50 | -0.03 | 0.15 | -0.18 | 0.13 | 25.75 | 2.75 | -0.05 |
| % of Δ / average value | 2.53 | 5.41 | 0.00 | -13.87 | -64.29 | -0.40 | 4.38 | -6.19 | 9.80 | 15.68 | 23.40 | -6.90 |

| Group II (200 mcg) | | | | | | | | | | | | |
|---|---|---|---|---|---|---|---|---|---|---|---|---|
| 8 Dogs | AST (SGOT) | ALT (SGPT) | T. bilirubin | Alk Phos | GGT | Tot. Protein | Albumin | Globulin | A/G Ratio | Cholesterol | BUN | Creatinine |
| Average Value Pre-Injection | 25.50 | 31.75 | 0.10 | 32.88 | 5.75 | 6.21 | 3.38 | 2.84 | 1.26 | 161.75 | 9.88 | 0.63 |
| Average Value Post-Injection | 23.63 | 31.38 | 0.11 | 38.38 | 4.38 | 6.44 | 3.61 | 2.83 | 1.39 | 157.25 | 11.63 | 0.70 |
| Average Δ Value | -1.88 | -0.38 | 0.01 | 5.50 | -1.38 | 0.23 | 0.24 | -0.01 | 0.13 | -4.50 | 1.75 | 0.08 |
| % of Δ / average value | -7.35 | -1.18 | 12.50 | 16.73 | -23.91 | 3.62 | 7.04 | -0.44 | 9.90 | -2.78 | 17.72 | 12.00 |

| Group III (600 mcg) | | | | | | | | | | | | |
|---|---|---|---|---|---|---|---|---|---|---|---|---|
| 8 Dogs | AST (SGOT) | ALT (SGPT) | T. bilirubin | Alk Phos | GGT | Tot. Protein | Albumin | Globulin | A/G Ratio | Cholesterol | BUN | Creatinine |
| Average Value Pre-Injection | 24.14 | 29.43 | 0.10 | 33.00 | 4.75 | 6.15 | 3.43 | 2.73 | 1.29 | 172.63 | 11.88 | 0.70 |
| Average Value Post-Injection | 25.63 | 29.88 | 0.10 | 42.75 | 4.25 | 6.31 | 3.31 | 2.96 | 1.28 | 176.50 | 13.88 | 0.69 |
| Average Δ Value | 1.48 | 0.45 | 0.00 | 9.75 | -0.50 | 0.16 | -0.11 | 0.24 | -0.01 | 3.88 | 2.00 | -0.01 |
| % of Δ / average value | 6.14 | 1.52 | 0.00 | 29.55 | -10.53 | 2.64 | -3.28 | 8.72 | -0.97 | 2.24 | 16.84 | -1.79 |

| Group IV (1000 mcg) | | | | | | | | | | | | |
|---|---|---|---|---|---|---|---|---|---|---|---|---|
| 8 Dogs | AST (SGOT) | ALT (SGPT) | T. bilirubin | Alk Phos | GGT | Tot. Protein | Albumin | Globulin | A/G Ratio | Cholesterol | BUN | Creatinine |
| AVERAGE | 24.63 | 29.38 | 0.10 | 41.25 | 6.25 | 5.98 | 3.40 | 2.58 | 1.33 | 149.25 | 11.38 | 0.69 |
| Average Value Post-Injection | 24.75 | 32.25 | 0.14 | 45.88 | 3.88 | 5.88 | 3.58 | 2.30 | 1.58 | 158.25 | 13.13 | 0.73 |
| Average Δ Value | 0.13 | 2.88 | 0.04 | 4.63 | -2.38 | -0.10 | 0.18 | -0.28 | 0.25 | 9.00 | 1.75 | 0.04 |
| % of Δ / average value | 0.51 | 9.79 | 37.50 | 11.21 | -38.00 | -1.67 | 5.15 | -10.68 | 18.87 | 6.03 | 15.38 | 5.45 |

Figure 16 shows the blood values in dogs at 56 days post-injection

| Blood Values | Group 1 (control) 4 dogs | | | | Group 2 (200 mcg) 8 dogs | | | | Group 3 (600 mcg) 8 dogs | | | | Group 4 (1000 mcg) 8 dogs | | |
|---|---|---|---|---|---|---|---|---|---|---|---|---|---|---|---|
| | Ave Pre-Inj | Ave Post-Inj | Ave Δ | %Δ Ave | Ave Pre-Inj | Ave Post-Inj | Ave Δ | %Δ Ave | Ave Pre-Inj | Ave Post-Inj | Ave Δ | %Δ Ave | Ave Pre-Inj | Ave Post-Inj | Ave Δ |
| WBC | 10.88 | 9.78 | -1.10 | -10.1 | 10.56 | 9.90 | -0.66 | -6.3 | 10.50 | 13.38 | 2.88 | 27.4 | 10.63 | 11.25 | 0.63 |
| RBC | 6.63 | 7.60 | 0.98 | 14.7 | 6.50 | 7.56 | 1.06 | 16.3 | 6.81 | 7.30 | 0.49 | 7.2 | 7.03 | 7.39 | 0.36 |
| HGB | 14.90 | 16.65 | 1.75 | 11.7 | 14.20 | 17.04 | 2.84 | 20.0 | 15.10 | 16.08 | 0.98 | 6.5 | 15.63 | 16.91 | 1.29 |
| PCV | 47.50 | 53.50 | 6.00 | 12.6 | 45.38 | 52.88 | 7.50 | 16.5 | 48.25 | 51.00 | 2.75 | 5.7 | 50.13 | 52.25 | 2.13 |
| MCV | 72.25 | 70.75 | -1.50 | -2.1 | 69.75 | 70.13 | 0.38 | 0.5 | 70.63 | 69.75 | -0.88 | -1.2 | 71.13 | 70.75 | -0.38 |
| MCH | 22.53 | 22.03 | -0.50 | -2.2 | 21.91 | 22.56 | 0.65 | 3.0 | 22.13 | 21.90 | -0.23 | -1.0 | 22.23 | 22.91 | 0.69 |
| MCHC | 31.25 | 31.25 | 0.00 | 0.0 | 31.75 | 32.38 | 0.63 | 2.0 | 31.63 | 31.38 | -0.25 | -0.8 | 31.25 | 32.38 | 1.13 |
| N (%) | 69.25 | 60.75 | -8.50 | -12.3 | 66.75 | 62.88 | -3.88 | -5.8 | 61.63 | 65.63 | 4.00 | 6.5 | 58.00 | 62.25 | 4.25 |
| Lym (%) | 20.75 | 27.50 | 6.75 | 32.5 | 24.38 | 28.00 | 3.63 | 14.9 | 24.25 | 24.63 | 0.38 | 1.5 | 33.25 | 27.00 | -6.25 |
| Mono (%) | 4.75 | 4.75 | 0.00 | 0.0 | 4.75 | 3.75 | -1.00 | -21.1 | 5.50 | 4.63 | -0.88 | -15.9 | 3.75 | 3.50 | -0.25 |
| Eos (%) | 5.25 | 7.00 | 1.75 | 33.3 | 4.13 | 5.38 | 1.25 | 30.3 | 5.25 | 5.00 | -0.25 | -4.8 | 4.88 | 7.25 | 2.38 |
| Bas (%) | 0.00 | 0.00 | 0.00 | | 0.00 | 0.00 | 0.00 | | 0.00 | 0.00 | 0.00 | | 0.13 | 0.00 | -0.13 |
| D.BR | 0.00 | 0.00 | 0.00 | | 0.00 | 0.01 | 0.01 | | 0.00 | 0.01 | 0.01 | | 0.03 | 0.03 | 0.00 |
| LDH | 25.75 | 22.50 | -3.25 | -12.6 | 47.75 | 26.50 | -21.25 | -44.5 | 34.88 | 24.50 | -10.38 | -29.7 | 28.00 | 31.50 | 3.50 |
| rothrombin Time | 7.50 | 7.70 | 0.20 | 2.7 | 8.36 | 8.34 | -0.03 | -0.3 | 9.13 | 8.20 | -0.93 | -10.1 | 7.93 | 8.34 | 0.41 |
| Qnt Plat | 118.25 | 259.75 | 141.50 | 119.7 | 140.50 | 263.50 | 123.00 | 87.5 | 239.25 | 291.25 | 52.00 | 21.7 | 271.25 | 283.88 | 12.63 |
| Glucose | 123.00 | 110.75 | -12.25 | -10.0 | 114.25 | 108.88 | -5.38 | -4.7 | 119.50 | 112.13 | -7.38 | -6.2 | 113.50 | 109.63 | -3.88 |
| Amylase | 894.50 | 819.25 | -75.25 | -8.4 | 885.50 | 887.50 | 2.00 | 0.2 | 806.50 | 874.38 | 67.88 | 8.4 | 836.63 | 898.75 | 62.13 |
| Lipase | 218.50 | 213.00 | -5.50 | -2.5 | 198.00 | 224.88 | 26.88 | 13.6 | 315.50 | 262.38 | -53.13 | -16.8 | 217.00 | 223.13 | 6.13 |
| Na | 146.75 | 145.75 | -1.00 | -0.7 | 146.00 | 145.00 | -1.00 | -0.7 | 146.25 | 145.00 | -1.25 | -0.9 | 146.00 | 145.88 | -0.13 |
| K | 4.33 | 4.25 | -0.08 | -1.7 | 4.11 | 4.09 | -0.02 | -0.6 | 4.48 | 4.25 | -0.23 | -5.0 | 4.38 | 4.26 | -0.11 |
| Na/K Ratio | 34.25 | 34.75 | 0.50 | 1.5 | 35.63 | 35.50 | -0.13 | -0.4 | 32.75 | 34.25 | 1.50 | 4.6 | 33.50 | 34.25 | 0.75 |
| Cl- | 110.75 | 108.00 | -2.75 | -2.5 | 111.13 | 107.25 | -3.88 | -3.5 | 111.25 | 108.13 | -3.13 | -2.8 | 110.50 | 109.00 | -1.50 |
| CPK | 91.50 | 125.75 | 34.25 | 37.4 | 178.13 | 119.75 | -58.38 | -32.8 | 180.50 | 143.25 | -37.25 | -20.6 | 128.88 | 147.75 | 18.88 |
| TGR | 34.25 | 41.25 | 7.00 | 20.4 | 33.38 | 40.00 | 6.63 | 19.9 | 31.50 | 38.63 | 7.13 | 22.6 | 34.75 | 42.00 | 7.25 |
| Osmolality, Calc. | 304.50 | 302.75 | -1.75 | -0.6 | 301.88 | 300.13 | -1.75 | -0.6 | 303.25 | 301.38 | -1.88 | -0.6 | 302.38 | 302.63 | 0.25 |
| Corr. Ca | 10.00 | 10.15 | 0.15 | 1.5 | 10.03 | 10.70 | 0.67 | 6.6 | 10.00 | 10.38 | 0.38 | 3.8 | 9.93 | 10.25 | 0.32 |
| Mg | 1.48 | 1.48 | 0.00 | 0.0 | 1.56 | 1.50 | -0.06 | -4.0 | 1.50 | 1.46 | -0.04 | -2.5 | 1.51 | 1.41 | -0.10 |

Figure 17 shows the bone metabolism in dogs at 56 days post-injection.

| Group I (controls) | | | |
|---|---|---|---|
| 4 Dogs | Phosphorus | Calcium | Ca/PO4 Ratio |
| Average Value Pre-Injection | 4.25 | 9.83 | 2.33 |
| Average Value Post-Injection | 4.53 | 10.38 | 2.29 |
| Average Δ Value | 0.28 | 0.55 | -0.03 |
| % of Δ / average value | 6.47 | 5.60 | -1.38 |

| Group II (200 mcg) | | | |
|---|---|---|---|
| 8 Dogs | Phosphorus | Calcium | Ca/PO4 Ratio |
| Average Value Pre-Injection | 4.25 | 9.83 | 2.39 |
| Average Value Post-Injection | 4.14 | 10.40 | 2.51 |
| Average Δ Value | -0.11 | 0.58 | 0.13 |
| % of Δ / average value | -2.65 | 5.85 | 5.28 |

| Group III (600 mcg) | | | |
|---|---|---|---|
| 8 Dogs | Phosphorus | Calcium | Ca/PO4 Ratio |
| Average Value Pre-Injection | 4.44 | 10.05 | 2.29 |
| Average Value Post-Injection | 3.99 | 10.20 | 2.56 |
| Average Δ Value | -0.45 | 0.15 | 0.27 |
| % of Δ / average value | -10.14 | 1.49 | 11.82 |

| Group IV (1000 mcg) | | | |
|---|---|---|---|
| 8 Dogs | Phosphorus | Calcium | Ca/PO4 Ratio |
| AVERAGE | 4.83 | 9.91 | 2.11 |
| Average Value Post-Injection | 3.74 | 10.16 | 2.72 |
| Average Δ Value | -1.09 | 0.25 | 0.61 |
| % of Δ / average value | -22.54 | 2.52 | 28.71 |

Figure 18 shows a diagnosis specific therapy and survival for dogs

| Group | Treatment | | Drug | | Dose | # Dogs | Cancer Type | # Dogs | Days Survived |
|---|---|---|---|---|---|---|---|---|---|
| Controls | Radiation | | | | 80 Rads (26 visits) | 1 | Carcinoma | 1 | 254 |
| | Chemotherapy | | Vincristine | GC1 | 0.5-0.65 (mg/M²) | 1 | MCT | 1 | 182 |
| | | | Adriamycin | GC2 | 30 (mg/M²) | 1 | Sarcoma | 1 | 178 |
| | | | Carboplatin | GC3 | 90 (mg/M²) | 1 | Melanoma | 1 | 133* |
| | | | CCNU | GC4 | 65 (mg/M₂) | 1 | Lymphoma | 1 | 180 |
| | | | | GC5 | | | | | |
| | | | Vin/Cyt | GC6/GC7/GC8/GC9 | 0.4-0.7 / 200-300 (mg/M²) | 6 | Lymphoma | 4 | 104/104/104/189* |
| | | | | GC10 | | | Sarcoma | 1 | 167 |
| | | | | GC11 | | | Leukemia | 1 | 275 |
| | | | Vin/Adr | GC12 | 0.5-0.6 / 30 (mg/M²) | 1 | Sarcoma | 1 | 49* |
| | | | | GC13 | 0.5-0.6 / 30 (mg/M²) | 1 | Lymphoma | 1 | 130 |
| | | | Cyt/Adr | GC14 | ? / 30 (mg/M²) | 1 | Sarcoma | 1 | 171 |
| | | | Vin/Cyt/Adr | GC15 | 0.5-0.6 / 200 / 30 (mg/M²) | 2 | Lymphoma | 1 | 180 |
| | | | | GC16 | | | Sarcoma | 1 | 147* |
| | Rad./ Chemo. | | Vincristine/ CCNU | GC17 | 0.5-0.6 / 60 (mg/M²) 80 Rads (18 visits) | 1 | MCT | 1 | 178* |
| | | | Adriamycin | GC18 | 15-30 (mg/M²) 80 Rads (19 visits) | 1 | Sarcoma | 1 | 106 |
| | | | Carboplatin | GC19 | 90 (mg/M²) 80 Rads (6 visits) | 1 | Melanoma | 1 | 258 |
| Experimental | Radiation | | | GE1/GE2 | 80 Rads (6-21 visits) | 6 | Sarcoma | 2 | 167 - 167 |
| | | | | GE3 | | | MCT | 1 | 251 |
| | | | | GE4 | | | Adenoma | 1 | 251 |
| | | | | GE5/GE6 | | | Solid Tumor | 2 | 174 -- 124* |
| | Chemotherapy | | Cytoxin | GE7 | 350 (mg/M²) | 1 | None "Lung Nodules" | 72* | |
| | | | Vin/Cyt/Adr/Car | GE8 | 0.75 / 300 / 15-30 / 200 (mg/M²) | 1 | Sarcoma | 1 | 167 |
| | Rad./ Chemo. | | Vin/Cyt/Adr | GE9 | 0.6-0.7 / 200-300 / 30 (mg/M²) 80 Rads (2-3 visits) | 1 | Lymphoma | 1 | 67* |
| | | | Vin/Cyt | GE10 | 0.6 / 200 (mg/M²) 80 Rads (3 visits) | 1 | Adenoma | 1 | 83 |
| | Surgical Removal | | | GE11 | | 1 | Solid Tumor | 1 | 97 |

Figure 19 shows the blood values for dogs with cancer.

| Experimental - injected dogs | WBC/HPF | RBC/HPF | HGB | PCV (%) | MCV | MCH | MCHC | Neutrophils | Lymphs (%) | Monos (%) | EOS (%) | Basophils |
|---|---|---|---|---|---|---|---|---|---|---|---|---|
| Average Value Pre-Injection | 7.97 | 5.64 | 13.29 | 38.29 | 67.86 | 23.50 | 34.86 | 78.00 | 13.00 | 7.43 | 1.67 | 1.00 |
| Average Value Post-Injection | 7.04 | 6.59 | 15.11 | 43.88 | 66.75 | 23.01 | 34.50 | 77.13 | 15.38 | 5.63 | 2.60 | 1.00 |
| Average Δ Value | -1.89 | 1.03 | 2.06 | 6.29 | -0.86 | -0.41 | -0.29 | -1.71 | 3.71 | -1.86 | 0.67 | 0.00 |
| % of Δ / average value | -23.66 | 18.23 | 15.48 | 16.42 | -1.26 | -1.76 | -0.82 | -2.20 | 28.57 | -25.00 | 40.00 | 0.00 |
| TTEST | 0.04 | 0.01 | 0.02 | 0.02 | 0.77 | 0.27 | 0.05 | 0.21 | 0.35 | 0.29 | 0.98 | |

| Controls - non-injected dogs | WBC/HPF | RBC/HPF | HGB | PCV (%) | MCV | MCH | MCHC | Neutrophils | Lymphs (%) | Monos (%) | EOS (%) | Basophils |
|---|---|---|---|---|---|---|---|---|---|---|---|---|
| Average Value | 12.72 | 5.72 | 13.26 | 38.00 | 66.40 | 23.36 | 35.22 | 71.91 | 18.80 | 6.91 | 2.76 | 0.32 |
| Average Δ Value | -1.40 | -0.46 | -0.91 | -1.92 | -0.08 | 0.17 | 0.44 | -3.70 | 3.43 | 0.58 | 0.16 | 0.04 |
| % of Δ / average value | -11.02 | -8.10 | -6.82 | -5.06 | -0.12 | 0.74 | 1.24 | -5.15 | 18.24 | 8.33 | 5.92 | 10.89 |

Figure 20 shows the blood values for old healthy dogs

| Gulf Coast-Non-cancer/Experimental | | | | | | | | | | |
|---|---|---|---|---|---|---|---|---|---|---|
| 4 Dogs | RBC | HGB | WBC | Lymphocy | T. Protein | Albumin | Globulin | A/G Ratio | Cholesterol |
| Average Value Pre-Injection | 6.53 | 15.90 | 8.55 | 18.50 | 6.30 | 3.50 | 2.80 | 1.28 | 247.00 |
| Average Value Post-Injection | 6.73 | 16.33 | 8.80 | 14.50 | 6.50 | 3.40 | 3.10 | 1.10 | 264.75 |
| Δ Value | 0.20 | 0.42 | 0.25 | -4.00 | 0.20 | -0.10 | 0.30 | -0.18 | 17.75 |
| % of Δ / average value | 0.03 | 0.03 | 0.03 | -0.28 | 0.03 | -0.03 | 0.10 | -0.16 | 0.07 |

| Gulf Coast-Non-cancer/Experimental | | | | | | | |
|---|---|---|---|---|---|---|---|
| 4 Dogs | BUN | Creatinine | BUN/Creat | Phosphor | Calcium | Ca/PO4 Ra | Glucose |
| Average Value Pre-Inj | 13.25 | 0.73 | 19.50 | 4.20 | 10.65 | 2.54 | 110.00 |
| Average Value Post-Inj | 12.00 | 0.83 | 14.50 | 3.73 | 10.78 | 2.89 | 104.25 |
| Δ Value | -1.25 | 0.10 | -5.00 | -0.48 | 0.13 | 0.13 | -5.75 |
| % of Δ / average value | -0.10 | 0.12 | -0.34 | -0.13 | 0.01 | 0.04 | -0.06 |

TREATING ANEMIA IN SUBJECTS BY ADMINISTRATION OF PLASMIDS ENCODING GROWTH HORMONE RELEASING HORMONE

RELATED APPLICATIONS

This application claims priority to U.S. Provisional Patent Application Ser. No. 60/339,610 entitled "Plasmid Mediated Treatment for Anemia, Wasting, Immune Dysfunction and Life Extension for the Chronically Ill," filed on Dec. 11, 2001, the entire content of which is hereby incorporated by reference.

BACKGROUND

The present invention pertains to compositions and methods for plasmid-mediated supplementation. The present invention pertains to compositions and methods that are useful for retarding the growth rate of abnormal cells, tumor progression reduction, prevention of kidney failure, reduction in metastasis, increased survival and other conditions commonly associated with cancer-bearing animals. Some embodiments of the invention can be accomplished by delivering an effective amount of a nucleic acid expression construct that encodes a GHRH or functional biological equivalent thereof into a tissue of a subject and allowing expression of the encoded gene in the subject. For example, when such a nucleic acid sequence is delivered into the specific cells of the subject tissue specific constitutive expression is achieved. Furthermore, external regulation of the GHRH or functional biological equivalent thereof gene can be accomplished by utilizing inducible promoters that are regulated by molecular switch molecules, which are given to the subject. The preferred method to deliver the constitutive or inducible nucleic acid encoding sequences of GHRH or the functional biological equivalents thereof is directly into the cells of the subject by the process of in vivo electroporation. In addition, a treatment for retarding tumor growth, and retarding cachexia or the wasting effects that are commonly associated with tumors is achieved by the delivery of recombinant GHRH or biological equivalent into the subject. Anemia, wasting, tumor growth, immune dysfunction, kidney failure, cancer, decreased life expectancy, and other conditions can be related to a specific cancer, tumor, disease or the effects of a disease treatment. This invention relates to a plasmid-mediated supplementation for:
1) treating anemia in a subject;
2) increasing total red blood cell mass in a subject;
3) decreasing tumor growth in a tumor bearing individual;
4) preventing or reversing the wasting of a subject;
5) reversing abnormal weight loss in a subject;
6) treating immune dysfunction;
7) preventing the onset of kidney failure
8) preventing the onset and/or development of metastasis
9) reversing the suppression of lymphopoesis in a subject; and/or
10) extending life expectancy and increasing survival for the chronically ill subject.

The present invention pertains to compositions and methods that are useful for retarding the growth rate of abnormal cells, tumor progression reduction, prevention of kidney failure, reduction of metastasis, and increased survival in cancer-bearing animals. Overall, the embodiments of the invention can be accomplished by delivering an effective amount of a nucleic acid expression construct that encodes a GHRH or functional biological equivalent thereof into a tissue of a subject and allowing expression of the encoded gene in the subject. For example, when such a nucleic acid sequence is delivered into the specific cells of the subject tissue specific constitutive expression is achieved. Furthermore, external regulation of the GHRH or functional biological equivalent thereof gene can be accomplished by utilizing inducible promoters that are regulated by molecular switch molecules, which are given to the subject. The preferred method to deliver the constitutive or inducible nucleic acid encoding sequences of GHRH or the functional biological equivalents thereof is directly into the cells of the subject by the process of in vivo electroporation. In addition, a treatment for retarding the growth of abnormal cells and tumor growth is achieved by the delivery of recombinant GHRH or biological equivalent into the subject. Anemia, wasting, tumor growth, immune dysfunction, kidney failure, cancer, decreased life expectancy, and other conditions also can be related to a specific cancer, tumor, disease or the effects of a disease treatment GHRH could be also delivered directly, as protein, by intravenous, subcutaneous or intranasal administration or through a slow release pump.

Anemia: Anemia refers to a condition in which there is a reduction of the number or volume of red blood corpuscles or of the total amount of hemoglobin in the bloodstream, resulting in paleness, generalized weakness, etc. of the subject. The production of red blood cells in mammals is known as erythropoiesis. Erythropoiesis is primarily controlled by erythropoietin ("EPO"), an acidic glycoprotein. The EPO stimulates the production of new erythrocytes to replace those lost to the aging process. Additionally, EPO production is stimulated under conditions of hypoxia, wherein the oxygen supply to the tissues is reduced below normal physiological levels despite adequate perfusion of the tissue by blood. Hypoxia may be caused by hemorrhaging, radiation-induced erythrocyte destruction, various anemia's, high altitude, or long periods of unconsciousness. In response to tissues undergoing hypoxic stress, EPO will increase red blood cell production by stimulating the conversion of primitive precursor cells in the bone marrow into proerythroblasts that subsequently mature, synthesize hemoglobin and are released into the circulation as red blood cells.

EPO is normally present in low concentrations in plasma, where it is sufficient to maintain equilibrium between normal blood cell loss (i.e., through aging) and red blood cell production. Anemia is a decrease in red blood cell mass caused by decreased production or increased destruction of red blood cells. EPO supplementation is currently used for treatment of the anemia's associated with different diseases, as end-stage renal failure (Cremagnani et al., 1993; Diez et al., 1996) and acquired immunodeficiency syndrome ("AIDS") (Sowade et al., 1998), particularly in subjects who are being treated with zidovudine ("AZT"). EPO is also used for amelioration of the anemia associated with cancer chemotherapy (Vansteenkiste et al., 2002).

Another group of anemic disorders, each of which results from an inherited abnormality in globin production, is termed the hemoglobinopathies. Hemoglobinopathies include a spectrum of disorders that can be classified broadly into two types. The first types are those that result from an inherited structural alteration in one of the globin chains, for example sickle cell anemia. These disorders give rise to the production of abnormal hemoglobin molecules (Papassotiriou et al., 2000). The second major subdivision of hemoglobinopathies, the thalassemias, results from inherited defects in the rate of synthesis of one or more of the globin chains. This causes ineffective erythropoiesis, hemolysis, and varying degrees of anemia due to the inadequate production of red blood cells. Accordingly, EPO can be used in the treatment of anemia's, for example, hemoglobinopathies that are characterized by low or defective red blood cell production and/or increased red blood cell destruction (Makis et al., 2001; Payen et al., 2001).

Additional prior art has indicated that anemic patients with panhypopituitarism, a condition in which hemoglobin ("Hb") concentration remained as low as 11.0 g/dl in spite of appropriate replacement with thyroid and adrenocortical hormones, were treated with recombinant human growth hormone ("GH") and EPO levels were increased (Sohmiya and Kato, 2000). Recombinant human GH was constantly infused subcutaneously for 12 months, which caused the plasma erythropoietin ("EPO") levels to nearly double, with a concomitant increase of Hb concentration. When the administration of human GH was interrupted, both plasma EPO levels and Hb concentrations decreased. There was a close correlation between plasma GH and EPO levels before and during the human GH administration. Plasma GH levels were well correlated with Hb concentrations before and during human GH administration. Plasma IGF-I levels were also correlated with Hb concentrations, but not with plasma EPO levels.

U.S. Pat. Nos. 5,846,528 ("the '528 patent") and 6,274,158 ("the '158 patent") teach that conditions of anemia can be treated by deliberately increasing erythropoietin ("EPO"). In addition, the '528 patent teaches the use of recombinant adeno-associated virus ("AAV") virions for delivery of DNA molecules encoding EPO to muscle cells and tissue in the treatment of anemia. The '528 patent shows a direct in vivo injection of recombinant AAV virions into muscle tissue (e.g., by intramuscular injection), and in vitro transduction of muscle cells that can be subsequently introduced into a subject for treatment. Thus, a sustained high-level expression of a delivered nucleotide sequence encoding erythropoietin results, whereby in vivo secretion from transduced muscle cells allows systemic delivery. The '158 patent teaches the use of the subcutaneous, intravenous or oral administration of recombinant human EPO as a hemostatic agent for the treatment or prevention of bleeding from any organ or body part involved with benign or malignant lesions, surgical traumatic, non-healing/difficult to treat lesions, or radiation injury.

In brief, anemia can be caused by a specific disease, environmental factors, or the effects of a disease treatment. As discussed, circulating levels of EPO can be increased directly (e.g. injections of recombinant EPO) or indirectly (e.g. injections of recombinant GH). Although not wanting to be bound by theory, the related art suggests that anemic conditions can be successfully treated by methods or compounds capable of increasing the circulating levels of EPO. However, a skilled artisan recognizes that biological systems are immeasurably complex, and the ability to accurately predict what methods or compounds will elicit a specific biological response is outside the realm of a skilled artesian. Only through diligent laboratory experiments can insight to compounds or methods to treat anemia be discovered.

Wasting: Wasting of a subject can be defined as decreased body weight of at least 5-10% of the minimum ideal weight of the individual that is characterized by significant loss of both adipose tissue and muscle mass, which makes weight gain especially difficult for patients with a progressive disease (e.g. cancer, AIDS etc.). Wasting or cachexia is a classic clinical phenomenon that evokes historical images of sickbeds and patients with "consumption." It simply means "poor condition" in Greek. Accelerated loss of skeletal muscle can occur in setting of cancer, AIDS, or tuberculosis, as well as other chronic conditions (Barber et al., 1999; Weinroth et al., 1995). Weight loss is the most obvious manifestation of wasting associated with cancer (Nelson, 2000). Other clinical manifestations include anorexia, muscle wasting, and/or loss of adipose tissue and fatigue, which results in poor performance status (Davis and Dickerson, 2000). Because weight loss, tumor histology, and a poor performance status lead to a poor prognosis, wasting can become the direct cause of death. In contrast to simple starvation, the weight loss cannot be adequately treated with aggressive feeding. The weight loss therefore cannot be attributed entirely to poor intake, but is also a result of increased basal energy expenditure.

Wasting is present in more than one half of ambulatory cancer patients, and represents a serious problem when treating chronically ill patients. Although not wanting to be bound by theory, cytokine release and/or activation and liberation of several tumor derived substances is postulated to be responsible for the wasting syndrome. The related art teaches that many agents have been evaluated for treatment of wasting, with only modest benefit obtained from progestational agents (Barber et al., 1999; Nelson, 2001). In contrast, recombinant growth hormone ("GH"), insulin-like growth factor-I ("IGF-I") and IGF binding protein 3 ("IGFBP-3") therapies are effective in producing a benefit in cancer cachexia (Bartlett et al., 1994). Thus, the related art suggests that wasting may be treated by methods or compounds that increase the circulating levels of GH, IGF-I or IGFBP-3. Unfortunately, the complexity of biological systems makes it impossible to accurately predict what methods or compounds will elicit a specific biological response. Thus, only through meticulous laboratory experiments can an insight to useful compounds or methods to treat wasting be elucidated by one skilled in the art.

Cancer and tumor growth: Cancer is one of the leading causes of morbidity and mortality in the US and around the world. The average annual incidence rate for cancer increased in the last 20 years, to reach 475 to 100,000 in 1999. Due to population growth and aging, the number of cancer patient is expected to double from 1.3 million to 2.6 million between 2000 and 2050. In addition, the number and proportion of older persons with cancer are expected to increase dramatically: from 389,000 persons aged 75 years and older with newly diagnosed malignancies in 2000, to 1,102,000 persons in 2050, an increase from 30% to 42% of the cancer population (Edwards et al., 2002). Cancer in elderly has a poor prognosis due to complicating factors as anorexia of aging, alterations in the gastrointestinal system, the effect of elevated leptin levels, especially in men, and a variety of changes in central nervous system neurotransmitters. Body mass declines after the age of about 70 years old. This includes both loss of adipose tissue and muscle mass. The loss of muscle mass in older individuals is termed sarcopenia. Illness results in an increase of cytokines that produce both anorexia and cause protein wasting. Many of the causes of cachexia in older individuals are treatable (Morley, 2001; Yeh and Schuster, 1999). Tumor growth is accelerated by increases in cytokines and other pathological changes in cancer patients, but correction of cachexia, anemia, improvement of immune function and a positive nitrogen balance can decrease tumor growth and its complications (Demetri, 2001; Koo et al., 2001). Thus, a therapy that would address most of these complications could be of important benefit for patients.

Kidney failure: The predicted increase in the number of people with kidney failure and end-stage renal disease places an enormous burden on healthcare providers system (Hostetter and Lising, 2002). In order to reduce this burden, strategies must be implemented to improve the detection of kidney disease, and preventative measures must be targeted at those at greatest risk of disease (Crook et al., 2002). Important risk factors include hypertension, diabetes, obesity and cancer (Al Suwaidi et al., 2002; Nampoory et al., 2002). Serum creatinine, proteinuria, and microalbuminuria as early detection markers of disease are important, but treatments that could delay or prevent kidney failure could be of significant benefit for patients and the medical system (LeBrun et al., 2000; Sakhuja et al., 2000).

Growth Hormone ("GH") and Immune Function: The central role of growth hormone ("GH") is controlling somatic growth in humans and other vertebrates, and the physiologically relevant pathways regulating GH secretion from the pituitary is well known. The GH production pathway is composed of a series of interdependent genes whose products are required for normal growth. The GH pathway genes include: (1) ligands, such as GH and insulin-like growth factor-I ("IGF-I"); (2) transcription factors such as prophet of pit 1, or prop 1, and pit 1: (3) agonists and antagonists, such as growth hormone releasing hormone ("GHRH") and somatostatin ("SS"), respectively; and (4) receptors, such as GHRH receptor ("GHRH-R") and the GH receptor ("GH-R"). These genes are expressed in different organs and tissues, including the hypothalamus, pituitary, liver, and bone. Effective and regulated expression of the GH pathway is essential for optimal linear growth, as well as homeostasis of carbohydrate, protein, and fat metabolism GH synthesis and secretion from the anterior pituitary is stimulated by GHRH and inhibited by somatostatin, both hypothalamic hormones. GH increases production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

The immune function is modulated by IGF-I, which has two major effects on B cell development: potentiation and maturation, and as a B-cell proliferation cofactor that works together with interlukin-7 ("IL-7"). These activities were identified through the use of anti-IGF-I antibodies, antisense sequences to IGF-I, and the use of recombinant IGF-I to substitute for the activity. There is evidence that macrophages are a rich source of IGF-I. The treatment of mice with recombinant IGF-I confirmed these observations as it increased the number of pre-B and mature B cells in bone marrow (Jardieu et al., 1994). The mature B cell remained sensitive to IGF-I as immunoglobulin production was also stimulated by IGF-I in vitro and in vivo (Robbins et al., 1994).

The production of recombinant proteins in the last 2 decades provided a useful tool for the treatment of many diverse conditions. For example, GH-deficiencies in short stature children, anabolic agent in burn, sepsis, and AIDS patients. However, resistance to GH action has been reported in malnutrition and infection. Long-term studies on transgenic animals and in patients undergoing GH therapies have shown no correlation in between GH or IGF-I therapy and cancer development. GH replacement therapy is widely used clinically, with beneficial effects, but therapy is associated several disadvantages: GH must be administered subcutaneously or intramuscularly once a day to three times a week for months, or usually years; insulin resistance and impaired glucose tolerance; accelerated bone epiphysis growth and closure in pediatric patients (Blethen and MacGillivray, 1997; Blethen and Rundle, 1996).

In contrast, essentially no side effects have been reported for recombinant GHRH therapies. Extracranially secreted GHRH, as mature peptide or truncated molecules (as seen with pancreatic islet cell tumors and variously located carcinoids) are often biologically active and can even produce acromegaly (Esch et al., 1982; Thorner et al., 1984). Administration of recombinant GHRH to GH-deficient children or adult humans augments IGF-I levels, increases GH secretion proportionally to the GHRH dose, yet still invokes a response to bolus doses of recombinant GHRH (Bercu et al., 1997). Thus, GHRH administration represents a more physiological alternative of increasing subnormal GH and IGF-I levels (Corpas et al., 1993).

GH is released in a distinctive pulsatile pattern that has profound importance for its biological activity (Argente et al., 1996). Secretion of GH is stimulated by the GHRH, and inhibited by somatostatin, and both hypothalamic hormones (Thorner et al., 1995). GH pulses are a result of GHRH secretion that is associated with a diminution or withdrawal of somatostatin secretion. In addition, the pulse generator mechanism is timed by GH-negative feedback. The endogenous rhythm of GH secretion becomes entrained to the imposed rhythm of exogenous GH administration. Effective and regulated expression of the GH and insulin-like growth factor-I ("IGF-I") pathway is essential for optimal linear growth, homeostasis of carbohydrate, protein, and fat metabolism, and for providing a positive nitrogen balance (Murray and Shalet, 2000). Numerous studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies (Dubreuil et al., 1990; Vance, 1990; Vance et al., 1985). Although recombinant GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, GHRH administration is not practical.

Wild type GHRH has a relatively short half-life in the circulatory system, both in humans (Frohman et al., 1984) and in farm animals. After 60 minutes of incubation in plasma 95% of the GHRH(1-44)NH2 is degraded, while incubation of the shorter (1-40)OH form of the hormone, under similar conditions, shows only a 77% degradation of the peptide after 60 minutes of incubation (Frohman et al., 1989). Incorporation of cDNA coding for a particular protease-resistant GHRH analog in a therapeutic nucleic acid vector results in a molecule with a longer half-life in serum, increased potency, and provides greater GH release in plasmid-injected animals (Draghia-Akli et al., 1999), herein incorporated by reference). Mutagenesis via amino acid replacement of protease sensitive amino acids prolongs the serum half-life of the GHRH molecule. Furthermore, the enhancement of biological activity of GHRH is achieved by using super-active analogs that may increase its binding affinity to specific receptors (Draghia-Akli et al., 1999).

Extracranially secreted GHRH, as processed protein species GHRH(1-40) hydroxy or GHRH(1-44) amide or even as shorter truncated molecules, are biological active (Thorner et al., 1984). It has been reported that a low level of GHRH (100 pg/ml) in the blood supply stimulates GH secretion (Corpas et al., 1993). Direct plasmid DNA gene transfer is currently the basis of many emerging nucleic acid therapy strategies and thus does not require viral genes or lipid particles (Aihara and Miyazaki, 1998; Muramatsu et al., 2001). Skeletal muscle is target tissue, because muscle fiber has a long life span and can be transduced by circular DNA plasmids that express over months or years in an immunocompetent host (Davis et al., 1993; Tripathy et al., 1996). Previous reports demonstrated that human GHRH cDNA could be delivered to muscle by an injectable myogenic expression vector in mice where it transiently stimulated GH secretion to a modes extent over a period of two weeks (Draghia-Akli et al., 1997).

Administering novel GHRH analog proteins (U.S. Pat. Nos. 5,847,066; 5846,936; 5,792,747; 5,776,901; 5,696,089; 5,486,505; 5,137,872; 5,084,442, 5,036,045; 5,023,322; 4,839,344; 4,410,512, RE33,699) or synthetic or naturally occurring peptide fragments of GHRH (U.S. Pat. Nos. 4,833,166; 4,228,158; 4,228,156; 4,226,857; 4,224,316; 4,223,021; 4,223,020; 4,223, 019) for the purpose of increasing release of growth hormone have been reported. A GHRH analog containing the following mutations have been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. patent application Ser. No. 09/624,268 ("the '268 patent application"), which teaches application of a GHRH analog containing mutations that improve the ability to elicit the release of growth hormone. In addition, the '268 patent application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference.

U.S. Pat. No. 5,061,690 is directed toward increasing both birth weight and milk production by supplying to pregnant female mammals an effective amount of human GHRH or one of it analogs for 10-20 days. Application of the analogs lasts only throughout the lactation period. However, multiple administrations are presented, and there is no disclosure regarding administration of the growth hormone releasing hormone (or factor) as a DNA molecule, such as with plasmid mediated therapeutic techniques.

U.S. Pat. Nos. 5,134,120 ("the '120 patent") and 5,292,721 ("the '721 patent") teach that by deliberately increasing growth hormone in swine during the last 2 weeks of pregnancy through a 3 week lactation resulted in the newborn piglets having marked enhancement of the ability to maintain plasma concentrations of glucose and free fatty acids when fasted after birth. In addition, the 120 and 721 patents teach that treatment of the sow during lactation results in increased milk fat in the colostrum and an increased milk yield. These effects are important in enhancing survivability of newborn pigs and weight gain prior to weaning. However the 120 and 721 patents provide no teachings regarding administration of the growth hormone releasing hormone as a DNA form.

Gene Delivery and in vivo Expression: Recently, the delivery of specific genes to somatic tissue in a manner that can correct inborn or acquired deficiencies and imbalances was proved to be possible (Herzog et al., 2001; Song et al., 2001; Vilquin et al., 2001). Gene-based drug delivery offers a number of advantages over the administration of recombinant proteins. These advantages include the conservation of native protein structure, improved biological activity, avoidance of systemic toxicities, and avoidance of infectious and toxic impurities. In addition, nucleic acid vector therapy allows for prolonged exposure to the protein in the therapeutic range, because the newly secreted protein is present continuously in the blood circulation. In a few cases, the relatively low expression levels achieved after simple plasmid injection, are sufficient to reach physiologically acceptable levels of bioactivity of secreted peptides (Danko and Wolff, 1994; Tsurumi et al., 1996).

The primary limitation of using recombinant protein is the limited availability of protein after each administration. Nucleic acid vector therapy using injectable DNA plasmid vectors overcomes this, because a single injection into the patient's skeletal muscle permits physiologic expression for extensive periods of time (WO 99/05300 and WO 01/06988). Injection of the vectors promotes the production of enzymes and hormones in animals in a manner that more closely mimics the natural process. Furthermore, among the non-viral techniques for gene transfer in vivo, the direct injection of plasmid DNA into muscle tissue is simple, inexpensive, and safe.

In a plasmid-based expression system, a non-viral gene vector may be composed of a synthetic gene delivery system in addition to the nucleic acid encoding a therapeutic gene product. In this way, the risks associated with the use of most viral vectors can be avoided. The non-viral expression vector products generally have low toxicity due to the use of "species-specific" components for gene delivery, which minimizes the risks of immunogenicity generally associated with viral vectors. Additionally, no integration of plasmid sequences into host chromosomes has been reported in vivo to date, so that this type of nucleic acid vector therapy should neither activate oncogenes nor inactivate tumor suppressor genes. As episomal systems residing outside the chromosomes, plasmids have defined pharmacokinetics and elimination profiles, leading to a finite duration of gene expression in target tissues.

Efforts have been made to enhance the delivery of plasmid DNA to cells by physical means including electroporation, sonoporation, and pressure. Administration by electroporation involves the application of a pulsed electric field to create transient pores in the cellular membrane without causing permanent damage to the cell. It thereby allows for the introduction of exogenous molecules (Smith and Nordstrom, 2000). By adjusting the electrical pulse generated by an electroporetic system, nucleic acid molecules can travel through passageways or pores in the cell that are created during the procedure. U.S. Pat. No. 5,704,908 describes an electroporation apparatus for delivering molecules to cells at a selected location within a cavity in the body of a patient. These pulse voltage injection devices are also described in U.S. Pat. No. 5,439,440 and 5,702,304, and PCT WO 96/12520, 96/12006, 95/19805, and 97/07826.

Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Our previous studies using growth hormone releasing hormone ("GHRH") showed that plasmid therapy with electroporation is scalable and represents a promising approach to induce production and regulated secretion of proteins in large animals and humans (Draghia-Akli et al., 1999; Draghia-Akli et al., 2002).

The ability of electroporation to enhance plasmid uptake into the skeletal muscle has been well documented, as described above. In addition, plasmid formulated with poly-L-glutamate ("PLG") or polyvinylpyrolidone (PVP) has been observed to increase plasmid transfection and consequently expression of the desired transgene. The anionic polymer sodium PLG could enhance plasmid uptake at low plasmid concentrations, while reducing any possible tissue damage caused by the procedure. The ability of electroporation to enhance plasmid uptake into the skeletal muscle has been well documented, as previously described. PLG is a stable compound and resistant to relatively high temperatures (Dolnik et al., 1993). PLG has been previously used to increase stability in vaccine preparations (Matsuo et al., 1994) without increasing their immunogenicity. It also has been used as an anti-toxin post-antigen inhalation or exposure to ozone (Fryer and Jacoby, 1993). In addition, plasmid formulated with PLG or polyvinylpyrrolidone (PVP) has been observed to increase gene transfection and consequently gene expression to up to 10 fold in the skeletal muscle of mice, rats and dogs (Fewell et al., 2001; Mumper et al., 1998). PLG has been used to increase stability of anti-cancer drugs (Li et al., 2000) and as "glue" to close wounds or to prevent bleeding from tissues during wound and tissue repair (Otani et al., 1996; Otani et al., 1998).

Although not wanting to be bound by theory, PLG will increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, process that substantially increases the transfection efficiency. Furthermore, PLG will prevent the muscle damage associated with in vivo plasmid delivery (Draghia-Akli et al., 2002a) and will increase plasmid stability in vitro prior to injection.

The use of directly injectable DNA plasmid vectors has been limited in the past. The inefficient DNA uptake into muscle fibers after simple direct injection has led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996).

Although there are references in the art directed to electroporation of eukaryotic cells with linear DNA (McNally et al., 1988; Neumann et al., 1982) (Toneguzzo et al., 1988) (Aratani et al., 1992; Naim et al., 1993; Xie and Tsong, 1993; Yorifuji and Mikawa, 1990), these examples illustrate transfection into cell suspensions, cell cultures, and the like, and the transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

U.S. Pat. Nos. 5,874,534 ("the '534 patent") and U.S. Pat. No. 5,935,934 ("the '934 patent") describe mutated steroid receptors, methods for their use and a molecular switch for nucleic acid vector therapy, the entire content of each is hereby incorporated by reference. A molecular switch for regulating expression in nucleic acid vector therapy and methods of employing the molecular switch in humans, animals, transgenic animals and plants (e.g. GeneSwitch®) are described in the '534 patent and the '934 patent. The molecular switch is described as a method for regulating expression of a heterologous nucleic acid cassette for nucleic acid vector therapy and is comprised of a modified steroid receptor that includes a natural steroid receptor DNA binding domain attached to a modified ligand binding domain. The modified binding domain usually binds only non-natural ligands, anti-hormones or non-native ligands. One skilled in the art readily recognizes natural ligands do not readily bind the modified ligand-binding domain and consequently have very little, if any, influence on the regulation or expression of the gene contained in the nucleic acid cassette.

In summary, treatments for conditions such as anemia, wasting and immune dysfunction are uneconomical and restricted in scope. The related art has shown that it is possible to treat these different disease conditions in a limited capacity utilizing recombinant protein technology, but these treatments have some significant drawbacks. It has also been taught that nucleic acid expression constructs that encode recombinant proteins are viable solutions to the problems of frequent injections and high cost of traditional recombinant therapy. The introduction of point mutations into the encoded recombinant proteins was a significant step forward in producing proteins that are more stable in vivo than the wild type counterparts. Unfortunately, each amino acid alteration in a given recombinant protein must be evaluated individually, because the related art does not teach one skilled in the art to accurately predict how changes in structure (e.g. amino-acid sequences) will lead to changed functions (e.g. increased or decreased stability) of a recombinant protein. Therefore, the beneficial effects of nucleic acid expression constructs that encode expressed proteins can only be ascertained through direct experimentation. There is a need in the art to expanded treatments for subjects with a disease by utilizing nucleic acid expression constructs that are delivered into a subject and express stable therapeutic proteins in vivo.

SUMMARY OF THE INVENTION

The present invention pertains to compositions and methods that are useful for retarding the growth of abnormal cells, tumor progression reduction, prevention of kidney failure, reduction of metastasis, and increased survival in cancer-bearing animals. The method of this invention comprises treating a subject with plasmid mediated gene supplementation. The method comprises delivering an effective amount of a nucleic acid expression construct that encodes a growth-hormone-releasing-hormone ("GHRH") or functional biological equivalent thereof into a tissue, such as a muscle, of the subject. Specific embodiments of this invention are directed toward various types of tumors, such as adenoma; carcinoma; leukemia; lymphoma; lung tumor; mast cell tumor; melanoma; sarcoma; and solid tumors. The subsequent in vivo expression of the GHRH or biological equivalent in the subject is sufficient to retard tumor growth, prevent kidney failure and increase survival in cancer-bearing animals. It is also possible to enhance this method by placing a plurality of electrodes in a selected tissue, then delivering nucleic acid expression construct to the selected tissue in an area that interposes the plurality of electrodes, and applying a cell-transfecting pulse to the selected tissue in an area of the selected tissue where the nucleic acid expression construct was delivered. Electroporation, direct injection, gene gun, or gold particle bombardment are also used in specific embodiments to deliver the nucleic acid expression construct encoding the GHRH or biological equivalent into the subject. The subject in this invention comprises mammals, such as a humans, and domesticated animals.

The composition of this invention comprises an effective amount of a nucleic acid expression construct that encodes a growth-hormone-releasing-hormone ("GHRH") or functional biological equivalent thereof, wherein delivering and subsequent expression of the GHRH or biological equivalent in a tissue of the subject is sufficient to retard tumor growth and retard cachexia or the wasting effects that are commonly associated with tumor growth. Specific elements of the nucleic acid expression construct of this invention are also described. For example, the construct comprises a tissue specific promoter; a GHRH or functional biological equivalent; and a 3' untranslated region ("3"UTR") that are operatively linked. The nucleic acid expression construct of this invention comprises a construct that is substantially free of a viral backbone. Specific examples of a nucleic acid expression constructs used for this invention are also presented. The encoded functional biological equivalent of GHRH comprises a polypeptide having similar or improved biological activity when compared to the GHRH polypeptide. The GHRH or functional biological equivalent that is encoded by the nucleic acid expression construct and useful for this invention comprises an amino acid structure with a general sequence as follows:

wherein the formula has the following characteristics: $X_1$ is a D-or L-isomer of the amino acid tyrosine ("Y"), or histidine ("H"); $X_2$ is a D-or L-isomer of the amino acid alanine ("A"), valine ("V"), or isoleucine ("I"); $X_3$ is a D-or L-isomer of the amino acid alanine ("A") or glycine ("G"); $X_4$ is a D-or L-isomer of the amino acid methionine ("M"), or leucine ("L"); $X_5$ is a D-or L-isomer of the amino acid serine ("S") or asparagine ("N"); or a combination thereof. Specific examples of amino acid sequences for GHRH or functional biological equivalents that are useful for this invention are presented. In a specific embodiment, the encoded GHRH or functional biological equivalent thereof facilitates growth hormone ("GH") secretion in a subject that has received the nucleic acid expression construct. In specific embodiments of the invention, a transfection-facilitating polypeptide that increase the tissues ability to uptake the nucleic acid expression construct comprises a charged polypeptide, such as poly-L-glutamate.

One embodiment of the present invention pertains to a plasmid mediated supplementation method for treating anemia; increasing total red blood cell mass in a subject; reversing the wasting; reversing abnormal weight loss; treating immune dysfunction; reversing the suppression of lymphopoesis; or extending life expectancy for the chronically ill subject. This can be achieved utilizing an effective amount of a nucleic acid expression construct that contains both a constitutive promoter and an encoding sequence for growth hormone releasing hormone ("GHRH") or biological equivalent thereof. When this nucleic acid sequence is delivered into the specific cells of the subject (e.g. somatic cells, stem cells, or germ cells), tissue specific and constitutive expression of GHRH is achieved. The preferred method to deliver the nucleic acid sequence with the constitutive promoter and the encoding sequence of GHRH or the biological equivalent thereof is directly into the cells of the subject by the process of in vivo electroporation. Electroporation may involve externally supplied electrodes, or in the case of needles, internally supplied electrodes to aid in the inclusion of desired nucleotide sequences into the cells of a subject while the cells are within a tissue of the subject.

A further embodiment of the present invention pertains to pertains to a plasmid mediated method for the treatment of anemia, wasting, immune dysfunction and life extension for the chronically ill subject by utilizing the ability to regulate the expression of GHRH or biological equivalent thereof. Regulation is achieved by delivering into the cells of the subject a first nucleic acid sequence, and a second nucleic acid sequence, followed by a molecular switch; where the first nucleic acid sequence contains an inducible-promoter with a coding region for a growth-hormone-releasing-hormone ("inducible-GHRH") or an biological equivalent thereof and the second nucleic acid sequence has a constitutive promoter with a coding region for an inactive regulator protein. By delivering a molecular switch molecule (e.g. mifepistone) into the subject, the inactive regulator protein becomes active and initiates transcription of the inducible-GHRH in the subject. The external regulation, expression and ensuing release of GHRH or biological equivalent thereof by the modified-cells within the subject will the conditions of anemia, wasting, immune dysfunction and life extension for the chronically ill subject. The delivery of the nucleic acid sequences that allow external regulation of GHRH or the biological equivalent thereof directly into the cells of the subject can be accomplished by the process of in vivo electroporation.

A further embodiment of the present invention pertains to a method of treatment for anemia, wasting, immune dysfunction and life extension for the chronically ill subject by utilizing therapy that introduces specific recombinant GHRH-biological equivalent protein into the subject.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the amino acid sequence of GHRH or biological equivalent thereof.

FIG. 13 shows that the markers associtaed with metastasis development are increased in control animals versus GHRH-treated animals, and that the histopathology report showed considerably more metastasis in the control animals than in treated once.

FIG. 14 shows that tumor growth did not increase in nude mice treated with plasmid-mediated growth hormone releasing hormone (constitutively active pGHRH or regulated Gene Switch system GHRH-IS+/−MFP). NCI—human lung adenocarcinoma cell line. Animals treated with the constitutively active GHRH had smaller tumors than controls ($p<0.02$) at 33 days post-treatment. No other group displayed significant differences when compared to controls.

FIG. 15 shows the protein metabolism in dogs at 56 days post-injection.

FIG. 16 shows the blood values in dogs at 56 days post-injection.

FIG. 17 shows the bone metabolism in dogs at 56 days post-injection.

FIG. 18 shows the diagnosis, specific therapy chart and survival for dogs with spontaneous cancer.

FIG. 19 shows the blood values for dogs with cancer.

FIG. 20 shows the blood values for old healthy dogs.

DETAILED DESCRIPTION OF PREFERRED EMBODIMENTS

Definitions

Figure 2:
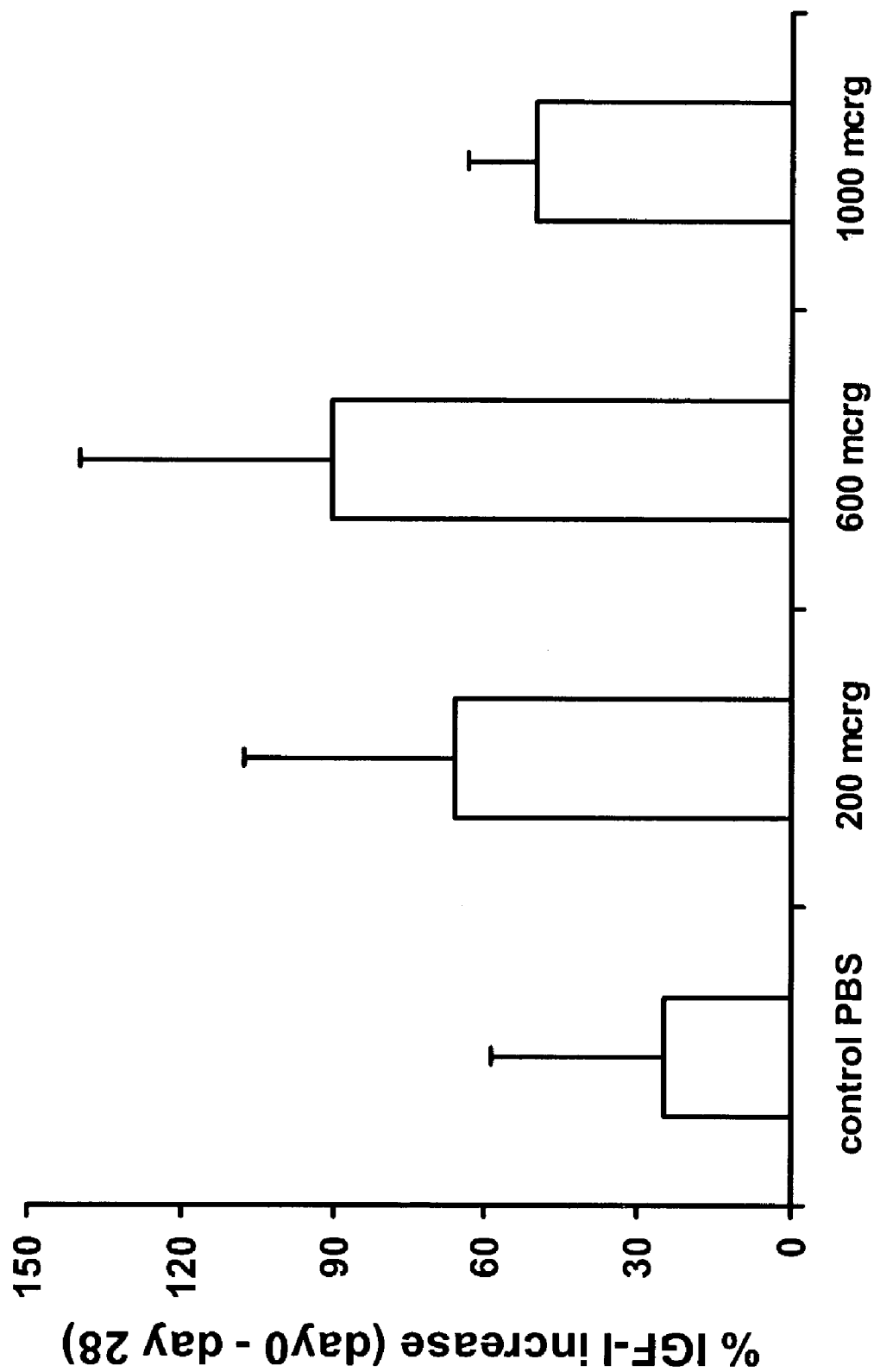
FIG. 2 shows the increase in the percentage of IGF-I levels in healthy dogs that were injected with different concentrations of the pSP-HV-GHRH plasmid.
Figure 3:
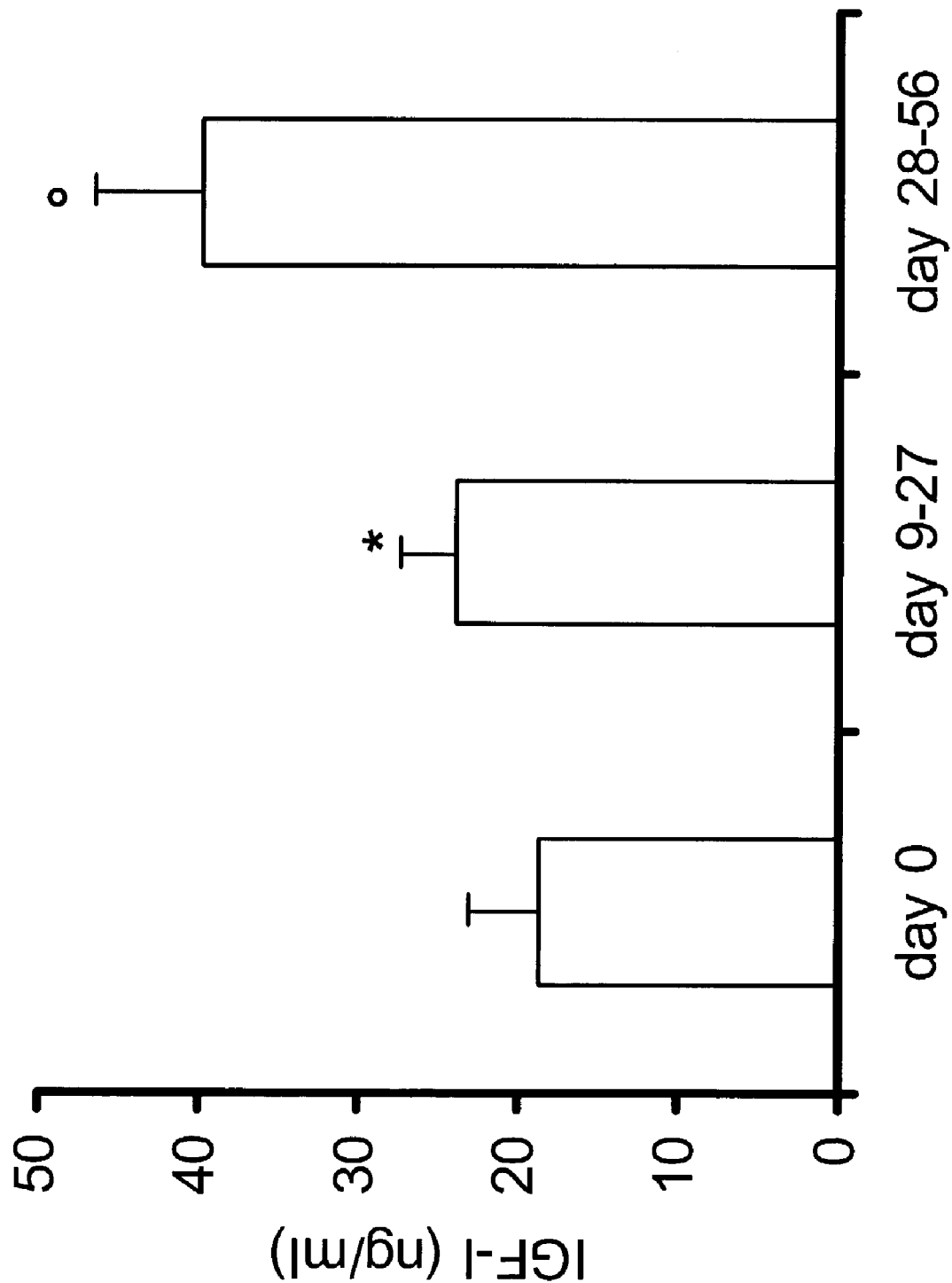
FIG. 3 shows the increase in the percentage of IGF-I levels at 9-27 and 28-56 days post-injection in dogs with cancer that were injected at day 0 with 100 mcg/kg to a total of no more than 1000 mcg of the pSP-HV-GHRH plasmid.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "abnormal weight loss," as used herein is defined as decreased body weight of at least 5-10% of the minimum ideal weight of the individual that is characterized by significant loss of both adipose tissue and muscle mass.

The term "AIDS therapy" as used herein refers to treatment of acquired immune deficiency syndrome ("AIDS") by any medical or physical means, including, but not limited to: antiretrovirals, nucleoside analogues, non-nucleoside reverse transcriptase inhibitors (NNRTIs), protease inhibitors, and/or other drugs used to boost the immune system.

The term "analog" as used herein includes any mutant of GHRH, or synthetic or naturally occurring peptide fragments of GHRH, such as HV-GHRH (SEQ ID NO: 1). TI-GHRH (SEQ ID NO: 2). TV-GHRH (SEQ ID NO: 3), 15127/28-GHRH (SEQ ID NO: 4), (1-44)NH2 (SEQ ID NO: 5). OR (1-40)OH (SEQ ID NO: 6) forms, or any shorter form to no less than (1-29) amino acids.

The term "anemia" as used herein refers to a condition in which there is a reduction of the number and/or volume of red blood corpuscles or of the total amount of hemoglobin in the bloodstream, resulting in paleness, generalized weakness, etc., of the subject.

The term "antiviral therapy" as used herein refers to a group of drugs that are of three main types, including: nucleoside analog drugs, protease (proteinase) inhibitor drugs, and non-nucleoside reverse-transcriptase inhibitor drugs (NNRTIs).

The term "bodily fat proportion" as used herein is defined as the body fat mass divided by the total body weight.

The term "cancer therapy" as used herein refers to treatment of cancer by any medical or physical means, including, but not limited to surgery, immunotherapy, chemotherapy, radiation therapy, hyperthermia and/or photodynamic therapy.

The term "cachexia" as used herein is defined as the accelerated loss of skeletal muscle.

The term "cassette" as used herein is defined as one or more transgene expression vectors.

The term "cell-transfecting pulse" as used herein is defined as a transmission of a force which results in transfection of a vector, such as a linear DNA fragment, into a cell. In some embodiments, the force is from electricity, as in electroporation, or the force is from vascular pressure.

The term "chronically ill" as used herein is defined as patients with conditions as chronic obstructive pulmonary disease, chronic heart failure, stroke, dementia, rehabilitation after hip fracture, chronic renal failure, rheumatoid arthritis, and multiple disorders in the elderly, with doctor visits and/or hospitalization once a month for at least two years.

The term "coding region" as used herein refers to any portion of the DNA sequence that is transcribed into messenger RNA (mRNA) and then translated into a sequence of amino acids characteristic of a specific polypeptide.

The term "coding region" as used herein refers to any portion of the DNA sequence that is transcribed into messenger RNA (mRNA) and then translated into a sequence of amino acids characteristic of a specific polypeptide.

The term "delivery" or "delivering" as used herein is defined as a means of introducing a material into a tissue, a subject, a cell or any recipient, by means of chemical or biological process, injection, mixing, electroporation, sonoporation, or combination thereof, either under or without pressure.

The term "DNA fragment" or "nucleic acid expression construct" as used herein refers to a substantially double stranded DNA molecule. Although the fragment may be generated by any standard molecular biology means known in the art, in some embodiments the DNA fragment or expression construct is generated by restriction digestion of a parent DNA molecule. The terms "expression vector," "expression cassette," or "expression plasmid" can also be used interchangeably. Although the parent molecule may be any standard molecular biology DNA reagent, in some embodiments the parent DNA molecule is a plasmid.

The term "donor-subject" as used herein refers to any species of the animal kingdom wherein cells have been removed and maintained in a viable state for any period of time outside the subject.

The term "donor-cells" as used herein refers to any cells that have been removed and maintained in a viable state for any period of time outside the donor-subject.

The term "effective amount" as used herein refers to sufficient nucleic acid expression construct or encoded protein administered to humans, animals or into tissue culture to produce the adequate levels of protein, RNA, or hormone. One skilled in the art recognizes that the adequate level of protein or RNA will depend on the use of the particular nucleic acid expression construct. These levels will be different depending on the type of administration and treatment or vaccination.

The term "electroporation" as used herein refers to a method that utilized electric pulses to deliver a nucleic acid sequence into cells.

The terms "electrical pulse" and "electroporation" as used herein refer to the administration of an electrical current to a tissue or cell for the purpose of taking up a nucleic acid molecule into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded GHRH" as used herein is a biologically active polypeptide of growth hormone releasing hormone.

The term "functional biological equivalent" of GHRH as used herein is a polypeptide that has a distinct amino acid sequence from a wild type GHRH polypeptide while simultaneously having similar or improved biological activity when compared to the GHRH polypeptide. The functional biological equivalent may be naturally occurring or it may be modified by an individual. A skilled artisan recognizes that the similar or improved biological activity as used herein refers to facilitating and/or releasing growth hormone or other pituitary hormones. A skilled artisan recognizes that in some embodiments the encoded functional biological equivalent of GHRH is a polypeptide that has been engineered to contain a distinct amino acid sequence while simultaneously having similar or improved biological activity when compared to the GHRH polypeptide. Methods known in the art to engineer such a sequence include site-directed mutagenesis.

The term "growth hormone releasing hormone" ("GHRH") as used herein is defined as a hormone that facilitates or stimulates release of growth hormone, and in a lesser extent other pituitary hormones, as prolactin.

The term "growth hormone" ("GH") as used herein is defined as a hormone that relates to growth and acts as a chemical messenger to exert its action on a target cell.

The term "GeneSwitch®" (a registered trademark of Valentis, Inc.; Burlingame, Calif.) as used herein refers to the technology of a mifepristone-inducible heterologous nucleic acid sequences encoding regulator proteins, GHRH, biological equivalent or combination thereof. Such a technology is schematically diagramed in FIG. 1 and FIG. 9. A skilled artisan recognizes that antiprogesterone agent alternatives to mifepristone are available, including onapristone, ZK112993, ZK98734, and 5α pregnane-3,2-dione.

The term "growth hormone" ("GH") as used herein is defined as a hormone that relates to growth and acts as a chemical messenger to exert its action on a target cell. In a specific embodiment, the growth hormone is released by the action of growth hormone releasing hormone.

The term "growth hormone releasing hormone" ("GHRH") as used herein is defined as a hormone that facilitates or stimulates release of growth hormone, and in a lesser extent other pituitary hormones, such as prolactin.

The term "heterologous nucleic acid sequence" as used herein is defined as a DNA sequence comprising differing regulatory and expression elements.

The term "immune dysfunction" as used herein refers to the abnormal, impaired, or incomplete functioning of a subject's immune system, as determined indirectly or directly by immune specific markers (e.g. IGF-I levels, or % lymphocytes).

The term "immunotherapy" as used herein refers to any treatment that promotes or enhances the body's immune system to build protective antibodies that will reduce the symptoms of a medical condition and/or lessen the need for medications.

The term "lean body mass" ("LBM") as used herein is defined as the mass of the body of an animal attributed to non-fat tissue such as muscle.

The term "life extension for the chronically ill" as used herein refers to an increase in the actual life expectancy for a subject that undertakes the treatment compared to a subject that did not have treatment.

The term "lymphopoiesis" as used herein is defined as the production of lymphocytes.

The term "kidney failure" as used herein is defined as the abrupt or chronic decline in glomerular filtration rate resulting from ischemic or toxic injury to the kidney, and includes a decrease of glomerular capillary permeability, back-leak of glomerular filtrate, tubular obstruction, and intrarenal vasoconstriction.

The term "modified cells" as used herein is defined as the cells from a subject that have an additional nucleic acid sequence introduced into the cell.

The term "modified-donor-cells" as used herein refers to any donor-cells that have had a GHRH-encoding nucleic acid sequence delivered.

The term "molecular switch" as used herein refers to a molecule that is delivered into a subject that can regulate transcription of a gene.

The term "nucleic acid expression construct" as used herein refers to any type of genetic construct comprising a nucleic acid coding for a RNA capable of being transcribed.

The term "expression vector" can also be used interchangeably herein. In specific embodiments, the nucleic acid expression construct comprises: a promoter; a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "poly-L-glutamate ("PLG")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette that contains heterologous nucleic acid sequence encoding GHRH or a biological equivalent thereof into the cells of the subject and allowing expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid mediated gene supplementation" as used herein refers a method to allow a subject to have prolonged exposure to a therapeutic range of a therapeutic protein by utilizing an effective amount of a nucleic acid expression construct in vivo.

The term "pulse voltage device," or "pulse voltage injection device" as used herein relates to an apparatus that is capable of causing or causes uptake of nucleic acid molecules into the cells of an organism by emitting a localized pulse of electricity to the cells. The cell membrane then destabilizes, forming passageways or pores. Conventional devices of this type are calibrated to allow one to select or adjust the desired voltage amplitude and the duration of the pulsed voltage. The primary importance of a pulse voltage device is the capability of the device to facilitate delivery of compositions of the invention, particularly linear DNA fragments, into the cells of the organism.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "radiation therapy" as used herein refers to radiation treatment given to cancer patients that damages the DNA in cancer cells, which often results in the death of cancer cells.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and a origin of replication.

The term "residual linear plasmid backbone" as used herein comprises any fragment of the plasmid backbone that is left at the end of the process making the nucleic acid expression plasmid linear.

The term "recipient-subject" as used herein refers to any species of the animal kingdom wherein modified-donor-cells can be introduced from a donor-subject.

The term "red blood cell mass" ("RBC-mass") of a subject as used herein is determined using one of the three following tests: 1) Hematocrit: the percentage of red blood cells in plasma; 2) red blood cell ("RBC") count: the number of red blood cells in plasma; and 3) hemoglobin: the level of oxygen-carrying protein within the subjects' red blood cells.

The term "regulator protein" as used herein refers to any protein that can be used to control the expression of a gene.

The term "regulator protein" as used herein refers to protein that increasing the rate of transcription in response to an inducing agent.

The terms "subject" or "animal" as used herein refers to any species of the animal kingdom. In preferred embodiments, it refers more specifically to humans and domesticated animals used for: pets (e.g. cats, dogs, etc.); work (e.g. horses, etc.); food (cows, chicken, fish, lambs, pigs, etc); and all others known in the art.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of linear DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a transgene, a poly A sequence, or a 3' or 5' UTR.

The term "transfects" as used herein refers to introduction of a nucleic acid into a eukaryotic cell. In some embodiments, the cell is not a plant tissue or a yeast cell.

The term "vector" as used herein refers to any vehicle that delivers a nucleic acid into a cell or organism. Examples include plasmid vectors, viral vectors, liposomes, or cationic lipids.

The term "viral backbone" as used herein refers to a nucleic acid sequence that does not contain a promoter, a gene, and a 3' poly A signal or an untranslated region, but contain elements including, but not limited at site-specific genomic integration Rep and inverted terminal repeats ("ITRs") or the binding site for the tRNA primer for reverse transcription, or a nucleic acid sequence component that induces a viral immunogenicity response when inserted in vivo, allows integration, affects specificity and activity of tissue specific promoters, causes transcriptional silencing or poses safety risks to the subject.

The term "vascular pressure pulse" refers to a pulse of pressure from a large volume of liquid to facilitate uptake of a vector into a cell. A skilled artisan recognizes that the amount and duration of the vascular pressure pulse is dependent on the tissue, size, and overall health of the recipient animal, and furthermore knows how to determine such parameters empirically.

The term "vector" as used herein refers to a construction comprised of genetic material designed to direct transformation of a targeted cell by delivering a nucleic acid sequence into that cell. A vector may contain multiple genetic elements positionally and sequentially oriented with other necessary elements such that an included nucleic acid cassette can be transcribed and when necessary translated in the transfected cells. These elements are operatively linked. The term "expression vector" refers to a DNA plasmid that contains all of the information necessary to produce a recombinant protein in a heterologous cell.

The term "wasting" as used herein is defined as decreased body weight characterized by significant loss of both adipose tissue and muscle mass that makes weight gain especially difficult for patients with progressive diseases, such as cancer or AIDS. Wasting can be related to the disease itself or the effects of its treatment, or both.

One aspect of the current invention pertains to a method useful for retarding the growth of abnormal cells, and promoteing tumor progression reduction in cancer-bearing animals. The method of this invention comprises treating a subject with plasmid mediated gene supplementation. The method comprises delivering an effective amount of a nucleic acid expression construct that encodes a growth-hormone-releasing-hormone ("GHRH") or functional biological equivalent thereof into a tissue, such as a muscle, of the subject. Specific embodiments of this invention are directed toward particular types of tumors (e.g. adenoma; carcinoma; leukemia; lymphoma; lung tumor; mast cell tumor; melanoma; sarcoma; and solid tumors). The subsequent in vivo expression of the GHRH or biological equivalent in the subject is sufficient to retard tumor growth, and retard cachexia or the wasting effects that are commonly associated with tumors. It is also possible to enhance this method by placing a plurality of electrodes in a selected tissue, then delivering nucleic acid expression construct to the selected tissue in an area that interposes the plurality of electrodes, and applying a cell-transfecting pulse (e.g. electrical) to the selected tissue in an area of the selected tissue where the nucleic acid expression construct was delivered. However, the cell-transfecting pulse need not be an electrical pulse, a vascular pressure pulse can also be utilized. Electroporation, direct injection, gene gun, or gold particle bombardment are also used in specific embodiments to deliver the nucleic acid expression construct encoding the GHRH or biological equivalent into the subject. The subject in this invention comprises an animal (e.g. a human, a pig, a horse, a cow, a mouse, a rat, a monkey, a sheep, a goat, a dog, or a cat).

Specific elements of the nucleic acid expression construct of this invention are also described. For example, the construct comprises a tissue specific promoter; a GHRH or functional equivalent; and a 3' untranslated region ("3'UTR") that are operatively linked. In specific embodiments, the tissue-specific promoter comprises a muscle-specific promoter (e.g., SPc5-12 (SEQ ID NO: 7)), and the 3' UTR of the nucleic acid expression construct comprises a human growth hormone 3' UTR (SEQ ID NO: 8), bovine growth hormone 3' UTR, skeletal apha actin 3' UTR or SV40 polyadenylation signal. The nucleic acid expression construct of this invention comprises a construct that is substantially free of a viral backbone. Specific examples of a nucleic acid expression construct used for this invention comprises plasmids with SEQ ID NO: 11, SEQ ID NO: 12, SEQ ID NO: 13, and SEQ ID NO: 14. The encoded functional biological equivalent of GHRH comprises a polypeptide having similar or improved biological activity when compared to the GHRH polypeptide. The GHRH or functional biological equivalent that is encoded by the nucleic acid expression construct and useful for this invention comprises an amino acid structure with a general sequence as follows (SEQ ID NO: 6):

wherein the formula has the following characteristics: $X_1$ is a D- or L-isomer of the amino acid tyrosine ("Y"), or histidine ("H"); $X_2$ is a D- or L-isomer of t he amino acid alanine ("A"), valine ("V"), or isoleucine ("I"); $X_3$ is is D- or L-isomer of the amino acid alanine ("A") or glycine ("G"); $X_4$ is a D- or L-isomer of the amino acid methionine ("M"), or leucine ("L"); $X_5$ is a D- or L-isomer of the amino acid serine ("S") or asparagine ("N"); or a combination thereof. Specific examples of amino acid sequence for GHRH or functional biological equivalents that are useful for this invention are presented in SEQ ID NO: 2; SEQ ID NO: 3; SEQ ID NO: 4; and SEQ ID NO: 10. In a specific embodiment, the encoded GHRH or functional biological equivalent thereof facilitates growth hormone ("GH") secretion in a subject that has received the nucleic acid expression construct.

Although not wanting to be bound by theory, the ability of cells in a tissue to uptake the nucleic acid expression construct can be facilitated by a transfection-facilitating polypeptide. In specific embodiments of the invention, the transfection-facilitating polypeptide comprises a charged polypeptide such as poly-L-glutamate.

Another aspect of the current invention comprise compositions that are useful for retarding the growth of abnormal cells, tumor progression reduction, prevention of kidney failure, reduction of metastasis, and increased survival in cancer-bearing animals. The composition of this invention comprises an effective amount of a nucleic acid expression construct that encodes a growth-hormone-releasing-hormone ("GHRH") or functional biological equivalent thereof, wherein delivering and subsequent expression of the GHRH or biological equivalent in a tissue of the subject is sufficient to retard the growth of abnormal cells, promote tumor progression reduction, prevent kidney failure, and increase survival in cancer-bearing animals. Specific embodiments of this invention are directed toward particular types of tumors and cancers (e.g. adenoma; carcinoma; leukemia; lymphoma; lung tumor; mast cell tumor; melanoma; sarcoma; and solid tumors).

The subsequent in vivo expression of the GHRH or biological equivalent encoded by the composition is sufficient to retard the growth of abnormal cells, promote tumor progression reduction, prevent kidney failure, and increase survival in cancer-bearing animals. It is also possible to enhance the uptake of the composition (i.e. nucleic acid expression construct) of this invention by placing a plurality of electrodes in a selected tissue, then delivering nucleic acid expression construct to the selected tissue in an area that interposes the plurality of electrodes, and then applying a cell-transfecting pulse (e.g. electrical) to the selected tissue in an area of the selected tissue where the nucleic acid expression construct was delivered. However, the cell-transfecting pulse need not be an electrical pulse, a vascular pressure pulse can also be utilized. Electroporation, direct injection, gene gun, or gold particle bombardment are also used in specific embodiments to deliver the composition that encodes the GHRH or biological equivalent into the subject. The subject in this invention comprises a mammal (e.g. a human, a pig, a horse, a cow, a mouse, a rat, a monkey, a sheep, a goat, a dog, or a cat).

Additionally, the invention relates to a plasmid-mediated supplementation method for the treatment of anemia, wasting, tumor growth, immune dysfunction, kidney failure and/or life extension for the chronically ill subject. Anemia refers to a condition in which there is a reduction of the number, volume, or both of red blood corpuscles or of the total amount of hemoglobin in the bloodstream, resulting in paleness, generalized weakness, etc. of the subject. Wasting of a subject can be defined as decreased body weight that is characterized by significant loss of both adipose tissue and muscle mass, which makes weight gain especially difficult for patients with a progressive disease (e.g. cancer, AIDS, etc.). Anemia, wasting, tumor growth, immune dysfunction, kidney failure and decreased life expectancy can be related to a specific disease or the effects of a disease treatment. More specifically, this invention pertains to a method for delivering a heterologous nucleic acid sequence encoding growth hormone releasing hormone ("GHRH") or biological equivalent thereof into the cells of the subject (e.g. somatic, stem, or germ cells) and allowing expression of the encoded GHRH or biological equivalent gene to occur while the modified cells are within the subject. The subsequent expression of the GHRH or biological equivalent thereof is regulated by a tissue specific promoter (e.g. muscle), and/or by a regulator protein that contains a modified ligand-binding domain (e.g. molecular switch), which will only be active when the correct modified ligand (e.g. mifepistone) is externally administered into the subject. The extracranial expression and ensuing release of GHRH or biological equivalent thereof by the modified cells can be used to treat anemia, wasting, tumor growth, immune dysfunction, kidney failure and life extension for the chronically ill subject. The preferred means to deliver the GHRH or biological equivalent thereof is by electroporation.

Recombinant GH replacement therapy is widely used clinically, with beneficial effects, but generally, the doses are supraphysiological. Such elevated doses of recombinant GH are associated with deleterious side-effects, for example, up to 30% of the recombinant GH treated patients report a higher frequency of insulin resistance (Blethen, 1995; Verhelst et al., 1997) or accelerated bone epiphysis growth and closure in pediatric patients (Blethen and Rundle, 1996). In addition, molecular heterogeneity of circulating GH may have important implications in growth and homeostasis, which can lead to a less potent GH that has a reduced ability to stimulate the prolactin receptor (Satozawa et al., 2000; Tsunekawa et al., 1999; Wada et al., 1998). These unwanted side effects result from the fact that treatment with recombinant exogenous GH protein raises basal levels of GH and abolishes the natural episodic pulses of GH. In contradistinction, no side effects have been reported for recombinant GHRH therapies. The normal levels of GHRH in the pituitary portal circulation range from about 150-to-800 pg/ml, while systemic circulating values of the hormone are up to about 100-500 pg/ml. Some patients with acromegaly caused by extracranial tumors have level that is nearly 10 times as high (e.g. 50 ng/ml of immunoreactive GHRH) (Thorner et al., 1984). Long-term studies using recombinant GHRH therapies (1-5 years) in children and elderly humans have shown an absence of the classical GH side-effects, such as changes in fasting glucose concentration or, in pediatric patients, the accelerated bone epiphysal growth and closure or slipping of the capital femoral epiphysis (Chevalier et al., 2000) (Duck et al., 1992; Vittone et al., 1997). Numerous studies in humans, sheep or pigs showed that continuous infusion with recombinant GHRH protein restores the normal GH pattern without desensitizing GHRH receptors or depleting GH supplies (Dubreuil et al., 1990). As this system is capable of a degree of feed-back which is abolished in the GH therapies, GHRH recombinant protein therapy may be more physiological than GH therapy. However, due to the short half-life of GHRH in vivo, frequent (one to three times per day) intravenous, subcutaneous or intranasal (requiring 300-fold higher dose) administrations are necessary (Evans et al., 1985; Thorner et al., 1986). Thus, as a chronic therapy, recombinant GHRH protein administration is not practical. A gene transfer approach, however could overcome this limitations to GHRH use. Moreover, a wide range of doses can be therapeutic. The choice of GHRH for a gene therapeutic application is favored by the fact that the gene, cDNA and native and several mutated molecules have been characterized for the pig and other species (Bohlen et al., 1983; Guillemin et al., 1982), and the measurement of therapeutic efficacy is straightforward and unequivocal.

Among the non-viral techniques for gene transfer in vivo, the direct injection of plasmid DNA into muscle is simple, inexpensive, and safe. The inefficient DNA uptake into muscle fibers after simple direct injection hag led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996). Recently, significant progress to enhance plasmid delivery in vivo and subsequently to achieve physiological levels of a secreted protein was obtained using the electroporation technique. Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Our previous studies using growth hormone releasing hormone (GHRH) showed that plasmid therapy with electroporation is scalable and represents a promising approach to induce production and regulated secretion of proteins in large animals and humans (Draghia-Akli et al., 1999; Draghia-Akli et al., 2002). Electroporation also has been extensively used in rodents and other small animals (Bettan et al., 2000; Yin and Tang, 2001). It has been observed that the electrode configuration affects the electric field distribution, and subsequent results (Gehl et al., 1999; Miklavcic et al., 1998). Preliminary experiments indicated that for a large animal model, needle electrodes give consistently better reproducible results than external caliper electrodes.

The ability of electroporation to enhance plasmid uptake into the skeletal muscle has been well documented, as described above. In addition, plasmid formulated with PLG or polyvinylpyrrolidone ("PVP") has been observed to increase gene transfection and consequently gene expression to up to 10 fold in the skeletal muscle of mice, rats and dogs (Fewell et al., 2001; Mumper et al., 1998). Although not wanting to be bound by theory, PLG will increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, process that substantially increases the transfection efficiency.

The plasmid supplementation approach to treat anemia, wasting, tumor growth, immune dysfunction, kidney failure and life extension for the chronically ill subject that is described herein offers advantages over the limitations of directly injecting recombinant GH or GHRH protein. Expression of novel biological equivalents of GHRH that are serum protease resistant can be directed by an expression plasmid controlled by a synthetic muscle-specific promoter. Expression of such GHRH or biological equivalent thereof elicited high GH and IGF-I levels in subjects that have had the encoding sequences delivered into the cells of the subject by intramuscular injection and in vivo electroporation. Although in vivo electroporation is the preferred method of introducing the heterologous nucleic acid encoding system into the cells of the subject, other methods exist and should be known by a person skilled in the art (e.g. electroporation, lipofectamine, calcium phosphate, ex vivo transformation, direct injection, DEAE dextran, sonication loading, receptor mediated transfection, microprojectile bombardment, etc.). For example, it may also be possible to introduce the nucleic acid sequence that encodes the GHRH or functional biological equivalent thereof directly into the cells of the subject by first removing the cells from the body of the subject or donor, maintaining the cells in culture, then introducing the nucleic acid encoding system by a variety of methods (e.g. electroporation, lipofectamine, calcium phosphate, ex vivo transformation, direct injection, DEAE dextran, sonication loading, receptor mediated transfection, microprojectile bombardment, etc.), and finally reintroducing the modified cells into the original subject or other host subject (the ex vivo method). The GHRH sequence can be cloned into an adenovirus vector or an adeno-associated vector and delivered by simple intramuscular injection, or intravenously or intra-arterially. Plasmid DNA carrying the GHRH sequence can be complexed with cationic lipids or liposomes and delivered intramuscularly, intravenously or subcutaneous.

Administration as used herein refers to the route of introduction of a vector or carrier of DNA into the body. Administration can be directly to a target tissue or by targeted delivery to the target tissue after systemic administration. In particular, the present invention can be used for treating disease by administration of the vector to the body in order to establishing controlled expression of any specific nucleic acid sequence within tissues at certain levels that are useful for plasmid mediated supplementation. The preferred means for administration of vector and use of formulations for delivery are described above.

Muscle cells have the unique ability to take up DNA from the extracellular space after simple injection of DNA particles as a solution, suspension, or colloid into the muscle. Expression of DNA by this method can be sustained for several months. DNA uptake in muscle cells is further enhance utilizing in vivo electroporation.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determine the bioavailability of the vector within the body. Other elements of the formulation function as ligands that interact with specific receptors on the surface or interior of the cell. Other elements of the formulation function to enhance entry into the cell, release from the endosome, and entry into the nucleus.

Delivery can also be through use of DNA transporters. DNA transporters refer to molecules which bind to DNA vectors and are capable of being taken up by epidermal cells. DNA transporters contain a molecular complex capable of non-covalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993.

Another method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine; one element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs plasmid-mediated supplementation and the genetically engineered cells can also be easily put back with out causing damage to the patient's muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the E1 region of the virus genome with the vector elements described in this invention including promoter, 5'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

Although not wanting to be bound by theory, it is believed that in order to provide an acceptable safety margin for the use of such heterologous nucleic acid sequences in humans, a regulated gene expression system is mandated to possess low levels of basal expression of GHRH, and still retain a high ability to induce. Thus, target gene expression can be regulated by incorporating molecular switch technology as schematically diagramed in FIG. 9 and further discussed in Example 1. The HV-GHRH or biological equivalent molecule displays a high degree of stability in serum, with a half-life of 6 hours, versus the natural GHRH, that has a 6-12 minutes half-life. Thus, by combining the powerful electroporation DNA delivery method with stable and regulable GHRH or biological equivalent encoded nucleic acid sequences, a therapy can be utilized that will reverse chronic wasting, allow the subject to gain weight, and extend the subject's life expectancy.

I. Vectors

The term "vector" is used to refer to a carrier nucleic acid molecule into which a nucleic acid sequence can be inserted for introduction into a cell wherein, in some embodiments, it can be replicated. A nucleic acid sequence can be native to the animal, or it can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operatively linked coding sequence in a particular host cell. In addition to control sequences that govern transcription and translation, vectors and expression vectors may contain nucleic acid sequences that serve other functions as well and are described infra.

II. Plasmid Vectors

In certain embodiments, a linear DNA fragment from a plasmid vector is contemplated for use to transfect a eukaryotic cell, particularly a mammalian cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins. A skilled artisan recognizes that any plasmid in the art may be modified for use in the methods of the present invention. In a specific embodiment, for example, a GHRH vector used for the therapeutic applications is derived from pBlueScript KS+ and has a kanamycin resistance gene.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase ("GST") soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

III. Promoters and Enhancers

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | Relevant References |
|---|---|
| Immunoglobulin Heavy Chain | |
| Immunoglobulin Light Chain | |
| T-Cell Receptor | |
| HLA DQ a and/or DQ β | |
| β-Interferon | |
| Interleukin-2 | |

TABLE 1-continued

Promoter and/or Enhancer

| Promoter/Enhancer | Relevant References |
|---|---|
| Interleukin-2 Receptor | |
| MHC Class II 5 | |
| MHC Class II HLA-Dra | |
| β-Actin | (Kawamoto et al., 1988; Kawamoto et al., 1989) |
| Muscle Creatine Kinase (MCK) | (Horlick and Benfield, 1989; Jaynes et al., 1988) |
| Prealbumin (Transthyretin) | |
| Elastase I | |
| Metallothionein (MTII) | (Inouye et al., 1994; Narum et al., 2001; Skroch et al., 1993) |
| Collagenase | |
| Albumin | (Pinkert et al., 1987; Tronche et al., 1989) |
| α-Fetoprotein | |
| γ-Globin | |
| β-Globin | (Tronche et al., 1990; Trudel and Costantini, 1987) |
| c-fos | |
| c-HA-ras | |
| Insulin | (German et al., 1995; Ohlsson et al., 1991) |
| Neural Cell Adhesion Molecule (NCAM) | |
| $\alpha_1$-Antitrypsin | |
| H2B (TH2B) Histone | |
| Mouse and/or Type I Collagen | |
| Glucose-Regulated Proteins (GRP94 and GRP78) | |
| Rat Growth Hormone | (Larsen et al., 1986) |
| Human Serum Amyloid A (SAA) | |
| Troponin I (TN I) | (Lin et al., 1991; Yutzey and Konieczny, 1992) |
| Platelet-Derived Growth Factor (PDGF) | (Pech et al., 1989) |
| Duchenne Muscular Dystrophy | (Klamut et al., 1990; Klamut et al., 1996) |
| SV40 | |
| Polyoma | |
| Retroviruses | |
| Papilloma Virus | |
| Hepatitis B Virus | |
| Human Immunodeficiency Virus | |
| Cytomegalovirus CMV | (Boshart et al., 1985; Dorsch-Hasler et al., 1985) |
| Gibbon Ape Leukemia Virus | |
| Synthetic muscle specific promoters (c5-12, c1-28 | (Draghia-Akli et al., 1999; Draghia-Akli et al., 2002; Li etal., 1999) |

TABLE 2

Element/Inducer

| Element | Inducer |
|---|---|
| MT II | Phorbol Ester (TFA) |
| | Heavy metals |
| MMTV (mouse mammary tumor virus) | Glucocorticoids |
| β-Interferon | Poly (rI)x / Poly (rc) |
| Adenovirus 5 E2 | E1A |
| Collagenase | Phorbol Ester (TPA) |
| Stromelysin | Phorbol Ester (TPA) |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2κb | Interferon |
| HSP70 | E1A, SV40 Large T Antigen |
| Proliferin | Phorbol Ester-TPA |

TABLE 2-continued

Element/Inducer

| Element | Inducer |
|---|---|
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Nonlimiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), DIA dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (Li et al., 1999), which contains a proximal serum response element ("SRE") from skeletal α-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention.

IV. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites ("IRES") elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

V. Multiple Cloning Sites

Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998) incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

VI. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, (Chandler et al., 1997), herein incorporated by reference.)

VII. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues ("polyA") to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

VIII. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal, skeletal alpha actin 3'UTR or the human or bovine growth hormone polyadenylation signal, convenient and known to function well in various target cells. Polyadenylation may increase the stability of the transcript or may facilitate cytoplasmic transport.

IX. Origins of Replication

In order to propagate a vector in a host cell, it may contain one or more origins of replication sites (often termed "ori"), which is a specific nucleic acid sequence at which replication is initiated. Alternatively an autonomously replicating sequence ("ARS") can be employed if the host cell is yeast.

X. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase ("tk") or chloramphenicol acetyltransferase ("CAT") may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

XI. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding and other methods known in the art.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances, maintain a resting transmembrane potential of ca. 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula $E=V/d$, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the interelectrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol, and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

One embodiment of the present invention to overcome the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determine by the nature of tissue, the size of the selected tissue and distance between electrodes. It is desirable that the voltage pulse be as homogenous as possible and of the correct amplitude. Excessive field strength results in the lysing of cells, whereas a low field strength results in reduced efficacy of electroporation. Some electroporation devices utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

XII. Restriction Enzymes

In some embodiments of the present invention, a linear DNA fragment is generated by restriction enzyme digestion of a parent DNA molecule. Examples of restriction enzymes are provided in the following table.

| Name | Recognition Sequence |
|------|---------------------|
| AatII | GACGTC |
| Acc65 I | GGTACC |

-continued

| Name | Recognition Sequence |
|---|---|
| Acc I | GTMKAC |
| Aci I | CCGC |
| Acl I | AACGTT |
| Afe I | AGCGCT |
| Afl II | CTTAAG |
| Afl III | ACRYGT |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| ApaL I | GTGCAC |
| Apo I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| Bam HI | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |
| Bcl I | TGATCA |
| Bfa I | CTAG |
| Bgl I | GCCNNNNNGGC |
| Bgl II | AGATCT |
| Blp I | GCTNAGC |
| Bmr I | ACTGGG |
| Bpm I | CTGGAG |
| BsaA I | YACGTR |
| BsaB I | GATNNNNATC |
| BsaH I | GRCGYC |

-continued

| Name | Recognition Sequence |
|---|---|
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| Bsl I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp 1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC |
| BstB I | TTCGAA |
| BstE II | GGTNACC |
| BstF5 I | GGATGNN |
| BstN I | CCWGG |
| BstU I | CGCG |
| BstX I | CCANNNNNNTGG |
| BstY I | RGATCY |
| BstZ17 I | GTATAC |
| Bsu36 I | CCTNAGG |
| Btg I | CCPuPyGG |

-continued

| Name | Recognition Sequence |
|---|---|
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinP1 I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |

-continued

| Name | Recognition Sequence |
|---|---|
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |
| MspA1 I | CMGCKG |
| Msp I | CCGG |
| Mwo I | GCNNNNNNNGC |
| Nae I | GCCGGC |
| Nar I | GGCGCC |
| Nci I | CCSGG |
| Nco I | CCATGG |
| Nde I | CATATG |
| NgoMI V | GCCGGC |
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| PleI | GAGTC |
| Pme I | GTTTAAAC |
| Pml I | CACGTG |
| PpuM I | RGGWCCY |
| PshA I | GACNNNNGTC |
| Psi I | TTATAA |
| PspG I | CCWGG |
| PspOM I | GGGCCC |
| Pst I | CTGCAG |
| Pvu I | CGATCG |
| Pvu II | CAGCTG |
| Rsa I | GTAC |

| Name | Recognition Sequence |
| --- | --- |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTG G |
| Xho I | CTCGAG |
| Xma I | CCCGGG |
| Xmn I | GAANNNNTTC |

The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in the art.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of DNA Vectors and Methods in Animal Subject

In order to treat anemia; increase total red blood cell mass; reverse the wasting; reverse abnormal weight loss; treat immune dysfunction; reverse the suppression of lymphopoesis; or extend life expectancy for the chronically ill subject, it was first necessary to design several GHRH expression constructs. Briefly, the plasmid vectors contained the muscle specific synthetic promoter SPc5-12 (Li et al., 1999) attached to a wild type or analog porcine GHRH. The analog GHRH sequences were generated by site directed mutagenesis as described in methods section. Nucleic acid sequences encoding GHRH or analog were cloned into the BamHI/HindIII sites of pSPc5-12 plasmid, to generate pSP-GHRH. Other elements contained in the plasmids include a 3' untranslated region of growth hormone and an SV40 3'UTR from pSEAP-2 Basic Vector as described in the methods section. The unique nucleic acid sequences for the constructs used are shown in FIG. 1.

DNA Constructs: Plasmid vectors containing the muscle specific synthetic promoter SPc5-12 (SEQ ID NO: 7) were previously described (Li et al., 1999). Wild type and mutated porcine GHRH cDNAs were generated by site directed mutagenesis of GHRH cDNA (SEQ ID NO: 9) (Altered Sites II in vitro Mutagenesis System, Promega, Madison, Wis.), and cloned into the BamHI/Hind III sites of pSPc5-12, to generate pSP-wt-GHRH (SEQ ID NO: 15), or pSP-HV-GHRH (SEQ ID NO: 11), respectively. The 3" untranslated region (3" UTR) of growth hormone was cloned downstream of GHRH cDNA. The resultant plasmids contained mutated coding region for GHRH, and the resultant amino acid sequences were not naturally present in mammals. Although not wanting to be bound by theory, the effects on treating anemia; increasing total red blood cell mass in a subject; reversing the wasting; reversing abnormal weight loss; decreasing tumor growth; preventing kidney failure; treating immune dysfunction; reversing the suppression of lymphopoesis; or extending life expectancy for the chronically ill subject are determined ultimately by the circulating levels of mutated hormones. Several different plasmids that encoded different mutated amino acid sequences of GHPd-t or functional biological equivalent thereof are as follows:

SPc5-12 fragment, SEAP gene and SV40 3"UTR from pSEAP-2 Basic Vector (Clontech Laboratories, Inc.; Palo Alto, Calif.).

The plasmids described above do not contain polylinker, IGF-I gene, a skeletal alpha-actin promoter or a skeletal alpha actin 3' UTR /NCR. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Functional biological equivalents are thus defined herein as those proteins (and polynucleotides) in selected amino acids (or codons) may be substituted. A peptide comprising a functional biological equivalent of GHRH is a polypeptide that has been engineered to contain distinct amino acid sequences while simultaneously having similar or improved biologically activity when compared to GHRH. For example one biological activity of GHRH is to facilitate growth hormone ("GH") secretion in the subject.

Large Animal Studies: Healthy Dogs: A group of 4 dogs (2 males and 2 females) were used as controls and 3 groups of 8 dogs (4 males and 4 females) were injected with the pSP-HV-GHRH system. The dogs were injected with vehicle alone (control), or 200 mcg, or 600 mcg or 1000 mcg of pSP-HV-GHRH followed by caliper electroporation.

Cancer Dogs: Fifteen dogs with spontaneous malignancies were used in GHRH studies. The dogs were injected with 100 mcg/kg to a total of no more than 1000 mcg pSP-HV-GHRH. Four dogs died or were euthanized at

| Plasmid | Encoded Amino Acid Sequence | |
|---|---|---|
| wt-GHRH | YADAIFTNSYRKVLGQLSARKLLQDIMSRQQGERNQEQGA-OH | (SEQID#10) |
| HV-GHRH | HVDAIFTNSYRKVLAQLSARKLLQDILNRQQGERNQEQGA-OH | (SEQID#1) |
| TI-GHRH | YIDAIFTNSYRKVLAQLSARKLLQDILNRQQGERNQEQGA-OH | (SEQID#2) |
| TV-GHRH | YVDAIFTNSYRKVLAQLSARKLLQDILNRQQGERNQEQGA-OH | (SEQID#3) |
| 15/27/28-GHRH | YADAIFTNSYRKVLAQLSARKLLQDILNRQQGERNQEQGA-OH | (SEQID#4) |

In general, the encoded GHRH or functional biological equivalent thereof is of formula:

    $-X_1-X_2$-DAIFTNSYRKVL-$X_3$-QLSARKLLQDI-$X_4$-$X_5$-RQQGERNQEQGA-OH (SEQ ID NO: 6) wherein: $X_1$ is a D- or L-isomer of an amino acid selected from the group consisting of tyrosine ("Y"), or histidine ("H"); $X_2$ is a D- or L-isomer of an amino acid selected from the group consisting of alanine ("A"), valine ("V"), or isoleucine ('T'); $X_3$ is a D- or L-isomer of an amino acid selected from the group consisting of alanine ("A") or glycine ("G"); $X_4$ is a D- or L-isomer of an amino acid selected from the group consisting of methionine ("M"), or leucine ("L"); $X_5$ is a D- or L-isomer of an amino acid selected from the group consisting of serime ("S") or asparagine ("N").

Another plasmid that was utilized included the pSP-SEAP construct (SEQ ID No: 16) that contains the SadI/HindIII owner's request within the first three days after the plasmid injection from unrelated complications of their advanced disease. The condition of inclusion in our study was a survival of at least 14 days post-injection (in order to allow for plasmid activation and expression of GHRH from the skeletal muscle), when a second blood draw could be made. Eleven dogs were analyzed in this study. The animals were under specific treatment using either chemotherapy, radiotherapy or combination therapy (see FIG. 18). The animals were weighed and bled before the treatment and at 9-27 and 28-56 days post-injection. At each time point complete CBC and metabolic profile was assessed by the same independent laboratory (Antech Diagnostics, Irvine, Calif.). Wellness forms were completed by owners at each visit. Nineteen non-injected dogs with spontaneous malignancies, in treatment in the clinic in the same time window, were used as contemporary controls. The quality of life in the treated patients increased. No adverse effects linked to the therapy were noted by owners. Three owners noticed a dramatic improvement in the general well-being of the treated dog compared to pre-injection status.

Electroporation devices: A BTX T820 generator (BTX, division of Genetronics Inc., CA) was used to deliver square wave pulses in all experiments. We used voltage conditions of 100V/cm, 6 pulses, 60 milliseconds per pulse. Two-needle electrodes (BTX, a division of Genetronics Inc., CA) were used to deliver in vivo electric pulses. In all injections the needles were completely inserted into the muscle.

Intramuscular injection of plasmid DNA in Canine subjects: Four groups of healthy Canines ("dogs") subjects, 8-12 kg in weight, were used for biodistribution -toxicology studies. Three groups of 8 dogs (4 males and 4 females) were injected with 200 mcg, 600 mcg and 1000 mcg of pSP-HV-GHRH, respectively. A group of 4 dogs (2 males and 2 females) were used as controls. Animals were continuously monitored for side effects. In addition, two groups of dogs with cancer (spontaneous malignancies) were used. Animals were maintained in accordance with NIH Guide, USDA and Animal Welfare Act guidelines, and approved by the Baylor College of Medicine IACUC.

Endotoxin-free plasmid (Qiagen Inc., Chatsworth, Calif., USA) preparation of pSPc5-12-HV-GHRH were diluted in PBS pH=7.4 or water to 5 mg/mL. Dogs were injected before their regular treatment administration. For dogs on chemotherapy, the injection was administered at no less than 5 days before/after the medication. The dogs were anesthetized with Propafol (Abbott Laboratories, IL) 4-8 mg/kg. While anesthetized, 100 µg/kg to a maximum of 1 mg of plasmid was injected directly into the semitendinosus muscle of dogs, using an 3/10 cc insulin syringe and 29G1/2" needle (Becton-Dickinson, Franklin Lacks, N.J.). Two minutes after injection, the injected muscle was electroporated, 6 pulses, 100V/cm, 60 milliseconds/pulse, using a BTX T820 electroporator and two-needle electrodes (BTX, a division of Genetronics Inc., CA), as described (Miklavcic et al., 2000). In all injections the needles were completely inserted into the muscle. Animals were allowed to recover before rejoining their owners.

Although in vivo electroporation is the preferred method for delivering the nucleic acid constructs into the cells of the subject, suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Nabel et al., 1989; Wilson et al., 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985) U.S. Pat. No. 5,789,215, incorporated herein by reference); by electroporation (U.S. Pat. No. 5,384,253, incorporated herein by reference; (Potter et al., 1984; Tur-Kaspa et al., 1986); by calcium phosphate precipitation (Chen and Okayama, 1987; Graham and van der Eb, 1973; Rippe et al., 1990); by using DEAE-dextran followed by polyethylene glycol (Gopal, 1985); by direct sonic loading (Fechheimer et al., 1987); by liposome mediated transfection (Hafez et al., 2001; Hamm et al., 2002; Madry et al., 2001; Raghavachari and Fahl, 2002; Wiethoff et al., 2001) and receptor-mediated transfection (Wu and Wu, 1988a; Wu and Wu, 1988b); by micro-projectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers ((Johnson et al., 1992); U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993); U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

Body weight data: Animals were weighted before the plasmid injection and at 14, 28 and 56 days post-injection using the same calibrated scale.

Protein Metabolism, Bone metabolism and Blood values: Blood and urine samples were collected before plasmid injection, and at 14, 28 and 56 days post-injection, and analyzed for biochemistry, metabolisms and hormone. At each time point complete CBC and metabolic profile was assessed by the same independent laboratory (Antech Diagnostics, Irvine, Calif.).

Plasma IGF-I: IGF-I levels were measured by heterologous human radioimmunometric assay (Diagnostic System Lab., Webster, Tex.). The sensitivity of the assay was 0.8 ng/ml; intra-assay and inter-assay variation was 3.4% and 4.5% respectively.

Statistics: Data are analyzed using STATISTICA analysis package (StatSoft, Inc. Tulsa, Okla.). Values shown in the Figures are the mean±s.e.m. Specific P values were obtained by comparison using ANOVA. A $P<0.05$ was set as the level of statistical significance.

Example 2

Low Voltage Electroporation for DNA Uptake and Expression in an Animal Subject

Direct intra-muscular plasmid DNA injection followed by electroporation is a method for the local and controlled delivery of plasmid DNA into skeletal muscle. It has the advantage that is uses low plasmid quantities (as low as 0.1 mg), rather than the high quantities typically used with passive delivery modalities. Although not wanting to be bound by theory, the mechanism of the increased plasmid uptake by electroporation probably occurs through newly created membrane pores with or without protein active transport. Although not wanting to be bound by theory, the degree of permeabilization of the muscle cells is dependent on the electric field intensity, length of pulses, shape and type of electrodes (Bureau et al., 2000) (Gilbert et al., 1997), and cell size (Somiari et al., 2000). Classical electrode configuration, plates or a pair of wire electrodes placed 4 mm apart were shown to be effective in rodents, but in large mammals as pigs or humans the increased resistance of the skin, the thickness of the subcutaneous fat tissue, and the concern for tissue damage if the intensity of the electric field would be proportionally increased, make these types of electrodes unpractical. The porcine or dog muscle fibers are quite large and consequently more suitable for electropermeabilization than rodent muscle. In this report, we show that a single injection various dosages of GHRH or analog nucleic acid sequences followed by electroporation with intramuscular applicators, in a large mammal is sufficient to produce therapeutic plasma hormone levels, with biologically significant effects that can treat anemia, reverse wasting, allow the subject to gain weight, and extend life expectancy of the chronically ill.

The pSP-HV-GHRH system was delivered to the left tibialis anterior muscle of healthy dogs via in vivo electroporation. A group of 4 dogs (2 males and 2 females) were used as controls and 3 groups of 8 dogs (4 males and 4 females) were injected with the pSP-HV-GHRH system. The dogs were injected with vehicle alone (control), or 200 mcg, or 600 mcg or 1000 mcg of pSP-HV-GHRH followed by needle electroporation. An indication of increased systemic levels of GHRH and GH is an increase in serum IGF-I concentration. Therefore, following 28 days post injection blood serum was collected from the dogs were injected with vehicle alone (control), or 200 mcg, or 600 mcg or 1000 mcg of pSP-HV-GHRH and IGF-I levels were determined. The IGF-I levels for dogs injected with 600 mcg were 3-fold higher than the control (vehicle alone) treated animals (FIG. 2). The increase in IGF-I levels was statistically significant ($p<0.046$). Although animals injected with 200 mcg and 1000 mcg of plasmid showed higher IGF-I levels than controls, the IGF-I levels were lower than animals injected with 600 mcg. Increased IGF-I levels corresponding to higher GHRH levels are in agreement with other studies that utilized recombinant porcine GH ("pGH") in dogs. For example, there were dose-related increased serum IGF-I levels (approximately 2-10-fold) that correlated with the elevated serum GH levels in pGH-treated dogs.

Although not wanting to be bound by theory, growth hormone releasing hormone (GHRH) stimulates the production and release from the anterior pituitary of growth hormone (GH), which in turn stimulates the production of IGF-I from the liver and other target organs. Thus, an indication of increased systemic levels of GHRH and GH is an increase in serum IGF-I concentration. The level of serum IGF-I in healthy dogs injected with 200, 600 and 1000 mcg of pSP-HV-GHRH were all higher 28 days post-injection when compared to the pre-injection values. Dogs injected with 600 mcg pSP-HV-GHRH showed the highest statistically significant increase (e.g. greater than 90%, $p <0.046$) in IGF-I levels, which indicates that 600 mcg may be the optimal concentration for healthy dogs.

Example 3

Increased Survival in Animal Subjects with Cancer

Eleven injected dogs with cancer had survived for at least 56 days after the injection, and complete data was collected in all cases. The dogs enrolled in the study were in a relatively advanced stage of their disease (206 days since the beginning of the therapy). The average survival post-injection is listed in FIG. 18. At the time this application was prepared, 8 out of the eleven treated dogs were still alive (average survival post injection 150.6 days). The 19 control dogs were in a less advanced stage of disease and had an average survival of 56 days after the initial diagnosis. In contrast, after the enrollment into the present study the average survival post enrolment was 162.5 days. Five control animals died during this period. The quality of life in the treated patients increased. No adverse effects linked to the therapy were noted by owners. Three owners noticed a dramatic improvement in the general well-being of the treated dog compared to pre-injection status.

Example 4

Increased Weight Gain in Healthy Animal Subjects

Figure 4:
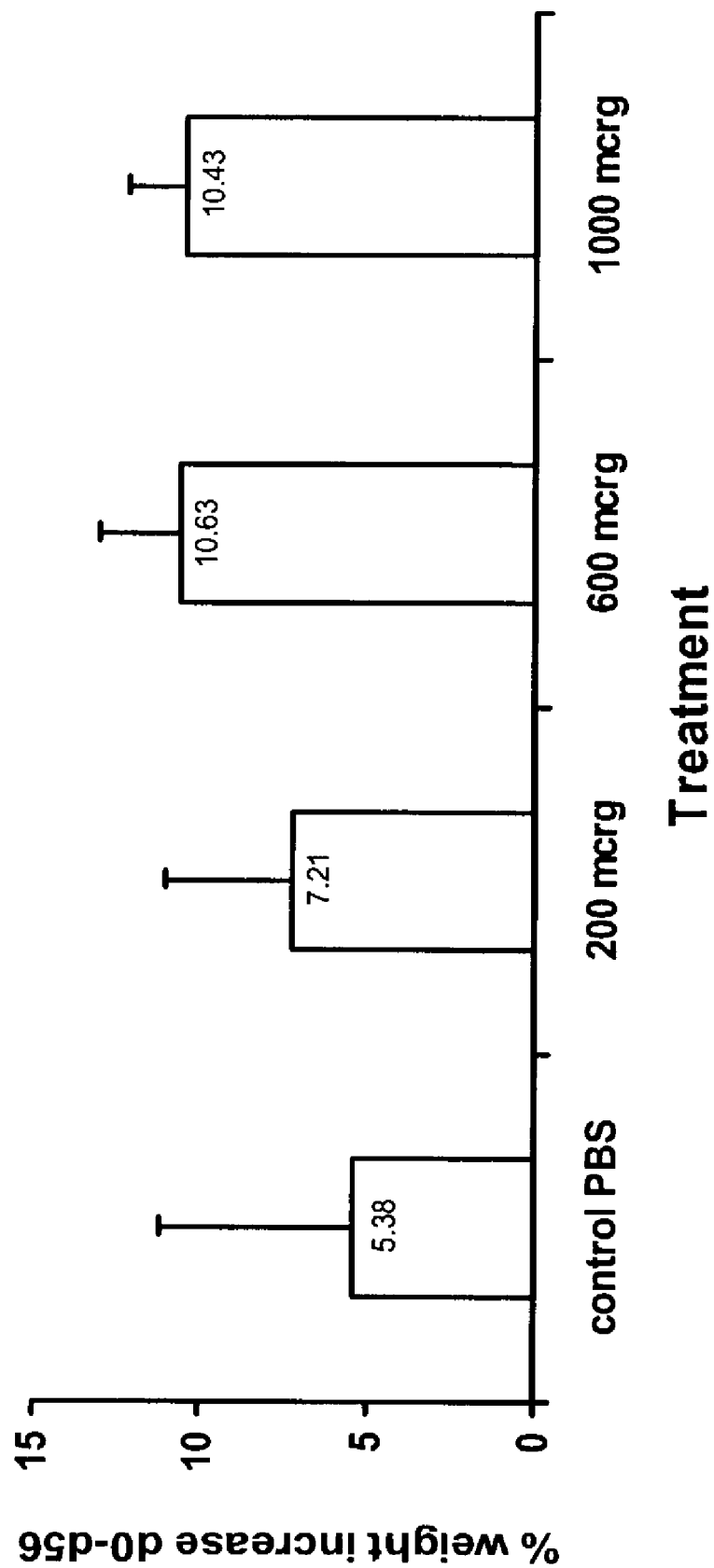
FIG. 4 shows the percentage of weight gain in healthy dogs that were injected with different concentrations of the pSP-HV-GHRH plasmid.

In order to show that increased levels of GHRH or biological equivalent thereof could alter metabolism in large healthy animals, body weight was determined. As shown in FIG. 4, the treated dogs had increased weight gain compared with controls fifty-six days post-injection. Although animals injected with 200 mcg and 1000 mcg of plasmid showed higher body weights than controls, the weights were lower than animals injected with 600 mcg. These results are a good indicator that the metabolism of the dogs injected with pSP-HV-GHRH was altered in a dose dependent manner. In addition, the additional weight gain associated with increased production of GHRH also indicates that the levels of GH were increased. This observation is in agreement with other studies that utilized recombinant porcine GH (pGH) in dogs. In one of these studies, recombinant pGH was administered for 14-weeks in dogs. Porcine GH caused increased body weight gain in mid - and high-dose groups (2.8 kg and 4.7 kg, respectively), compared to 0.4 kg and 0.8 kg in control and low-dose groups, respectively.

Example 5

GHRH or Biological Equivalent Treatment Improves Protein Utilization in Healthy Dogs FIG. 15 shows the changes in values associated with protein metabolism in healthy dogs injected with different concentrations of the pSP-HV-GHRH plasmid. Many values that indicate protein metabolism were monitored for 56 days including: AST, ALT, T. bilirubin, Alk Phos, GGT, total protein, albumin, globulin, A/G ratio, Cholesterol, BUN and creatinine. Groups of 8 dogs (4 males and 4 females) were injected with 200 mcg, 600 mcg and 1000 mcg of pSP-HV-GHRH. A group of 4 dogs (2 males and 2 females) were used as controls. Dogs injected with 200, and 600 mcg of plasmid had increased total protein levels. All injected groups have slightly decreased urea compared with controls, which is a sign of improved protein utilization.

Example 6

GHRH or Biological Equivalent Treatment Does Not Affect Glucose Metabolism in Healthy Animal Subjects.

FIG. 16 shows the changes in values associated with blood components in healthy dogs injected with different concentrations of the pSP-HV-GHRH plasmid. Abbreviations are as follows: WBC—White Blood Cell; RBC—Red blood cell; HGB—hemoglobin; PCV—hematocrit, or packed cell volume; MCV—mean corpuscular volume; MCH—mean corpuscular hemoglobin; MCHC—mean corpuscular hemoglobin concentration; n %-% of neutrophils; lym %-% of lymphocytes; mono %-% of monocytes; eos %-% of eosinophils; Bas %-% of basophils; LDH—lactate dehydrogenase ; Prothom—prothrombine; Qnt—quantitative; Plat—platelets; BUN—blood urea nitrogen/urea.

Many blood component values were monitored for 56 days including: WBC, RBC, HGB, PCV, MCB, MCH, MCHC, n %, lym % mono % eos %, Bas %, LDH, Prothom, Qnt. Plat. Groups of 8 dogs (4 males and 4 females) were injected with 200 mcg, 600 mcg and 1000 mcg of pSP-HV-GHRH. A group of 4 dogs (2 males and 2 females) were used as controls. No statistical differences were found between experimental and control groups. However, circulation lymphocytes decreased with the increase in the plasmid dosage, sign of lymphocyte sequestration in the lymphatic organs. Importantly, glucose levels in all experimental groups and controls are within the normal range, which indicates that our therapy does not impair glucose metabolism.

Example 7

GHRH or Biological Equivalent Treatment Effects Bone Remodeling

FIG. 17 shows the changes in values associated with bone metabolism in healthy dogs injected with different concentrations of the pSP-HV-GHRH plasmid. The phosphorus, calcium and calcium/phosphorous ratio was monitored for 56 days post injection. Groups of 8 dogs (4 males and 4 females) were injected with 200 mcg, 600 mcg and 1000 mcg of pSP-HV-GHRH. A group of 4 dogs (2 males and 2 females) were used as controls. Dogs injected plasmid had an increased $Ca/PO_4$ ratio that was proportional with the dosage of the treatment, which is a sign of bone remodeling.

Example 8

GHRH or Biological Equivalent Treatment Extends Life Expectancy in Chronically Ill Subjects FIG. 18 shows the diagnosis, specific therapy chart and survival for dogs with spontaneous cancer that were injected with different concentrations of the pSP-HV-GHRH plasmid. The study, group, treatment, dose, # of dogs, cancer type, and days survived post-treatment are indicated. Groups of dogs with spontaneous cancer were injected with 100 mcg/Kg body weight to a total of no more than 1000 mcg of pSP-HV-GHRH. In addition, dogs treated with pSP-HV-GHRH had an improved quality of life.

Example 9

GHRH or Biological Equivalent Treatment Positively Affects Immune Function in Cancer Subjects FIG. 19 shows the changes in values associated with blood components in dogs with spontaneous cancer injected with different concentrations of the pSP-HV-GHRH plasmid. Many blood component values were monitored post injection including: WBC/HPF, RBC/HBF, HGB, % PCV, MCV, MCH, MCHC, n %, lym % mono % eos %, Bas %. Groups of dogs with spontaneous cancer were injected with 100-1000 mcg/Kg body weight of pSP-HV-GHRH. Overall dogs treated with the pSV-HV-GHRH plasmid therapy, had increased RBC hemoglobin and hematocrit levels two weeks post-injection compared with un-injected controls. In addition, treated dogs have a significant decrease in the levels of circulation white blood cells (usually associated with increase of white blood cells (WBC) in the lymphatic organs but an increase in lymphocyte percentage. Treated animals showed a significant increase in the circulating lymphocytes at the early time points post-injection (15.11±2.81 vs. 12.5±2.41%, p<0.046 pst/pri). Control animals had lymphocyte values at the time points tested (p=0.32).

Example 10

GHRH or Biological Equivalent Treatment Shows Beneficial Effects in Old Healthy Dogs FIG. 20 shows the changes in values associated with blood components in old healthy dogs injected with 1000 mcg of pSP-HV-GHRH plasmid. Many blood component values were monitored two-weeks post injection including: WBC, RBC, HGB, lym %, total protein, albumin, globulin, A/G ratio, cholesterol, BUN, Creatinine, phosphorous, Calcium, glucose. Old dogs treated with the pSP-HV-GHRH plasmid therapy, had increased RBC hemoglobin and hematocrit levels two weeks post-injection compared with per-injected values. In addition, treated dogs have a significant decrease in urea levels, increased total protein levels and normal glucose levels. An increase in Ca/P ratio is an indication of bone remodeling.

Example 11

Treatment of Anemia

It is well known that erythroid cell number is primarily regulated by erythropoietin ("EPO") but is impacted by many growth factors. For example, hypophysectomized rats show low blood cell counts for erythroid, myeloid, and lymphoid cells, and there is extensive literature showing effects of both GH, and IGF-I on all hematopoietic lineages (Kurtz et al., 1990; Kurtz et al., 1982; Claustres et al., 1987). In polycytemia vera, patients present increased sensitivity of erythroid progenitor cells to IGF-I, elevated level of IGFBP-1 and consequently overproduction of red blood cells (Mirza et al., 1997; Correa et al., 1994). There is evidence to support the concept that IGF-I rather than EPO modulates erythropoiesis during accelerated growth or catabolism and thus manages a proportional increase in body mass and oxygen transport capacity (Kurtz et al., 1990). IGF-I is important factor regulating erythropoiesis in uremic patients (Urena et al., 1992). Moreover, the effect of treatment with recombinant human GH in anemic patients with panhypopituitarism is known. After the treatment with human GH plasma EPO levels double, with a concomitant increase of Hb concentration to normal levels. When the administration of human GH is interrupted, both plasma EPO levels and Hb concentrations decrease.

Figure 5:
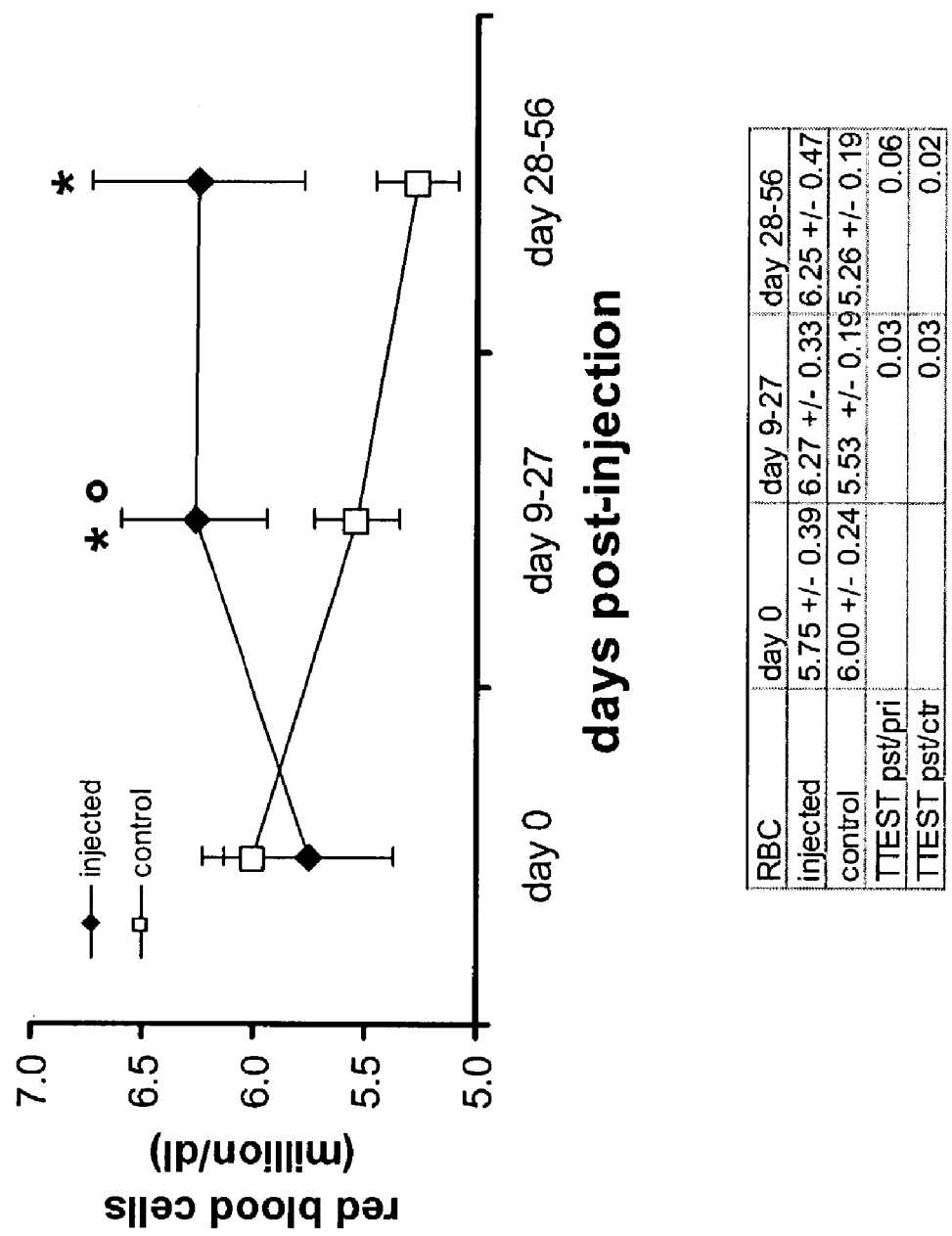
FIG. 5 shows the number of red blood cells in dogs with spontaneous malignancies treated with the GHRH plasmid therapy compared with control dogs with cancer.
Figure 6:
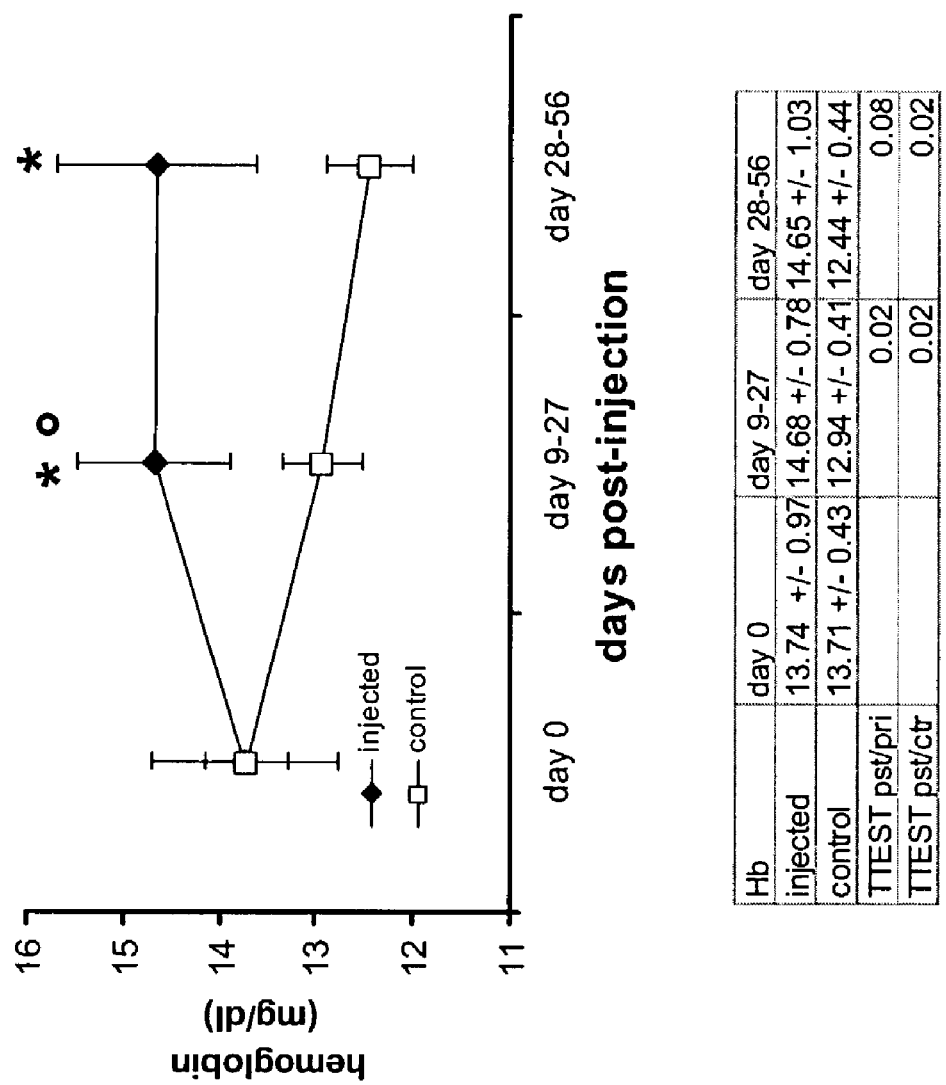
FIG. 6 shows hemoglobin values in dogs with spontaneous malignancies treated with the GHRH plasmid therapy compared with control dogs with cancer.
Figure 7:
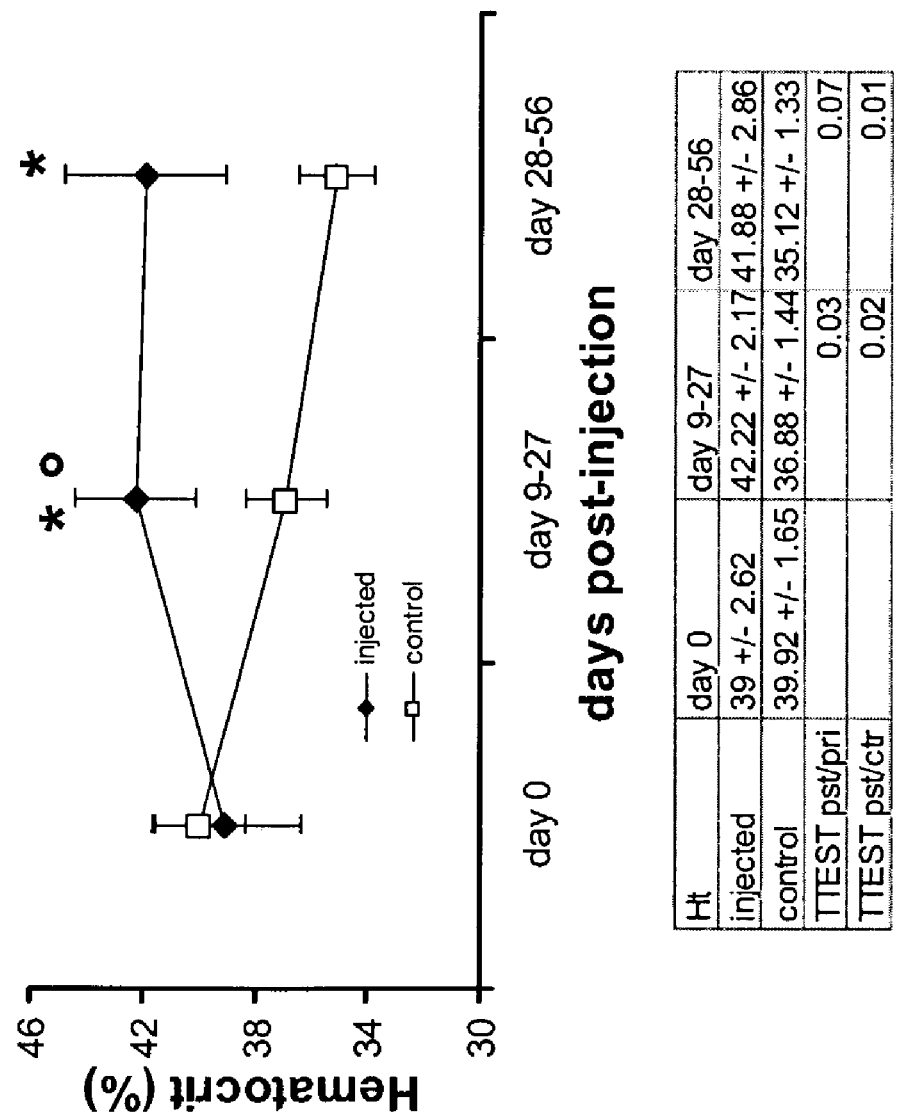
FIG. 7 shows hematocrit levels in dogs with spontaneous malignancies treated with the GHRH plasmid therapy compared with control dogs with cancer.
Figure 8:
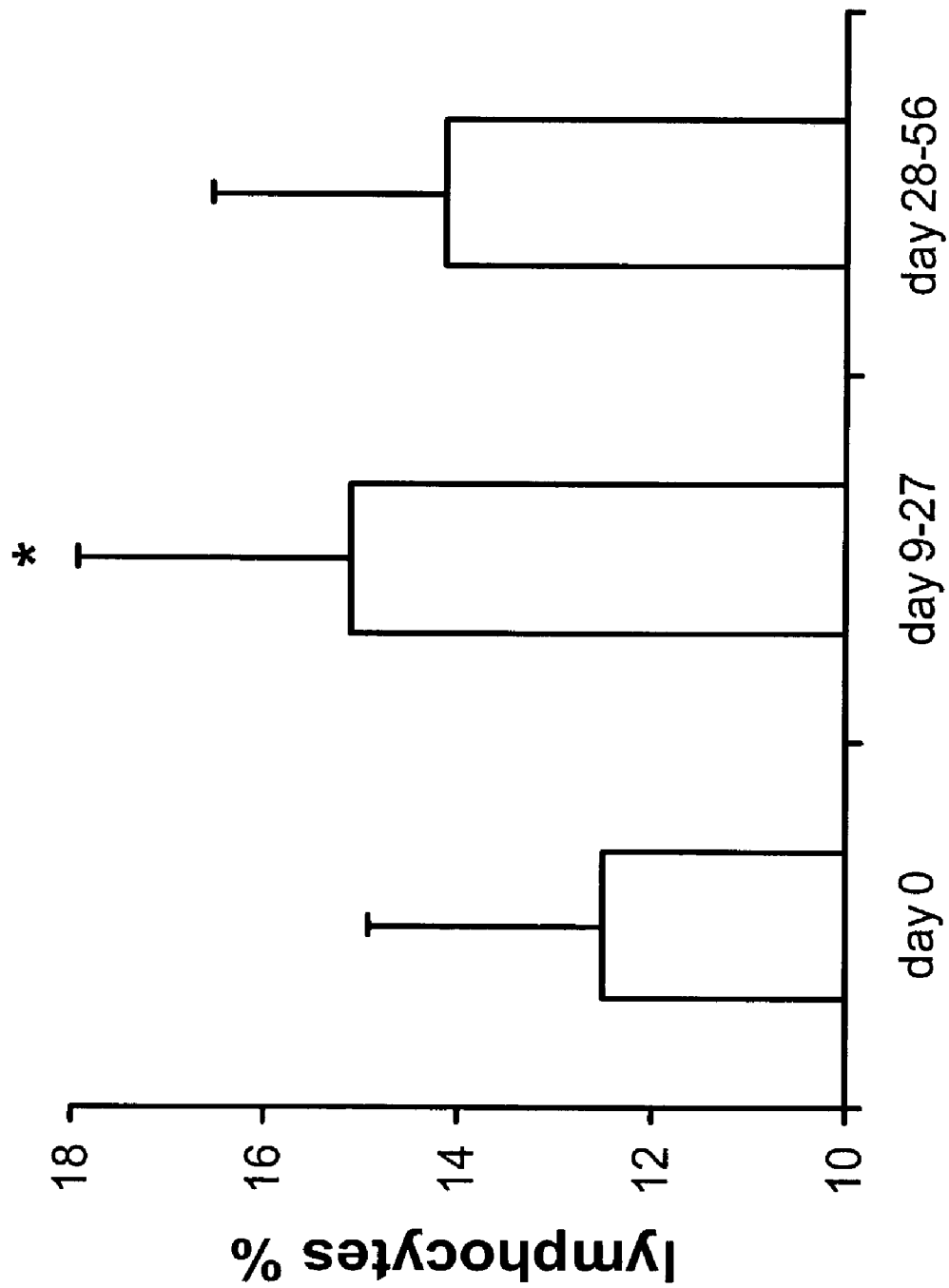
FIG. 8 shows the percentage of lymphocytes in dogs with spontaneous malignancies treated with the GHRH plasmid therapy compared with control dogs with cancer.

In injected dogs, a rapid correction of the anemia was obtained, as early as two weeks after the plasmid injection. Red blood cells (RBC) increased by 8.9%, 9-27 days and the normal values were maintained to 56 days post-injection ("pti"), compared with pre-injection ("pri") values (6.27±0.33, vs. 5.75±0.39, p<0.027), while the control group had a 6% decrease in their RBC levels (6.00±0.2 vs. 5.5±0.2) (p<0.006 compared to post-injection controls) in the same period of time (FIG. 5). Hemoglobin levels (FIG. 6) increased by 6.8% (14.68±0.78 vs. 13.74±0.97 g/l pti/pri), while the control group had a 5.7% decrease in the same period of time (12.9±0.4 vs. 13.7±0.4 g/l), p<0.01 compared to post-injection controls. Hematocrit levels (FIG. 7) increased significantly, by 8.26% (42.22±2.16 vs. 39±2.62%, p<0.032 pst/pri). In the same period, control values decreased by 7.6% (36.9±1.4 vs. 39.9±1.6%, p<0.012 compared with pst).

In a pre-clinical study on dog cancer patients, a rapid correction of the anemia was obtained, as early as two weeks after the plasmid injection. At the beginning of the study, the patients were in a catabolic state, with hemoglobin (Hb), hematocrit ("PVC") and red blood cell ("RBC") values significantly lower than normal dogs. After the plasmid injection, the dogs entered a rapid reverse stage, and became biochemically anabolic, mimicking a rapid growth process, as in the study described previously ("Growth Hormone Axis and the immune function") on young rats in the growth phase. Hb, PVC and RBC values increased with 10-25%, values significant statistically, and normalized two weeks after the beginning of the therapy. All values were within the normal limits throughout the experiment. Although not wanting to be bound by theory, our hypothesis is that stimulation of the GHRH—GH—IGF-I axis in a catabolic state is stimulating erytropoiesis most probably through stimulation of erytropoietin. When the patients are reversed to a normal anabolic state, the natural GH effect is to induce a slight degree of anemia. Nevertheless, these patients have cancer, and the natural course of the disease is towards catabolism. Patients will be maintained in balance by these contradictory mechanisms, thus the Hb, PVC and RBC values will be corrected to normal, but never exceed the upper normal limits, as shown in our studies.

Figure 9:
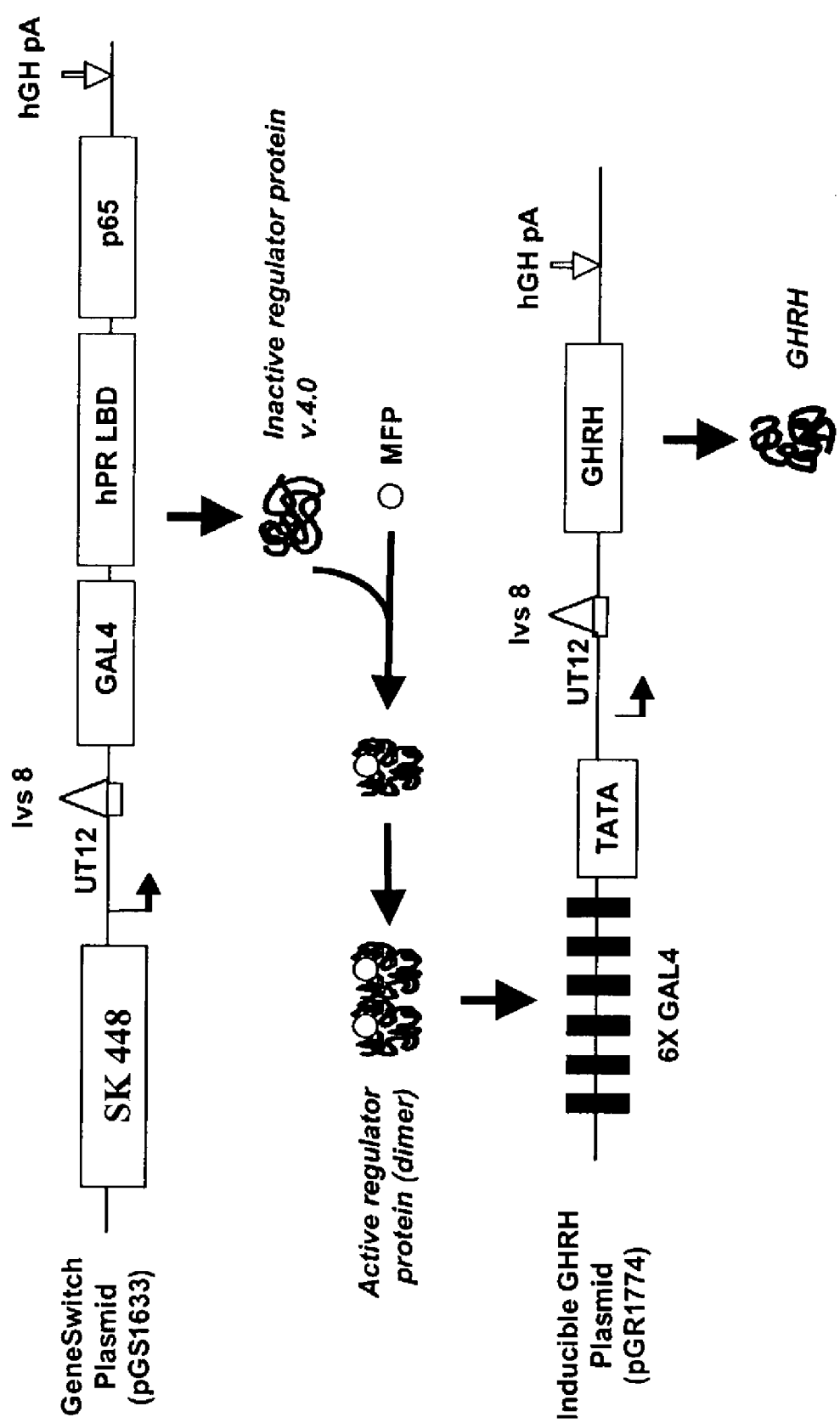
FIG. 9 shows a schematic of the mifepristone-dependent GHRH/GeneSwitch® system. Plasmid pl633 encodes for the GeneSwitch® regulator protein, that is a chimera of yeast GAL4 DNA binding domain ("GAL4"), truncated human progesterone receptor ligand-binding domain ("hPR LBD"), and activation domain from the p65 subunit of human NF-κB ("p65"). The protein is synthesized as an inactive monomer. Binding of mifepristone triggers a conformational change that leads to activation and dimerization. Activated homodimers bind to GAL4 sites in the inducible promoter and stimulate transcription of the GHRH gene.

Target gene expression also can be regulated by incorporating molecular switch technology as schematically diagramed in FIG. 9. A commercially available system for ligand-dependent induction of transgene expression has a registered trademark name of GeneSwitch®. The GeneSwitch® technology is based on a C-terminally truncated progesterone receptor that actually synthesized, but fails to bind to its natural agonist, progesterone. Instead the truncated progesterone receptor is only activated by anti-progestins, such as mifepristone ("MFP") (Vegeto et al., 1992; Xu et al., 1996). A similar system is used for the chimeric regulator protein of the GeneSwitch™ system, which consists of the ligand binding domain of the truncated human progesterone receptor that has been fused to the DNA binding domain of the yeast GAL4 protein (which binds a specific 17 bp recognition sequence) and a transcriptional activation domain from the p65 subunit of human NF-KB (Abruzzese et al., 1999). The gene for the GeneSwitch regulator protein was inserted into a myogenic expression vector, designated pGS1633, which is expressed constitutively under the control of a muscle-specific skeletal alpha-actin ("SK") promoter The GHRH plasmid, designated, p6xGal4/TATA-GHRH, or pGHRH1633 contains an inducible promoter that consists of six copies of the 17-mer Gal4 binding site fused to a minimal TATA box promoter. The GHRH coding sequence is a 228-bp fragment of super-porcine mutated GHRH cDNA, termed HV-GHRH (Draghia-Akli et al., 1999). The HV-GHRH molecule displays a high degree of stability in serum, with a half-life of 6 hours, versus the natural GHRH, that has a 6-12 minutes half-life. The muscle-specific GeneSwitch and inducible GHRH plasmids both have a 5' untranslated region that contains a synthetic intron, and a 3' untranslated region/poly (A) site that is from the human GH gene.

Example 12

Pharmacological aand Toxicological Effects of Exogenous GH Administration in Normal Animal Subjects Because porcine GH (pGH) is structurally identical to canine GH, pGH was used in different studies on dogs. In one of these studies, pGH was administered for a 14-weeks in dogs. Porcine GH caused increased body weight gain in mid- and high-dose groups (2.8 kg and 4.7 kg, respectively), compared to 0.4 kg and 0.8 kg in control and low-dose groups, respectively. In pGH-treated dogs, increased skin thickness seen grossly correlated histologically with increased dermal collagen. There was no gross or histomorphological evidence of edema. There were dose-related increased serum IGF-I levels (approximately 2-10-fold) that correlated with the elevated serum GH levels in pGH-treated dogs. Also, increased serum insulin levels through the mid dose were seen throughout the study. In high-dose dogs, the insulin levels remained elevated over 24 hr postdose. The serum glucose levels in fasted dogs remained within the control range and there was no chronic hyperglycemia based on glycosylated hemoglobin levels. Renal glomerular changes, significant polyuria with decreased urine specific gravity, and increased serum insulin levels suggested that the dogs had early insulin-resistant diabetes. There was minimal or no biologically significant effect of pGH on serum T3, T4, and cortisol levels in dogs. Other serum biochemical changes in pGH-treated dogs included decreased urea nitrogen and creatinine, and increased potassium, cholesterol, and triglycerides. Significant increases in serum calcium and phosphorous levels and alkaline phosphatase activity (bone isozyme) correlated with the histological changes in bone. In pGH-treated dogs, there was a dose-related normochromic, normocytic, nonregenerative anemia. The changes described above, except for the anemia, are related to catabolic effects of high doses of GH (Prahalada et al., 1998)

Example 13

Figure 10:
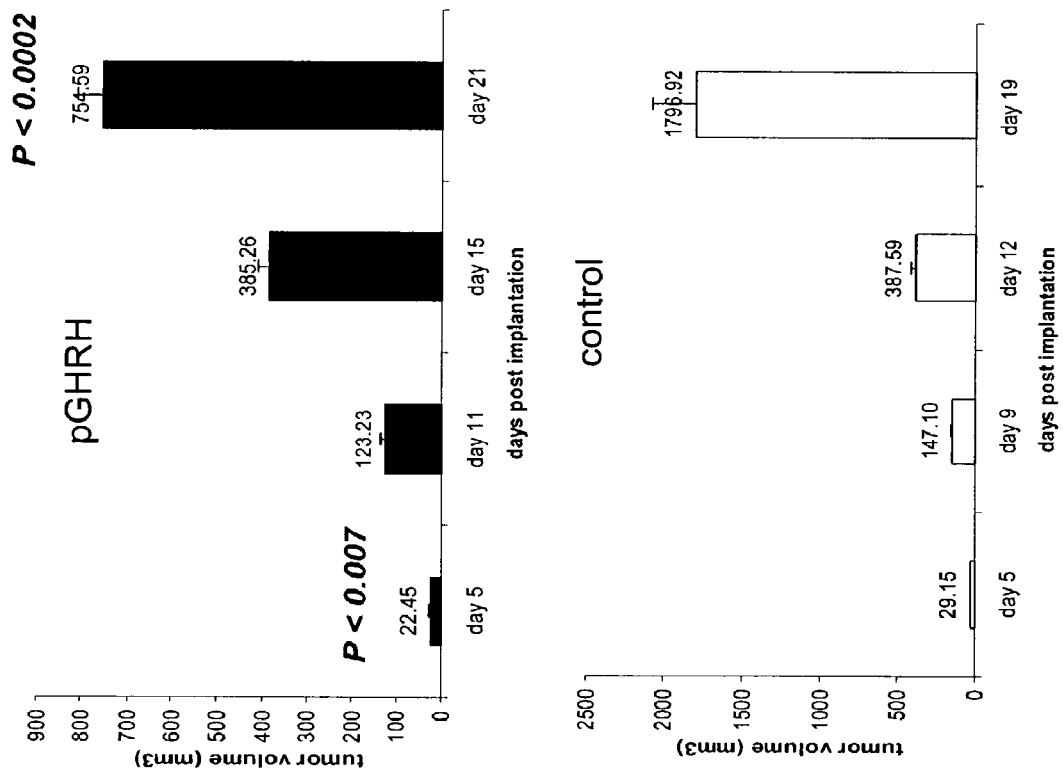
FIG. 10 shows tumor volume progression in immunocompetent C57/B16 mice that received 2×10$^6$ Lewis lung adenocarcinoma cells in their left flank. Treated animals received at 1 day after tumor cells implantation 20 micrograms of plasmid expressing human growth hormone releasing hormone, while controls received a control beta-galactosidase plasmid. GHRH treated tumor bearing animals have significantly slower tumor development and progression.
Figure 11:
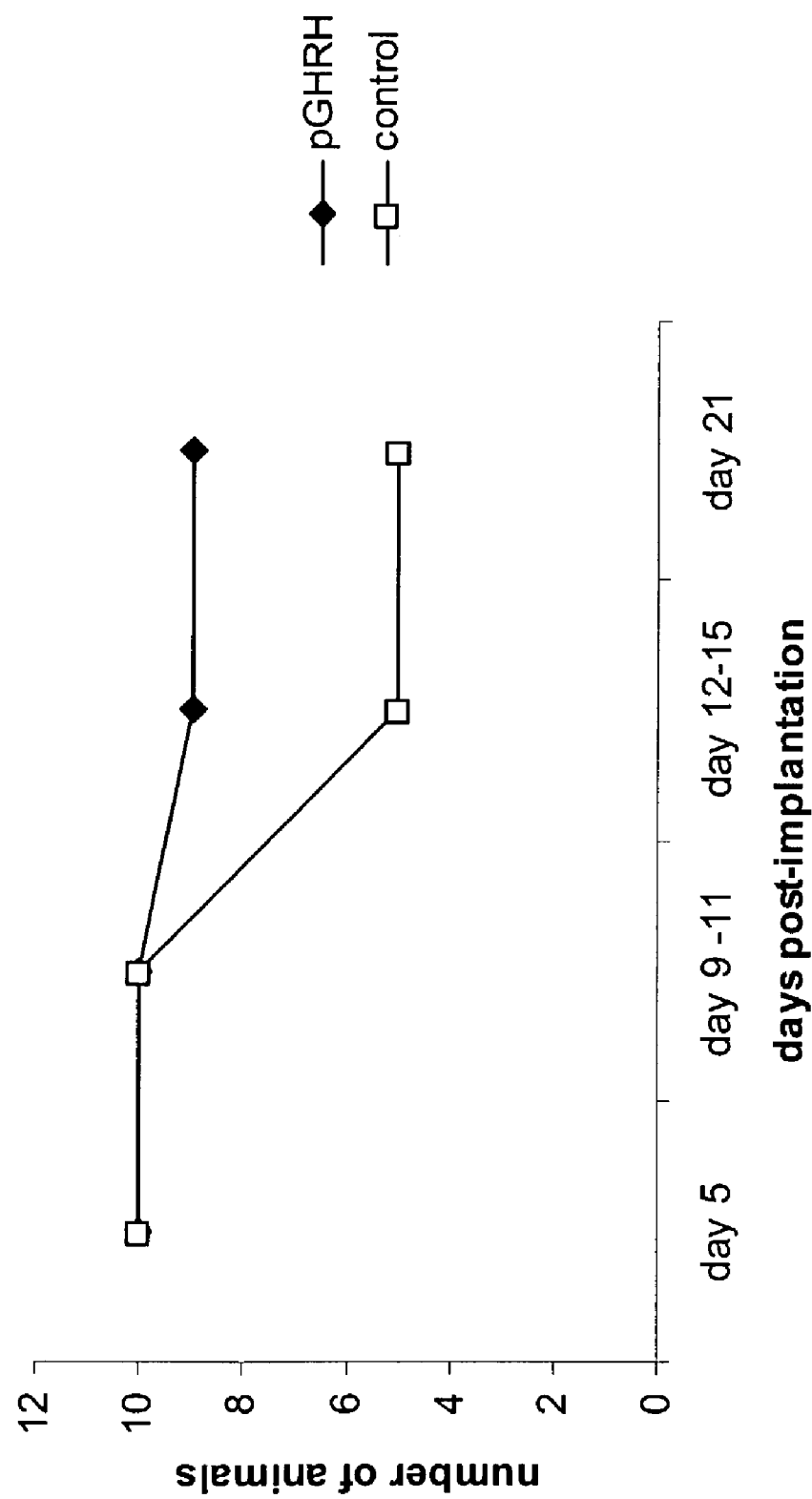
FIG. 11 shows survival time for immunocompetent C57/B16 mice that received 2×10$^6$ Lewis lung adenocarcinoma cells in their left flank. Treated animals received at 1 day after tumor cells implantation 20 micrograms of plasmid expressing human growth hormone releasing hormone, while controls received a control beta-galactosidase plasmid. GHRH-treated tumor bearing animals have increase survival.
Figure 12:
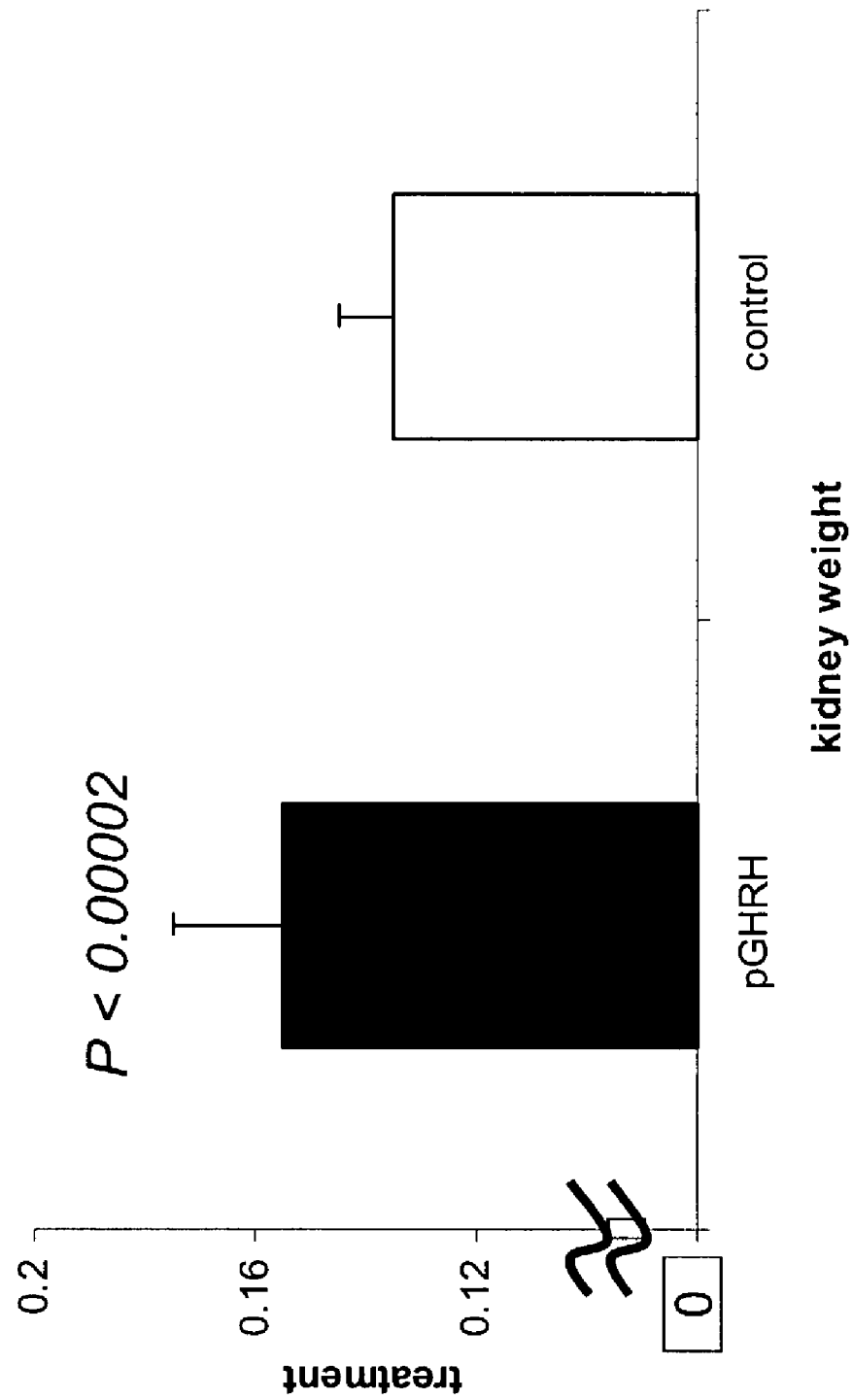
FIG. 12 shows kidney size for immunocompetent C57/B16 mice that received 2×10$^6$ Lewis lung adenocarcinoma cells in their left flank. Treated animals received at 1 day after tumor cells implantation 20 micrograms of plasmid expressing human growth hormone releasing hormone, while controls received a control beta-galactosidase plasmid. Control animals have significantly smaller kidney size, sign of kidney failure.

Plasmid Mediated GHRH Delivery Slows Tumor Growth, Prevents Kidney Failure and Increases Survivability in Tumor-Bearing Animals Immunocompetent C57/B16 mice or immunocompromised nude mice were injected with tumor lines (C57/B16 mice were implanted with a Lewis lung rat adenocarcinoma line, while the nude mice were implanted with a human lung small cell adenocarcinoma line). At 1 day after the tumor implantation, mice were treated with either constitutively active GHRH construct, an inducible GHRH construct or with a β-galactosidase expressing construct (as negative control). Tumor established slower (FIG. 10 and FIG. 14), and developed less rapidly in the GHRH treated animals. Consequently, GHRH treated animals survived longer (FIG. 11), and were less likely to develop kidney failure (FIG. 12), than controls. Metastases are less likely to develop (FIG. 13).

The invention described herein involves the utilization of several distinctive GHRH or biological equivalent nucleic acid sequences. Based upon the current understanding of protein-protein interactions, it is neither obvious nor possible to accurately speculate upon the in vivo parameters (e.g. half life, efficacy, post-translational modifications, etc.) of a GHRH sequence that contains a point mutation which alters a single amino acid in the polypeptide chain. However, based on the known art and the teachings of this specification, one skilled in the art would know how to perform the plasmid mediated supplementation experimentation(s), characterizing variations and permutations on any unique nucleic acid sequence in a specific tissue to accurately evaluate the in vivo effect on normal or chronic conditions within a living organism. Therefore, the utilization of the distinctive nucleic acid sequence encoding GHRH or biological equivalent thereof or corresponding recombinant protein as a plasmid-mediated method to treat anemia; increase total red blood cell mass; reverse the wasting;

reverse abnormal weight loss; treat immune dysfunction; reverse the suppression of lymphopoesis; and/or extend life expectancy for a chronically ill subject could not have been predicted based on speculation.

Although not wanting to be bound by theory, it is believed that an increase in GHRH will increase the GH levels sufficient to treat anemia; increase total red blood cell mass; reverse the wasting; reverse abnormal weight loss; treat immune dysfunction; reverse the suppression of lymphopoesis; or extend life expectancy for the chronically ill subject. Hormones (e.g. GHRH and GH) often contain a complex feedback-regulated pathway, which are further complicated by chronic conditions such as cancer or AIDS. Without direct experimentation of GHRH or biological equivalents used in plasmid-mediated supplementation or the teachings provided herein, beneficial therapy could not have been predicted by one skilled in the art to determine which concentrations of non-native encoded sequences will yield desired results. Ideal regulation of a nucleic acid sequence encoding GHRH or biological equivalent thereof is further complicated by the tissue used for plasmid mediated supplementation, and would not have been obvious to one skilled in the art without actual experimentations with the distinctive sequence in a particular tissue. The invention described herein contains the descriptions and results of essential experimentation that explored tissue specific and inducible regulation of distinctive nucleic acid sequences that encoded GHRH or biological equivalent thereof, which was not obvious based upon prior art. The present invention is a significant step forward in developing non-viral therapy for large animals, including humans. In order for nucleic acid-based therapies to be transferred from rodents to large mammals, and ultimately to humans, it was surprising that extremely low quantities of plasmid were effective. It is shown herein that as little as 0.2 mg plasmid delivered under the proper electroporation conditions had an important biological impact that reversed wasting, increase weight gain, and extend life in an ailing canine subject. This plasmid quantity was 100 fold lower than the theoretical one, and could not have been predicted from the relative doses used in rodents (in average 1 mg/kg).

The treatment of anemia, wasting, or immune dysfunction; the increase in total red blood cell mass; the reverse of abnormal weight loss; the reverse in the suppression of lymphopoesis; and/or the extension of life expectancy for a chronically ill subject are a consequence of the GHRH molecules present in the subjects circulation, regardless of the means of the delivery. For example, one would obtain the same effect by delivering the appropriate quantities of GHRH or an analog thereof by classical recombinant protein therapy or nucleic acid transfer. Accordingly, successful plasmid-mediated supplementation requires accurate delivery of encoded sequences to the cells of a subject that results in expression of the gene product at levels appropriate to produce a biological effect. The duration of treatment will extend through the course of the disease symptoms, and possibly continuously. Since the method to deliver nucleic acid sequences to the cells of a subject is highly dependent on specific diseases and the encoded gene, it could not have been predicted by one skilled in the art which method and conditions are appropriate without the teachings of this specification.

One skilled in the art readily appreciates that the present invention is well adapted to carry out the objectives and obtain the ends and advantages mentioned as well as those inherent therein. Methods, procedures, techniques, and kits described herein are presently representative of the preferred embodiments and are intended to be exemplary and are not intended as limitations of the scope. Changes therein and other uses will occur to those skilled in the art which are encompassed within the spirit of the invention or defined by the scope of the invention.

What is claimed:

1. A method of treating anemia in a patient, the anemia being caused by a decrease in red blood cell production, comprising:
    (a) administering into the muscle of the subject an effective amount of a plasmid expression construct encoding HV-GHRH (SEQ ID NO: 1), wherein the encoded HV-GHRH is operably linked to a SPc5-12 promoter of the plasmid expression construct, and wherein the plasmid expression construct is mixed with a transfection-facilitating polypeptide;
    (b) electroporating the muscle having the effective amount of plasmid expression construct encoding the HV-GHRH (SEQ ID NO: 1),
wherein the subject is a domesticated animal or human and wherein the HV-GHRH is biologically active and expressed in the muscle cells and released by the muscle cells causing a facilitation of growth hormone secretion and thereby causing increased red blood cell production, thereby treating the anemia.

* * * * *

SEQUENCE LISTING

<160> NUMBER OF SEQ ID NOS: 25

<210> SEQ ID NO 1
<211> LENGTH: 40
<212> TYPE: PRT
<213> ORGANISM: artificial sequence
<220> FEATURE:
<223> OTHER INFORMATION: This is a GHRH analog.

<400> SEQUENCE: 1

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 2
<211> LENGTH: 40
<212> TYPE: PRT
<213> ORGANISM: artificial sequence
<220> FEATURE:
<223> OTHER INFORMATION: This is a GHRH analog.

<400> SEQUENCE: 2

```
Tyr Ile Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 3
<211> LENGTH: 40
<212> TYPE: PRT
<213> ORGANISM: artificial sequence
<220> FEATURE:
<223> OTHER INFORMATION: This is a GHRH analog.

<400> SEQUENCE: 3

Tyr Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 4
<211> LENGTH: 40
<212> TYPE: PRT
<213> ORGANISM: artificial sequence
<220> FEATURE:
<223> OTHER INFORMATION: This is a GHRH analog.

<400> SEQUENCE: 4

Tyr Ala Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 5
<211> LENGTH: 44
<212> TYPE: PRT
<213> ORGANISM: artificial sequence
<220> FEATURE:
<223> OTHER INFORMATION: Artificial sequence for the (1-44)NH2

<400> SEQUENCE: 5

Thr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 6
<211> LENGTH: 40
<212> TYPE: PRT
<213> ORGANISM: artificial sequence
<220> FEATURE:
<223> OTHER INFORMATION: Artificial sequence for GHRH (1-40)OH.
<220> FEATURE:
<221> NAME/KEY: MISC_FEATURE
<222> LOCATION: (1)..(1)
<223> OTHER INFORMATION: Xaa at position 1 may be tyrosine, or histidine
<220> FEATURE:
<221> NAME/KEY: MISC_FEATURE
```

```
<222> LOCATION: (2)..(2)
<223> OTHER INFORMATION: Xaa at position 2 may be alanine, valine, or
      isoleucine.
<220> FEATURE:
<221> NAME/KEY: MISC_FEATURE
<222> LOCATION: (15)..(15)
<223> OTHER INFORMATION: Xaa at position 15 may be alanine, valine, or
      isoleucine.
<220> FEATURE:
<221> NAME/KEY: MISC_FEATURE
<222> LOCATION: (27)..(27)
<223> OTHER INFORMATION: Xaa at position 27 may be methionine, or
      leucine.
<220> FEATURE:
<221> NAME/KEY: MISC_FEATURE
<222> LOCATION: (28)..(28)
<223> OTHER INFORMATION: Xaa at position 28 may be serine or asparagine.

<400> SEQUENCE: 6

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Arg Asn Gln Glu Gln Gly Ala
        35                  40

<210> SEQ ID NO 7
<211> LENGTH: 323
<212> TYPE: DNA
<213> ORGANISM: artificial sequence
<220> FEATURE:
<223> OTHER INFORMATION: Nucleic acid sequence of a eukaryotic promoter
      c5-12.

<400> SEQUENCE: 7
cggccgtccg ccctcggcac catcctcacg acacccaaat atggcgacgg gtgaggaatg      60
gtggggagtt attttagag cggtgaggaa ggtgggcagg cagcaggtgt tggcgctcta     120
aaaataactc ccgggagtta tttttagagc ggaggaatgg tggacaccca aatatggcga    180
cggttcctca cccgtcgcca tatttgggtg tccgccctcg gccggggccg cattcctggg    240
ggccgggcgg tgctcccgcc cgcctcgata aaaggctccg gggccggcgg cggcccacga    300
gctacccgga ggagcgggag gcg                                            323

<210> SEQ ID NO 8
<211> LENGTH: 190
<212> TYPE: DNA
<213> ORGANISM: artificial sequence
<220> FEATURE:
<223> OTHER INFORMATION: Nucleic acid sequence of a human GH poly A
      tail.

<400> SEQUENCE: 8
gggtggcatc cctgtgaccc ctccccagtg cctctcctgg ccctggaagt tgccactcca      60
gtgcccacca gccttgtcct aataaaatta agttgcatca ttttgtctga ctaggtgtcc    120
ttctataata ttatggggtg gagggggtg gtatggagca agggcaagt tgggaagaca      180 acctgtaggg                                                            190

<210> SEQ ID NO 9
<211> LENGTH: 219
<212> TYPE: DNA
<213> ORGANISM: artificial sequence
<220> FEATURE:
<223> OTHER INFORMATION: cDNA for Porcine growth hormone releasing
      hormone
```

```
<400> SEQUENCE: 9
atggtgctct gggtgttctt ctttgtgatc ctcaccctca gcaacagctc ccactgctcc      60
ccacctcccc ctttgaccct caggatgcgg cggcacgtag atgccatctt caccaacagc     120
taccggaagg tgctggccca gctgtccgcc cgcaagctgc tccaggacat cctgaacagg     180
cagcagggag agaggaacca agagcaagga gcataatga                            219

<210> SEQ ID NO 10
<211> LENGTH: 40
<212> TYPE: PRT
<213> ORGANISM: artificial sequence
<220> FEATURE:
<223> OTHER INFORMATION: Amino acid sequence for porcine growth hormone
      releasing hormone.

<400> SEQUENCE: 10

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 11
<211> LENGTH: 3534
<212> TYPE: DNA
<213> ORGANISM: artificial sequence
<220> FEATURE:
<223> OTHER INFORMATION: Operatively linked components of the HV-GHRH
      plasmid.

<400> SEQUENCE: 11
gttgtaaaac gacggccagt gaattgtaat acgactcact ataggcgaa ttggagctcc        60 accgcggtgg cggccgtccg ccctcggcac catcctcacg cacccaaat atggcgacgg       120 gtgaggaatg gtgggagtt attttagag cggtgaggaa ggtgggcagg cagcaggtgt        180
tggcgctcta aaataactc ccgggagtta ttttagagc ggaggaatgg tggacaccca       240
aatatggcga cggttcctca cccgtcgcca tatttgggtg tccgccctcg gccggggccg      300
cattcctggg ggccgggcgg tgctcccgcc cgcctcgata aaaggctccg gggccggcgg      360
cggcccacga gctacccgga ggagcgggag gcgccaagct ctagaactag tggatcccaa      420
ggcccaactc cccgaaccac tcagggtcct gtggacagct cacctagctg ccatggtgct      480
ctgggtgttc ttctttgtga tcctcaccct cagcaacagc tcccactgct ccccacctcc      540
ccctttgacc ctcaggatgc ggcggcacgt agatgccatc ttcaccaaca gctaccggaa      600
ggtgctggcc cagctgtccg cccgcaagct gctccaggac atcctgaaca ggcagcaggg      660
agagaggaac caagagcaag gagcataatg actgcaggaa ttcgatatca agcttatcgg      720
ggtggcatcc ctgtgacccc tccccagtgc ctctcctggc cctggaagtt gccactccag      780
tgcccaccag ccttgtccta ataaaattaa gttgcatcat tttgtctgac taggtgtcct      840
tctataatat tatggggtgg aggggggtgg tatggagcaa ggggcaagtt gggaagacaa      900
cctgtagggc ctgcggggtc tattgggaac caagctggag tgcagtggca caatcttggc      960
tcactgcaat ctccgcctcc tgggttcaag cgattctcct gcctcagcct cccgagttgt     1020
tgggattcca ggcatgcatg accaggctca gctaatttt gttttttgg tagagacggg       1080 gtttcaccat attggccagg ctggtctcca actcctaatc tcaggtgatc tacccacctt     1140
```

-continued

```
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga ggggggccc ggtaccagct    1380 tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagacacg    2160
acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact tcgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
```

```
                                              -continued
gatgtgctgc aaggcgatta agttgggtaa cgccagggtt ttcccagtca cgac        3534

<210> SEQ ID NO 12
<211> LENGTH: 3534
<212> TYPE: DNA
<213> ORGANISM: artificial sequence
<220> FEATURE:
<223> OTHER INFORMATION: Operatively linked components of the TI-GHRH
      plasmid.

<400> SEQUENCE: 12
gttgtaaaac gacggccagt gaattgtaat acgactcact atagggcgaa ttggagctcc    60
accgcggtgg cggccgtccg ccctcggcac catcctcacg acacccaaat atggcgacgg   120
gtgaggaatg gtggggagtt atttttagag cggtgaggaa ggtgggcagg cagcaggtgt   180
tggcgctcta aaataactcc cgggagttat tttttagagc ggaggaatgg tggacaccca   240
aatatggcga cggttcctca cccgtcgcca tatttgggtg tccgccctcg gccggggccg   300
cattcctggg ggccgggcgg tgctcccgcc cgcctcgata aaggctccg gggccggcgg   360 cggcccacga gctacccgga ggagcgggag gcgccaagct ctagaactag tggatcccaa   420
ggcccaactc cccgaaccac tcagggtcct gtggacagtc cacctagctg ccatggtgct   480
ctgggtgttc ttctttgtga tcctcaccct cagcaacagc tcccactgct ccccacctcc   540 cccttttgacc ctcaggatgc ggcggtatat cgatgccatc ttcaccaaca gctaccggaa   600
ggtgctggcc cagctgtccg cccgcaagct gctccaggac atcctgaaca gcagcaggg   660 agagaggaac caagagcaag gagcataatg actgcaggaa ttcgatatca agcttatcgg   720
ggtggcatcc ctgtgacccc tccccagtgc ctctcctggc cctggaagtt gccactccag   780
tgcccaccag ccttgtccta ataaaattaa gttgcatcat tttgtctgac taggtgtcct   840
tctataatat tatggggtgg aggggggtgg tatggagcaa ggggcaagtt gggaagacaa   900
cctgtagggc ctgcggggtc tattgggaac caagctggag tgcagtggca caatcttggc   960
tcactgcaat ctccgcctcc tgggttcaag cgattctcct gcctcagcct cccgagttgt  1020
tgggattcca ggcatgcatg accaggctca gctaattttt gtttttttgg tagagacggg  1080
gtttcaccat attggccagg ctggtctcca actcctaatc tcaggtgatc tacccacctt  1140
ggcctcccaa attgctggga ttacaggcgt gaaccactgc tcccttccct gtccttctga  1200
ttttaaaata actataccag caggaggacg tccagacaca gcataggcta cctggccatg  1260
cccaaccggt gggacatttg agttgcttgc ttggcactgt cctctcatgc gttgggtcca  1320
ctcagtagat gcctgttgaa ttcgataccg tcgacctcga gggggggccc ggtaccagct  1380
tttgttccct ttagtgaggg ttaatttcga gcttggcgta atcatggtca tagctgtttc  1440
ctgtgtgaaa ttgttatccg ctcacaattc cacacaacat acgagccgga agcataaagt  1500
gtaaagcctg gggtgcctaa tgagtgagct aactcacatt aattgcgttg cgctcactgc  1560
ccgctttcca gtcgggaaac ctgtcgtgcc agctgcatta atgaatcggc caacgcgcgg  1620
ggagaggcgg tttgcgtatt gggcgctctt ccgcttcctc gctcactgac tcgctgcgct  1680
cggtcgttcg gctgcggcga gcggtatcag ctcactcaaa ggcggtaata cggttatcca  1740
cagaatcagg ggataacgca ggaaagaaca tgtgagcaaa aggccagcaa aaggccagga  1800
accgtaaaaa ggccgcgttg ctggcgtttt tccataggct ccgcccccct gacgagcatc  1860
acaaaaatcg acgctcaagt cagaggtggc gaaacccgac aggactataa agataccagg  1920
cgtttccccc tggaagctcc ctcgtgcgct ctcctgttcc gaccctgccg cttaccggat  1980
```

-continued

```
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagcacg     2160 acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt ttttttgttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact tcgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt ttcccagtca cgac          3534
```

<210> SEQ ID NO 13
<211> LENGTH: 3534
<212> TYPE: DNA
<213> ORGANISM: artificial sequence
<220> FEATURE:
<223> OTHER INFORMATION: Operatively linked components of the TV-GHRH plasmid.

<400> SEQUENCE: 13

```
gttgtaaaac gacggccagt gaattgtaat acgactcact ataggggcgaa ttggagctcc    60 accgcggtgg cggccgtccg ccctcggcac catcctcacg acacccaaat atggcgacgg    120
gtgaggaatg gtggggagtt attttttagag cggtgaggaa ggtgggcagg cagcaggtgt    180
tggcgctcta aaaataactc ccgggagtta ttttttagagc ggaggaatgg tggacaccca    240 aatatgcgcga cggttcctca cccgtcgcca tatttgggtg tccgccctcg gccggggccg    300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
```

```
ctgggtgttc ttctttgtga tcctcaccct cagcaacagc tcccactgct ccccacctcc    540
cccctttgacc ctcaggatgc ggcggtatgt agatgccatc ttcaccaaca gctaccggaa    600
ggtgctggcc cagctgtccg cccgcaagct gctccaggac atcctgaaca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt   1020
tgggattcca ggcatgcatg accaggctca gctaattttt gttttttgg tagagacggg    1080
gtttcaccat attggccagg ctggtctcca actcctaatc tcaggtgatc tacccacctt   1140
ggcctcccaa attgctggga ttacaggcgt gaaccactgc tcccttccct gtccttctga   1200
ttttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga gggggggccc ggtaccagct   1380
tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
cagaatcagg ggataacgca ggaaagaaca tgtgagcaaa aggccagcaa aaggccagga   1800
accgtaaaaa ggccgcgttg ctggcgtttt tccataggct ccgcccccct gacgagcatc   1860
acaaaaatcg acgctcaagt cagaggtggc gaaacccgac aggactataa agataccagg   1920
cgtttccccc tggaagctcc ctcgtgcgct ctcctgttcc gaccctgccg cttaccggat   1980
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagcacg    2160
acttatcgcc actggcagca gccactggta acaggattag cagagcgagg tatgtaggcg   2220
gtgctacaga gttcttgaag tggtggccta actacggcta cactagaaga acagtatttg   2280
gtatctgcgc tctgctgaag ccagttacct tcggaaaaag agttggtagc tcttgatccg   2340
gcaaacaaac caccgctggt agcggtggtt tttttgtttg caagcagcag attacgcgca   2400
gaaaaaaagg atctcaagaa gatcctttga tcttttctac ggggtctgac gctcagaaga   2460
actcgtcaag aaggcgatag aaggcgatgc gctgcgaatc gggagcggcg ataccgtaaa   2520
gcacgaggaa gcggtcagcc cattcgccgc caagctcttc agcaatatca cgggtagcca   2580
acgctatgtc ctgatagcgg tccgccacac ccagccggcc acagtcgatg aatccagaaa   2640
agcggccatt ttccaccatg atattcggca agcaggcatc gccatgggtc acgacgagat   2700
cctcgccgtc gggcatgcgc gccttgagcc tggcgaacag ttcggctggc gcgagcccct   2760
gatgctcttc gtccagatca tcctgatcga caagaccggc ttccatccga gtacgtgctc   2820
gctcgatgcg atgtttcgct tggtggtcga atgggcaggt agccggatca gcgtatgca   2880
```

```
gccgccgcat tgcatcagcc atgatggata ctttctcggc aggagcaagg tgagatgaca    2940
ggagatcctg ccccggcact tcgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt tcccagtca cgac           3534
```

<210> SEQ ID NO 14
<211> LENGTH: 3534
<212> TYPE: DNA
<213> ORGANISM: artificial sequence
<220> FEATURE:
<223> OTHER INFORMATION: Operatively linked components of the 15/27/28
    GHRH plasmid.

<400> SEQUENCE: 14

```
gttgtaaaac gacggccagt gaattgtaat acgactcact atagggcgaa ttggagctcc      60
accgcggtgg cggccgtccg ccctcggcac catcctcacg acacccaaat atggcgacgg     120
gtgaggaatg gtggggagtt attttttagag cggtgaggaa ggtgggcagg cagcaggtgt    180
tggcgctcta aaaataactc ccgggagtta tttttagagc ggaggaatgg tggacaccca    240
aatatggcga cggttcctca cccgtcgcca tatttgggtg tccgccctcg gccggggccg    300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
ctgggtgttc ttctttgtga tcctcaccct cagcaacagc tcccactgct ccccacctcc    540
cccctttgacc ctcaggatgc ggcggtatat cgatgccatc ttcaccaaca gctaccggaa    600
ggtgctggcc cagctgtccg cccgcaagct gctccaggac atcctgaaca ggcagcaggg    660
agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg agggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt    1020
tgggattcca ggcatgcatg accaggctca gctaattttt gtttttttgg tagagacggg    1080
gtttcaccat attggccagg ctggtctcca actcctaatc tcaggtgatc tacccacctt    1140
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga gggggggccc ggtaccagct    1380
```

-continued

```
tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagcacg    2160 acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt ttcccagtca cgac          3534
```

<210> SEQ ID NO 15
<211> LENGTH: 3534
<212> TYPE: DNA
<213> ORGANISM: artificial sequence
<220> FEATURE:

<223> OTHER INFORMATION: Entire plasmid sequence for wildtype GHRH.

<400> SEQUENCE: 15

| | | | | | |
|---|---|---|---|---|---|
| gttgtaaaac | gacggccagt | gaattgtaat | acgactcact | ataggg cgaa | ttggagctcc | 60 |
| accgcggtgg | cggccgtccg | ccctcggcac | catcctcacg | acacccaaat | atggcgacgg | 120 |
| gtgaggaatg | gtggggagtt | attttagag | cggtgaggaa | ggtgggcagg | cagcaggtgt | 180 |
| tggcgctcta | aaataactc | ccgggagtta | tttttagagc | ggaggaatgg | tggacaccca | 240 |
| aatatggcga | cggttcctca | cccgtcgcca | tatttgggtg | tccgccctcg | gccggggccg | 300 |
| cattcctggg | ggccgggcgg | tgctcccgcc | cgcctcgata | aaaggctccg | gggccggcgg | 360 |
| cggcccacga | gctacccgga | ggagcgggag | gcgccaagct | ctagaactag | tggatcccaa | 420 |
| ggcccaactc | cccgaaccac | tcaggtcct | gtggacagct | cacctagctg | ccatggtgct | 480 |
| ctgggtgttc | ttctttgtga | tcctcaccct | cagcaacagc | tcccactgct | ccccacctcc | 540 |
| ccctttgacc | ctcaggatgc | ggcggtatgc | agatgccatc | ttcaccaaca | gctaccggaa | 600 |
| ggtgctgggc | cagctgtccg | cccgcaagct | gctccaggac | atcatgagca | ggcagcaggg | 660 |
| agagaggaac | caagagcaag | gagcataatg | actgcaggaa | ttcgatatca | agcttatcgg | 720 |
| ggtggcatcc | ctgtgacccc | tccccagtgc | ctctcctggc | cctggaagtt | gccactccag | 780 |
| tgcccaccag | cctgtccta | ataaaattaa | gttgcatcat | tttgtctgac | taggtgtcct | 840 |
| tctataatat | tatgggtgg | aggggggtgg | tatggagcaa | ggggcaagtt | gggaagacaa | 900 |
| cctgtagggc | ctgcggggtc | tattgggaac | caagctggag | tgcagtggca | caatcttggc | 960 |
| tcactgcaat | ctccgcctcc | tgggttcaag | cgattctcct | gcctcagcct | cccgagttgt | 1020 |
| tgggattcca | ggcatgcatg | accaggctca | gctaattttt | gtttttttgg | tagagacggg | 1080 |
| gttcaccat | attggccagg | ctggtctcca | actcctaatc | tcaggtgatc | tacccacctt | 1140 |
| ggcctcccaa | attgctggga | ttacaggcgt | gaaccactgc | tcccttccct | gtccttctga | 1200 |
| ttttaaaata | actataccag | caggaggacg | tccagacaca | gcataggcta | cctggccatg | 1260 |
| cccaaccggt | gggacatttg | agttgcttgc | ttggcactgt | cctctcatgc | gttgggtcca | 1320 |
| ctcagtagat | gcctgttgaa | ttcgataccg | tcgacctcga | gggggggccc | ggtaccagct | 1380 |
| tttgttccct | ttagtgaggg | ttaatttcga | gcttggcgta | atcatggtca | tagctgtttc | 1440 |
| ctgtgtgaaa | ttgttatccg | ctcacaattc | cacacaacat | acgagccgga | agcataaagt | 1500 |
| gtaaagcctg | gggtgcctaa | tgagtgagct | aactcacatt | aattgcgttg | cgctcactgc | 1560 |
| ccgctttcca | gtcgggaaac | ctgtcgtgcc | agctgcatta | atgaatcggc | caacgcgcgg | 1620 |
| ggagaggcgg | tttgcgtatt | gggcgctctt | ccgcttcctc | gctcactgac | tcgctgcgct | 1680 |
| cggtcgttcg | gctgcggcga | gcggtatcag | ctcactcaaa | ggcggtaata | cggttatcca | 1740 |
| cagaatcagg | ggataacgca | ggaaagaaca | tgtgagcaaa | aggccagcaa | aaggccagga | 1800 |
| accgtaaaaa | ggccgcgttg | ctggcgtttt | tccataggct | ccgcccccct | gacgagcatc | 1860 |
| acaaaaatcg | acgctcaagt | cagaggtggc | gaaacccgac | aggactataa | agataccagg | 1920 |
| cgtttccccc | tggaagctcc | ctcgtgcgct | ctcctgttcc | gaccctgccg | cttaccggat | 1980 |
| acctgtccgc | ctttctccct | tcgggaagcg | tggcgctttc | tcatagctca | cgctgtaggt | 2040 |
| atctcagttc | ggtgtaggtc | gttcgctcca | agctgggctg | tgtgcacgaa | ccccccgttc | 2100 |
| agcccgaccg | ctgcgcctta | tccggtaact | atcgtcttga | gtccaacccg | gtaagacacg | 2160 |
| acttatcgcc | actggcagca | gccactggta | acaggattag | cagagcgagg | tatgtaggcg | 2220 |
| gtgctacaga | gttcttgaag | tggtggccta | actacggcta | cactagaaga | acagtatttg | 2280 |

-continued

```
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt ttcccagtca cgac          3534
```

<210> SEQ ID NO 16
<211> LENGTH: 4260
<212> TYPE: DNA
<213> ORGANISM: Artificial sequence
<220> FEATURE:
<223> OTHER INFORMATION: Sequence for the pSP-SEAP cDNA construct

<400> SEQUENCE: 16

```
ggccgtccgc cttcggcacc atcctcacga cacccaaata tggcgacggg tgaggaatgg     60
tggggagtta ttttagagc ggtgaggaag gtgggcaggc agcaggtgtt ggcgctctaa    120
aaataactcc cgggagttat ttttagagcg gaggaatggt ggacacccaa atatggcgac    180
ggttcctcac ccgtcgccat atttgggtgt ccgccctcgg ccggggccgc attcctgggg    240
gccgggcggt gctccgccc gcctcgataa aaggctccgg ggcggcggc ggcccacgag    300 ctacccggag gagcgggagg cgccaagctc tagaactagt ggatccccg gctgcagga    360 attcgatatc aagcttcgaa tcgcgaattc gcccaccatg ctgctgctgc tgctgctgct    420
gggcctgagg ctacagctct ccctgggcat catcccagtt gaggaggaga acccggactt    480
ctggaaccgc gaggcagccg aggccctggg tgccgccaag aagctgcagc ctgcacagac    540
agccgccaag aacctcatca tcttcctggg cgatgggatg ggggtgtcta cggtgacagc    600
tgccaggatc ctaaaagggc agaagaagga caaactgggg cctgagatac ccctggccat    660
ggaccgcttc ccatatgtgg ctctgtccaa gacatacaat gtagacaaac atgtgccaga    720
cagtggagcc acagccacgg cctacctgtg cggggtcaag gcaacttcc agaccattgg    780
```

```
cttgagtgca gccgcccgct taaccagtg caacacgaca cgcggcaacg aggtcatctc      840
cgtgatgaat cgggccaaga aagcagggaa gtcagtggga gtggtaacca ccacacgagt     900
gcagcacgcc tcgccagccg gcacctacgc ccacacggtg aaccgcaact ggtactcgga     960
cgccgacgtg cctgcctcgg cccgccagga ggggtgccag gacatcgcta cgcagctcat    1020
ctccaacatg gacattgacg tgatcctagg tggaggccga aagtacatgt ttcgcatggg    1080
aaccccagac cctgagtacc cagatgacta cagccaaggt gggaccaggc tggacgggaa    1140
gaatctggtg caggaatggc tggcgaagcg ccagggtgcc cggtatgtgt ggaaccgcac    1200
tgagctcatg caggcttccc tggacccgtc tgtgacccat ctcatgggtc tctttgagcc    1260
tggagacatg aaatacgaga tccaccgaga ctccacactg gaccctcccc tgatggagat    1320
gacagaggct gccctgcgcc tgctgagcag gaaccccgc ggcttcttcc tcttcgtgga    1380
gggtggtcgc atcgaccatg gtcatcatga agcagggct taccgggcac tgactgagac    1440
gatcatgttc gacgacgcca ttgagagggc gggccagctc accagcgagg aggacacgct    1500
gagcctcgtc actgccgacc actcccacgt cttctccttc ggaggctacc ccctgcgagg    1560
gagctccatc ttcgggctgg cccctggcaa ggcccgggac aggaaggcct acacggtcct    1620
cctatacgga aacggtccag gctatgtgct caaggacggc gcccggccgg atgttaccga    1680
gagcgagagc gggagccccg agtatcggca gcagtcagca gtgcccctgg acgaagagac    1740
ccacgcaggc gaggacgtgg cggtgttcgc gcgcggcccg caggcgcacc tggttcacgg    1800
cgtgcaggag cagaccttca tagcgcacgt catggccttc gccgcctgcc tggagcccta    1860
caccgcctgc gacctggcgc ccccgccgg caccaccgac gccgcgcacc cgggttactc    1920
tagagtcggg gcgccggcc gcttcgagca gacatgataa gatacattga tgagtttgga    1980
caaaccacaa ctagaatgca gtgaaaaaaa tgctttattt gtgaaatttg tgatgctatt    2040
gctttatttg taaccattat aagctgcaat aaacaagtta acaacaacaa ttgcattcat    2100
tttatgtttc aggttcaggg ggaggtgtgg gaggttttt aaagcaagta aaacctctac    2160
aaatgtggta aaatcgataa ggatccgtcg accgatgccc ttgagagcct caacccagt    2220
cagctccttc cggtgggcgc ggggcatgac tatcgtcgcc gcacttatga ctgtcttctt    2280
tatcatgcaa ctcgtaggac aggtgccggc agcgctcttc cgcttcctcg ctcactgact    2340
cgctgcgctc ggtcgttcgg ctgcggcgag cggtatcagc tcactcaaag gcggtaatac    2400
ggttatccac agaatcaggg gataacgcag gaaagaacat gtgagcaaaa ggccagcaaa    2460
aggccaggaa ccgtaaaaag gccgcgttgc tggcgttttt ccataggctc cgcccccctg    2520
acgagcatca aaaaatcga cgctcaagtc agaggtggcg aaacccgaca ggactataaa    2580
gataccaggc gtttccccct ggaagctccc tcgtgcgctc tcctgttccg accctgccgc    2640
ttaccggata cctgtccgcc tttctccctt cgggaagcgt ggcgctttct catagctcac    2700
gctgtaggta tctcagttcg gtgtaggtcg ttcgctccaa gctgggctgt gtgcacgaac    2760
cccccgttca gcccgaccgc tgcgccttat ccggtaacta tcgtcttgag tccaacccgg    2820
taagacacga cttatcgcca ctggcagcag ccactggtaa caggattagc agagcgaggt    2880
atgtaggcgg tgctacagag ttcttgaagt ggtggcctaa ctacggctac actagaagga    2940
cagtatttgg tatctgcgct ctgctgaagc cagttacctt cggaaaaaga gttggtagct    3000
cttgatccgg caaacaaacc accgctggta gcggtggttt ttttgtttgc aagcagcaga    3060
ttacgcgcag aaaaaaagga tctcaagaag atcctttgat cttttctacg gggtctgacg    3120
ctcagtggaa cgaaaactca cgttaaggga ttttggtcat gagattatca aaaaggatct    3180
```

-continued

```
tcacctagat cctttttaaat taaaaatgaa gttttaaatc aatctaaagt atatatgagt    3240
aaacttggtc tgacagttac caatgcttaa tcagtgaggc acctatctca gcgatctgtc    3300
tatttcgttc atccatagtt gcctgactcc cgtcgtgta gataactacg atacgggagg    3360
gcttaccatc tggccccagt gctgcaatga taccgcgaga cccacgctca ccggctccag    3420
atttatcagc aataaaccag ccagccggaa gggccgagcg cagaagtggt cctgcaactt    3480
tatccgcctc catccagtct attaattgtt gccgggaagc tagagtaagt agttcgccag    3540
ttaatagttt gcgcaacgtt gttgccattg ctacaggcat cgtggtgtca cgctcgtcgt    3600
ttggtatggc ttcattcagc tccggttccc aacgatcaag gcgagttaca tgatccccca    3660
tgttgtgcaa aaaagcggtt agctccttcg gtcctccgat cgttgtcaga agtaagttgg    3720
ccgcagtgtt atcactcatg gttatggcag cactgcataa ttctcttact gtcatgccat    3780
ccgtaagatg cttttctgtg actggtgagt actcaaccaa gtcattctga aatagtgta    3840 tgcggcgacc gagttgctct tgcccggcgt caatacggga taataccgcg ccacatagca    3900
gaactttaaa agtgctcatc attggaaaac gttcttcggg gcgaaaactc tcaaggatct    3960
taccgctgtt gagatccagt tcgatgtaac ccactcgtgc acccaactga tcttcagcat    4020
cttttacttt caccagcgtt tctgggtgag caaaaacagg aaggcaaaat gccgcaaaaa    4080
agggaataag ggcgacacgg aaatgttgaa tactcatact cttccttttt caatattatt    4140
gaagcattta tcaggttat tgtctcatga gcggatacat atttgaatgt atttagaaaa    4200
ataaacaaat agggggttccg cgcacatttc cccgaaaagt gccacctgac gcgccctgta    4260
```

<210> SEQ ID NO 17
<211> LENGTH: 2710
<212> TYPE: DNA
<213> ORGANISM: artificial sequence
<220> FEATURE:
<223> OTHER INFORMATION: An analog GHRH sequence codon optimized for mouse.

<400> SEQUENCE: 17

```
tgtaatacga ctcactatag ggcgaattgg agctccaccg cggtggcggc cgtccgccct     60
cggcaccatc ctcacgacac ccaaatatgg cgacgggtga ggaatggtgg ggagttattt    120
ttagagcggt gaggaaggtg ggcaggcagc aggtgttggc gctctaaaaa taactcccgg    180
gagttatttt tagagcggag gaatggtgga cacccaaata tggcgacggt tcctcacccg    240
tcgccatatt tgggtgtccg ccctcggccg gggccgcatt cctgggggcc gggcggtgct    300
cccgcccgcc tcgataaaag gctccggggc cggcggcggc ccacgagcta cccggaggag    360
cgggaggcgc caagcggatc ccaaggccca actccccgaa ccactcaggg tcctgtggac    420
agctcaccta gctgccatgg tgctctgggt gctctttgtg atcctcatcc tcaccagcgg    480
cagccactgc agcctgcctc ccagccctcc cttcaggatg cagaggcacg tggacgccat    540
cttcaccacc aactacagga agctgctgag ccagctgtac gccaggaagg tgatccagga    600
catcatgaac aagcagggcg agaggatcca ggagcagagg gccaggctga gctgataagc    660
ttatcggggt ggcatccctg tgaccccctcc ccagtgcctc tcctggccct ggaagttgcc    720
actccagtgc ccaccagcct tgtcctaata aaattaagtt gcatcatttt gtctgactag    780
gtgtccttct ataatattat ggggtggagg gggtggtat ggagcaaggg gcaagttggg    840
aagcaaacct gtagggctcg agggggggcc cggtaccagc ttttgttccc tttagtgagg    900
gttaatttcg agcttggtct tccgcttcct cgctcactga ctcgctgcgc tcggtcgttc    960
```

```
ggctgcggcg agcggtatca gctcactcaa aggcggtaat acggttatcc acagaatcag      1020
gggataacgc aggaaagaac atgtgagcaa aaggccagca aaaggccagg aaccgtaaaa      1080
aggccgcgtt gctggcgttt ttccataggc tccgcccccc tgacgagcat cacaaaaatc      1140
gacgctcaag tcagaggtgg cgaaacccga caggactata agataccag gcgtttcccc       1200 ctggaagctc cctcgtgcgc tctcctgttc cgaccctgcc gcttaccgga tacctgtccg      1260
cctttctccc ttcgggaagc gtggcgcttt ctcatagctc acgctgtagg tatctcagtt      1320
cggtgtaggt cgttcgctcc aagctgggct gtgtgcacga accccccgtt cagcccgacc      1380
gctgcgcctt atccggtaac tatcgtcttg agtccaaccc ggtaagacac gacttatcgc      1440
cactggcagc agccactggt aacaggatta gcagagcgag gtatgtaggc ggtgctacag      1500
agttcttgaa gtggtggcct aactacggct acactagaag aacagtattt ggtatctgcg      1560
ctctgctgaa gccagttacc ttcggaaaaa gagttggtag ctcttgatcc ggcaaacaaa      1620
ccaccgctgg tagcggtggt ttttttgttt gcaagcagca gattacgcgc agaaaaaaag      1680
gatctcaaga agatccttg atctttcta cggggctagc gcttagaaga actcatccag        1740
cagacggtag aatgcaatac gttgagagtc tggagctgca ataccataca gaaccaggaa     1800
acggtcagcc cattcaccac ccagttcctc tgcaatgtca cgggtagcca gtgcaatgtc     1860
ctggtaacgg tctgcaacac ccagacgacc acagtcaatg aaaccagaga acgaccatt      1920 ctcaaccatg atgttcggca ggcatgcatc accatgagta actaccaggt cctcaccatc     1980
cggcatacga gctttcagac gtgcaaacag ttcagccggt gccagaccct gatgttcctc     2040
atccaggtca tcctggtcaa ccagacctgc ttccatacgg gtacgagcac gttcaatacg     2100
atgttttgcc tggtggtcaa acggacaggt agctgggtcc agggtgtgca gacgacgcat     2160
tgcatcagcc atgatagaaa ctttctctgc cggagccagg tgagaagaca gcaggtcctg     2220
acccggaact tcacccagca gcagccagtc acgaccagct tcagtaacta catccagaac     2280
tgcagcacac ggaacaccag tggttgccag ccaagacaga cgagctgctt catcctgcag     2340
ttcattcaga gcaccagaca ggtcagttttt aacaaacaga actggacgac cctgtgcaga    2400
cagacggaaa acagctgcat cagagcaacc aatggtctgc tgtgcccagt cataaccaaa     2460
cagacgttca acccaggctg ccggagaacc tgcatgcaga ccatcctgtt caatcatgcg     2520
aaacgatcct catcctgtct cttgatcaga tcttgatccc ctgcgccatc agatccttgg     2580
cggcaagaaa gccatccagt ttactttgca gggcttccca accttaccag agggcgcccc    2640
agctggcaat tccggttcgc ttgctgtcca taaaaccgcc cagtctagca actgttggga     2700
agggcgatcg                                                             2710
```

<210> SEQ ID NO 18
<211> LENGTH: 2713
<212> TYPE: DNA
<213> ORGANISM: artificial sequence
<220> FEATURE:
<223> OTHER INFORMATION: An analog GHRH sequence codon optimized for rat.

<400> SEQUENCE: 18

```
tgtaatacga ctcactatag ggcgaattgg agctccaccg cggtggcggc cgtccgccct       60
cggcaccatc ctcacgacac ccaaatatgg cgacgggtga ggaatggtgg ggagttattt      120
ttagagcggt gaggaaggtg ggcaggcagc aggtgttggc gctctaaaaa taactcccgg      180
gagttatttt tagagcggag gaatggtgga cacccaaata tggcgacggt tcctcacccg      240
```

-continued

```
tcgccatatt tgggtgtccg ccctcggccg gggccgcatt cctgggggcc gggcggtgct      300
cccgcccgcc tcgataaaag gctccggggc cggcggcggc ccacgagcta cccggaggag      360
cgggaggcgc caagcggatc ccaaggccca actccccgaa ccactcaggg tcctgtggac      420
agctcaccta gctgccatgg ccctgtgggt gttcttcgtg ctgctgaccc tgaccagcgg      480
aagccactgc agcctgcctc ccagccctcc cttcagggtg cgccggcacg ccgacgccat      540
cttcaccagc agctacagga ggatcctggg ccagctgtac gctaggaagc tcctgcacga      600
gatcatgaac aggcagcagg gcgagaggaa ccaggagcag aggagcaggt tcaactgata      660
agcttatcgg ggtggcatcc ctgtgacccc tccccagtgc ctctcctggc cctggaagtt      720
gccactccag tgcccaccag ccttgtccta ataaaattaa gttgcatcat tttgtctgac      780
taggtgtcct tctataatat tatggggtgg aggggggtgg tatggagcaa ggggcaagtt      840
gggaagacaa cctgtagggc tcgagggggg gcccggtacc agcttttgtt ccctttagtg      900
agggttaatt tcgagcttgg tcttccgctt cctcgctcac tgactcgctg cgctcggtcg      960
ttcggctgcg gcgagcggta tcagctcact caaaggcggt aatacggtta tccacagaat     1020
caggggataa cgcaggaaag aacatgtgag caaaaggcca gcaaaggcc aggaaccgta      1080
aaaaggccgc gttgctggcg ttttccata ggctccgccc ccctgacgag catcacaaaa      1140
atcgacgctc aagtcagagg tggcgaaacc cgacaggact ataaagatac caggcgtttc     1200
ccccctggaag ctccctcgtg cgctctcctg ttccgaccct gccgcttacc ggatacctgt    1260
ccgcctttct cccttcggga agcgtggcgc tttctcatag ctcacgctgt aggtatctca     1320
gttcggtgta ggtcgttcgc tccaagctgg gctgtgtgca cgaaccccc gttcagcccg      1380
accgctgcgc cttatccggt aactatcgtc ttgagtccaa cccggtaaga cacgacttat     1440
cgccactggc agcagccact ggtaacagga ttagcagagc gaggtatgta ggcggtgcta     1500
cagagttctt gaagtggtgg cctaactacg gctacactag aagaacagta tttggtatct     1560
gcgctctgct gaagccagtt accttcggaa aaagagttgg tagctcttga tccggcaaac     1620
aaaccaccgc tggtagcggt ggttttttg tttgcaagca gcagattacg cgcagaaaaa      1680
aaggatctca agaagatcct ttgatctttt ctacgggct agcgcttaga agaactcatc      1740
cagcagacgg tagaatgcaa tacgttgaga gtctggagct gcaataccat acagaaccag     1800
gaaacggtca gcccattcac cacccagttc ctctgcaatg tcacgggtag ccagtgcaat     1860
gtcctggtaa cggtctgcaa cacccagacg accacagtca atgaaaccag agaaacgacc     1920
attctcaacc atgatgttcg gcaggcatgc atcaccatga gtaactacca ggtcctcacc     1980
atccggcata cgagctttca gacgtgcaaa cagttcagcc ggtgccagac cctgatgttc     2040
ctcatccagg tcatcctggt caaccagacc tgcttccata cgggtacgag cacgttcaat     2100
acgatgtttt gcctggtggt caaacggaca ggtagctggg tccagggtgt gcagacgacg     2160
cattgcatca gccatgatag aaactttctc tgccggagcc aggtgagaag acagcaggtc     2220
ctgacccgga acttcaccca gcagcagcca gtcacgacca gcttcagtaa ctacatccag     2280
aactgcagca cacggaacac cagtggttgc cagccaagac agacgagctg cttcatcctg     2340
cagttcattc agagcaccag acaggtcagt tttaacaaac agaactggac gaccctgtgc     2400
agacagacgg aaaacagctg catcagagca accaatggtc tgctgtgccc agtcataacc     2460
aaacagacgt tcaacccagg ctgccggaga acctgcatgc agaccatcct gttcaatcat     2520
gcgaaacgat cctcatcctg tctcttgatc agatcttgat cccctgcgcc atcagatcct     2580
```

```
tggcggcaag aaagccatcc agtttacttt gcagggcttc ccaaccttac cagagggcgc    2640
cccagctggc aattccggtt cgcttgctgt ccataaaacc gcccagtcta gcaactgttg    2700
ggaagggcga tcg                                                       2713
```

<210> SEQ ID NO 19
<211> LENGTH: 2704
<212> TYPE: DNA
<213> ORGANISM: artificial sequence
<220> FEATURE:
<223> OTHER INFORMATION: An analog GHRH sequence codon optimized for
      bovine.

<400> SEQUENCE: 19

```
tgtaatacga ctcactatag ggcgaattgg agctccaccg cggtggcggc cgtccgccct      60
cggcaccatc ctcacgacac ccaaatatgg cgacggtgga ggaatggtgg ggagttattt     120
ttagagcggt gaggaaggtg ggcaggcagc aggtgttggc gctctaaaaa taactcccgg     180
gagttatttt tagagcggag gaatggtgga cacccaaata tggcgacggt tcctcacccg     240
tcgccatatt tgggtgtccg ccctcggccg gggccgcatt cctggggggcc gggcggtgct     300 cccgcccgcc tcgataaaag gctccgggcc cggcggcggc ccacgagcta cccggaggag     360
cgggaggcgc caagcggatc ccaaggccca actccccgaa ccactcaggg tcctgtggac     420
agctcaccta gctgccatgg tgctgtgggt gttcttcctg gtgaccctga ccctgagcag     480
cggctcccac ggctccctgc cctcccagcc tctgcgcatc cctcgctacg ccgacgccat     540
cttcaccaac agctaccgca aggtgctcgg ccagctcagc gcccgcaagc tcctgcagga     600
catcatgaac cggcagcagg gcgagcgcaa ccaggagcag ggagcctgat aagcttatcg     660
gggtggcatc cctgtgaccc ctccccagtg cctctcctgg ccctggaagt tgccactcca     720
gtgcccacca gccttgtcct aataaaatta gttgcatca ttttgtctga ctaggtgtcc     780
ttctataata ttatgggggtg agggggggtg gtatggagca aggggcaagt tgggaagaca     840
acctgtaggg ctcgaggggg ggcccggtac cagcttttgt tccctttagt gagggttaat     900
ttcgagcttg gtcttccgct tcctcgctca ctgactcgct gcgctcggtc gttcggctgc     960
ggcgagcggt atcagctcac tcaaaggcgg taatacggtt atccacagaa tcaggggata    1020
acgcaggaaa gaacatgtga gcaaaaggcc agcaaaaggc caggaaccgt aaaaaggccg    1080
cgttgctggc gtttttccat aggctccgcc cccctgacga gcatcacaaa aatcgacgct    1140
caagtcagag gtggcgaaac ccgacaggac tataaagata ccaggcgttt ccccctggaa    1200
gctccctcgt gcgctctcct gttccgaccc tgccgcttac cggatacctg tccgcctttc    1260
tcccttcggg aagcgtggcg ctttctcata gctcacgctg taggtatctc agttcggtgt    1320
aggtcgttcg ctccaagctg ggctgtgtgc acgaaccccc cgttcagccc gaccgctgcg    1380
ccttatccgg taactatcgt cttgagtcca acccggtaag acacgactta tcgccactgg    1440
cagcagccac tggtaacagg attagcagag cgaggtatgt aggcggtgct acagagttct    1500
tgaagtggtg gcctaactac ggctacacta agaacagat tttggtatc tgcgctctgc     1560 tgaagccagt taccttcgga aaaagagttg gtagctcttg atccggcaaa caaaccaccg    1620
ctggtagcgg tggtttttt gtttgcaagc agcagattac gcgcagaaaa aaaggatctc    1680
aagaagatcc tttgatcttt tctacggggc tagcgcttag aagaactcat ccagcagacg    1740
gtagaatgca atacgttgag agtctggagc tgcaatacca tacagaacca ggaaacggtc    1800
agcccattca ccacccagtt cctctgcaat gtcacgggta gccagtgcaa tgtcctggta    1860
```

-continued

```
acggtctgca acacccagac gaccacagtc aatgaaacca gagaaacgac cattctcaac    1920
catgatgttc ggcaggcatg catcaccatg agtaactacc aggtcctcac catccggcat    1980
acgagctttc agacgtgcaa acagttcagc cggtgccaga ccctgatgtt cctcatccag    2040
gtcatcctgg tcaaccagac ctgcttccat acgggtacga gcacgttcaa tacgatgttt    2100
tgcctggtgg tcaaacggac aggtagctgg gtccagggtg tgcagacgac gcattgcatc    2160
agccatgata gaaactttct ctgccggagc caggtgagaa acagcaggt cctgacccgg    2220 aacttcaccc agcagcagcc agtcacgacc agcttcagta actacatcca gaactgcagc    2280
acacggaaca ccagtggttg ccagccaaga cagacgagct gcttcatcct gcagttcatt    2340
cagagcacca gacaggtcag ttttaacaaa cagaactgga cgaccctgtg cagacagacg    2400
gaaaacagct gcatcagagc aaccaatggt ctgctgtgcc cagtcataac caaacagacg    2460
ttcaacccag gctgccggag aacctgcatg cagaccatcc tgttcaatca tgcgaaacga    2520
tcctcatcct gtctcttgat cagatcttga tcccctgcgc catcagatcc ttggcggcaa    2580
gaaagccatc cagtttactt tgcagggctt cccaaccta ccagagggcg ccccagctgg    2640
caattccggt tcgcttgctg tccataaaac cgcccagtct agcaactgtt gggaagggcg    2700
atcg                                                                 2704
```

<210> SEQ ID NO 20
<211> LENGTH: 2704
<212> TYPE: DNA
<213> ORGANISM: artificial sequence
<220> FEATURE:
<223> OTHER INFORMATION: An analog GHRH sequence codon optimized for ovine.

<400> SEQUENCE: 20

```
tgtaatacga ctcactatag ggcgaattgg agctccaccg cggtggcggc cgtccgccct     60
cggcaccatc ctcacgacac ccaaatatgg cgacgggtga ggaatggtgg ggagttatttt    120 ttagagcggt gaggaaggtg ggcaggcagc aggtgttggc gctctaaaaa taactcccgg    180
gagttatttt tagagcggag gaatggtgga cacccaaata tggcgacggt tcctcacccg    240
tcgccatatt tgggtgtccg ccctcggccg gggccgcatt cctggggggcc gggcggtgct    300 cccgcccgcc tcgataaaag gctccggggc cggcggcggc ccacgagcta cccggaggag    360
cgggaggcgc caagcggatc ccaaggccca actccccgaa ccactcaggg tcctgtggac    420
agctcaccta gctgccatgg tgctgtgggt gttcttcctg gtgaccctga ccctgagcag    480
cggaagccac ggcagcctgc ccagccagcc cctgaggatc cctaggtacg ccgacgccat    540
cttcaccaac agctacagga gatcctgggc cagctgagc gctaggaagc tcctgcagga    600
catcatgaac aggcagcagg gcgagaggaa ccaggagcag ggcgcctgat aagcttatcg    660
gggtggcatc cctgtgaccc ctccccagtg cctctcctgg ccctggaagt tgccactcca    720
gtgcccacca gccttgtcct aataaaatta agttgcatca ttttgtctga ctaggtgtcc    780
ttctataata ttatggggtg gaggggggtg gtatggagca aggggcaagt tgggaagaca    840
acctgtaggg ctcgaggggg ggcccggtac cagcttttgt tccctttagt gagggttaat    900
ttcgagcttg gtcttccgct tcctcgctca ctgactcgct gcgctcggtc gttcggctgc    960
ggcgagcggt atcagctcac tcaaaggcgg taatacggtt atccacagaa tcaggggata   1020
acgcaggaaa gaacatgtga gcaaaaggcc agcaaaaggc caggaaccgt aaaaaggccg   1080
cgttgctggc gtttttccat aggctccgcc cccctgacga gcatcacaaa aatcgacgct   1140
```

```
caagtcagag gtggcgaaac ccgacaggac tataaagata ccaggcgttt ccccctggaa    1200
gctccctcgt gcgctctcct gttccgaccc tgccgcttac cggatacctg tccgccttc     1260 tcccttcggg aagcgtggcg ctttctcata gctcacgctg taggtatctc agttcggtgt    1320
aggtcgttcg ctccaagctg ggctgtgtgc acgaacccc cgttcagccc gaccgctgcg     1380
ccttatccgg taactatcgt cttgagtcca acccggtaag acacgactta tcgccactgg    1440
cagcagccac tggtaacagg attagcagag cgaggtatgt aggcggtgct acagagttct    1500
tgaagtggtg gcctaactac ggctacacta agaacagt atttggtatc tgcgctctgc      1560
tgaagccagt taccttcgga aaagagttg gtagctcttg atccggcaaa caaaccaccg     1620
ctggtagcgg tggtttttt gtttgcaagc agcagattac gcgcagaaaa aaggatctc      1680 aagaagatcc tttgatcttt tctacggggc tagcgcttaa agaactcat ccagcagacg     1740 gtagaatgca atacgttgag agtctggagc tgcaatacca tacagaacca ggaaacggtc    1800
agcccattca ccacccagtt cctctgcaat gtcacgggta gccagtgcaa tgtcctggta    1860
acggtctgca cacccagac gaccacagtc aatgaaacca gagaaacgac cattctcaac    1920
catgatgttc ggcaggcatg catcaccatg agtaactacc aggtcctcac catccggcat    1980
acgagctttc agacgtgcaa acagttcagc cggtgccaga ccctgatgtt cctcatccag    2040
gtcatcctgg tcaaccagac ctgcttccat acgggtacga gcacgttcaa tacgatgttt    2100
tgcctggtgg tcaaacggac aggtagctgg gtccagggtg tgcagacgac gcattgcatc    2160
agccatgata gaaactttct ctgccggagc caggtgagaa acagcaggt cctgacccgg     2220 aacttcaccc agcagcagcc agtcacgacc agcttcagta actacatcca gaactgcagc    2280
acacggaaca ccagtggttg ccagccaaga cagacgagct gcttcatcct gcagttcatt    2340
cagagcacca gacaggtcag ttttaacaaa cagaactgga cgaccctgtg cagacagacg    2400
gaaaacagct gcatcagagc aaccaatggt ctgctgtgcc cagtcataac caaacagacg    2460
ttcaacccag gctgccggag aacctgcatg cagaccatcc tgttcaatca tgcgaaacga    2520
tcctcatcct gtctcttgat cagatcttga tcccctgcgc catcagatcc ttggcggcaa    2580
gaaagccatc cagtttactt tgcagggctt cccaaccta ccagagggcg ccccagctgg     2640
caattccggt tcgcttgctg tccataaaac cgcccagtct agcaactgtt gggaagggcg    2700
atcg                                                                 2704
```

<210> SEQ ID NO 21
<211> LENGTH: 2713
<212> TYPE: DNA
<213> ORGANISM: artificial sequence
<220> FEATURE:
<223> OTHER INFORMATION: An analog GHRH sequence codon optimized for chicken.

<400> SEQUENCE: 21

```
tgtaatacga ctcactatag ggcgaattgg agctccaccg cggtggcggc cgtccgccct    60
cggcaccatc ctcacgacac ccaaatatgg cgacgggtga ggaatggtgg ggagttattt    120
ttagagcggt gaggaaggtg ggcaggcagc aggtgttggc gctctaaaaa taactcccgg    180
gagttatttt tagagcggag gaatggtgga cacccaaata tggcgacggt tcctcacccg    240
tcgccatatt tgggtgtccg ccctcggccg gggccgcatt cctgggggcc gggcggtgct    300
cccgcccgcc tcgataaaag gctccggggc cggcggcggc ccacgagcta cccggaggag    360
cgggaggcgc caagcggatc ccaaggccca actccccgaa ccactcaggg tcctgtggac    420
```

-continued

```
agctcaccta gctgccatgg ccctgtgggt gttctttgtg ctgctgaccc tgacctccgg      480
aagccactgc agcctgccac ccagcccacc cttccgcgtc aggcgccacg ccgacggcat      540
cttcagcaag gcctaccgca agctcctggg ccagctgagc gcacgcaact acctgcacag      600
cctgatggcc aagcgcgtgg gcagcggact gggagacgag gccgagcccc tgagctgata      660
agcttatcgg ggtggcatcc ctgtgacccc tccccagtgc ctctcctggc cctggaagtt      720
gccactccag tgcccaccag ccttgtccta ataaaattaa gttgcatcat tttgtctgac      780
taggtgtcct tctataatat tatgggtgg aggggtgg tatggagcaa ggggcaagtt        840
gggaagacaa cctgtagggc tcgagggggg gcccggtacc agcttttgtt ccctttagtg      900
agggttaatt tcgagcttgg tcttccgctt cctcgctcac tgactcgctg cgctcggtcg      960
ttcggctgcg cgagcggta tcagctcact caaaggcggt aatacggtta ccacagaat      1020 caggggataa cgcaggaaag aacatgtgag caaaaggcca gcaaaaggcc aggaaccgta     1080
aaaaggccgc gttgctggcg ttttttccata ggctccgccc ccctgacgag catcacaaaa     1140
atcgacgctc aagtcagagg tggcgaaacc cgacaggact ataaagatac caggcgtttc     1200
cccctggaag ctccctcgtg cgctctcctg ttccgaccct gccgcttacc ggatacctgt     1260
ccgcctttct cccttcggga agcgtggcgc tttctcatag ctcacgctgt aggtatctca     1320
gttcggtgta ggtcgttcgc tccaagctgg gctgtgtgca cgaaccccc gttcagcccg      1380 accgctgcgc cttatccggt aactatcgtc ttgagtccaa cccggtaaga cacgacttat     1440
cgccactggc agcagccact ggtaacagga ttagcagagc gaggtatgta ggcggtgcta     1500
cagagttctt gaagtggtgg cctaactacg gctacactag aagaacagta tttggtatct     1560
gcgctctgct gaagccagtt accttcggaa aaagagttgg tagctcttga tccggcaaac     1620
aaaccaccgc tggtagcggt ggttttttttg tttgcaagca gcagattacg cgcagaaaaa    1680
aaggatctca agaagatcct ttgatctttt ctacggggct agcgcttaga agaactcatc     1740
cagcagacgg tagaatgcaa tacgttgaga gtctggagct gcaataccat acagaaccag     1800
gaaacggtca gcccattcac cacccagttc tctgcaatg tcacgggtag ccagtgcaat    1860
gtcctggtaa cggtctgcaa cacccagacg accacagtca atgaaaccag agaaacgacc     1920
attctcaacc atgatgttcg gcaggcatgc atcaccatga gtaactacca ggtcctcacc     1980
atccggcata cgagctttca gacgtgcaaa cagttcagcc ggtgccagac cctgatgttc     2040
ctcatccagg tcatcctggt caaccagacc tgcttccata cgggtacgag cacgttcaat     2100
acgatgtttt gcctggtggt caaacggaca ggtagctggg tccagggtgt gcagacgacg     2160
cattgcatca gccatgatag aaactttctc tgccggagcc aggtgagaag acagcaggtc     2220
ctgacccgga acttcaccca gcagcagcca gtcacgacca gcttcagtaa ctacatccag     2280
aactgcagca cacggaacac cagtggttgc cagccaagac agacgagctg cttcatcctg     2340
cagttcattc agagcaccag acaggtcagt tttaacaaac agaactggac gaccctgtgc     2400
agacagacgg aaaacagctg catcagagca accatggtc tgctgtgccc agtcataacc      2460
aaacagacgt tcaacccagg ctgccggaga acctgcatgc agaccatcct gttcaatcat     2520
gcgaaacgat cctcatcctg tctcttgatc agatcttgat ccctgcgcc atcagatcct     2580 tggcggcaag aaagccatcc agtttacttt gcagggcttc ccaaccttac cagagggcgc     2640
cccagctggc aattccggtt cgcttgctgt ccataaaacc gcccagtcta gcaactgttg     2700
ggaagggcga tcg                                                         2713
```

```
<210> SEQ ID NO 22
<211> LENGTH: 55
<212> TYPE: DNA
<213> ORGANISM: artificial sequence
<220> FEATURE:
<223> OTHER INFORMATION: Sequence of a human GH 5' UTR.

<400> SEQUENCE: 22
caaggcccaa ctccccgaac cactcagggt cctgtggaca gctcacctag ctgcc         55

<210> SEQ ID NO 23
<211> LENGTH: 782
<212> TYPE: DNA
<213> ORGANISM: artificial sequence
<220> FEATURE:
<223> OTHER INFORMATION: Sequence of a plasmid pUC-18 origin of
      replicaiton.

<400> SEQUENCE: 23
tcttccgctt cctcgctcac tgactcgctg cgctcggtcg ttcggctgcg gcgagcggta    60
tcagctcact caaaggcggt aatacggtta tccacagaat caggggataa cgcaggaaag   120
aacatgtgag caaaaggcca gcaaaaggcc aggaaccgta aaaaggccgc gttgctggcg   180
tttttccata ggctccgccc ccctgacgag catcacaaaa atcgacgctc aagtcagagg   240
tggcgaaacc cgacaggact ataaagatac caggcgtttc ccctggaag ctccctcgtg    300 cgctctcctg ttccgaccct gccgcttacc ggatacctgt ccgcctttct cccttcggga   360
agcgtggcgc tttctcatag ctcacgctgt aggtatctca gttcggtgta ggtcgttcgc   420
tccaagctgg gctgtgtgca cgaaccccccc gttcagcccg accgctgcgc cttatccggt   480
aactatcgtc ttgagtccaa cccggtaaga cacgacttat cgccactggc agcagccact   540
ggtaacagga ttagcagagc gaggtatgta ggcggtgcta cagagttctt gaagtggtgg   600
cctaactacg gctacactag aaggacagta tttggtatct gcgctctgct gaagccagtt   660
accttcggaa aaagagttgg tagctcttga tccggcaaac aaaccaccgc tggtagcggt   720
ggtttttttg tttgcaagca gcagattacg cgcagaaaaa aaggatctca agaagatcct   780
tt                                                                  782

<210> SEQ ID NO 24
<211> LENGTH: 5
<212> TYPE: DNA
<213> ORGANISM: artificial sequence
<220> FEATURE:
<223> OTHER INFORMATION: This is a NEO ribosomal binding site.

<400> SEQUENCE: 24 tcctc                                                                5

<210> SEQ ID NO 25
<211> LENGTH: 29
<212> TYPE: DNA
<213> ORGANISM: artificial sequence
<220> FEATURE:
<223> OTHER INFORMATION: Sequence of a prokaryotic PNEO promoter.

<400> SEQUENCE: 25
accttaccag agggcgcccc agctggcaa                                      29
```